United States Patent
Oral et al.

(10) Patent No.: US 9,889,224 B2
(45) Date of Patent: *Feb. 13, 2018

(54) SPATIAL CONTROL OF ADDITIVES BY HIGH TEMPERATURE

(71) Applicant: THE GENERAL HOSPITAL CORPORATION, Boston, MA (US)

(72) Inventors: Ebru Oral, FNewon, MA (US); Chhavi Gupta, Faridabad (IN); Orhun Muratoglu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/420,005

(22) PCT Filed: Aug. 2, 2013

(86) PCT No.: PCT/US2013/053396
§ 371 (c)(1),
(2) Date: Feb. 6, 2015

(87) PCT Pub. No.: WO2014/025636
PCT Pub. Date: Feb. 13, 2014

(65) Prior Publication Data
US 2015/0190545 A1     Jul. 9, 2015

Related U.S. Application Data

(60) Provisional application No. 61/679,952, filed on Aug. 6, 2012.

(51) Int. Cl.
*A61F 2/02*     (2006.01)
*A61F 2/30*     (2006.01)
(Continued)

(52) U.S. Cl.
CPC .............. *A61L 27/16* (2013.01); *A61F 2/30* (2013.01); *A61L 17/04* (2013.01); *A61L 17/14* (2013.01);
(Continued)

(58) Field of Classification Search
None
See application file for complete search history.

(56) References Cited

U.S. PATENT DOCUMENTS 5,879,400 A * 3/1999 Merrill ...................... A61F 2/32
526/352
6,448,315 B1 * 9/2002 Lidgren ................. A61L 27/16
524/110
(Continued)

FOREIGN PATENT DOCUMENTS

WO     2008/092047 A1    7/2008
WO     WO 2008092047 A1 *    7/2008 .............. C08F 10/02

OTHER PUBLICATIONS

International Search Report and Written Opinioin under dated Oct. 24, 2013 in connection with PCT/US2013/053396.

*Primary Examiner* — Peter A Salamon
(74) *Attorney, Agent, or Firm* — Quarles & Brady LLP

(57) ABSTRACT

Provided is a method of making a polymeric material with a spatially controlled distribution of one or more additives including the steps of blending the one or more additives with a polymeric material, consolidating the polymeric material, heating at least a portion of at least one surface of the consolidated additive-blended polymeric material, and cooling the heated consolidated additive-blended polymeric material, thereby forming a polymeric material with a spatially controlled distribution of additive.

17 Claims, 32 Drawing Sheets

(51) Int. Cl.
  B29C 43/52    (2006.01)
  B29C 45/72    (2006.01)
  B29C 35/08    (2006.01)
  A61L 27/16    (2006.01)
  C08J 3/28     (2006.01)
  C08K 5/1545   (2006.01)
  C08J 3/20     (2006.01)
  A61L 27/50    (2006.01)
  A61L 29/04    (2006.01)
  A61L 29/14    (2006.01)
  A61L 31/04    (2006.01)
  A61L 31/14    (2006.01)
  A61L 17/04    (2006.01)
  A61L 17/14    (2006.01)
  C08F 10/02    (2006.01)
  B29C 35/16    (2006.01)
  C08K 9/08     (2006.01)
  B29L 31/00    (2006.01)

(52) U.S. Cl.
  CPC ............ *A61L 27/50* (2013.01); *A61L 27/505* (2013.01); *A61L 29/041* (2013.01); *A61L 29/14* (2013.01); *A61L 31/048* (2013.01); *A61L 31/14* (2013.01); *B29C 43/52* (2013.01); *B29C 45/7207* (2013.01); *C08J 3/203* (2013.01); *C08J 3/28* (2013.01); *C08K 5/1545* (2013.01); *A61F 2/3094* (2013.01); *A61L 2430/24* (2013.01); *B29C 35/16* (2013.01); *B29C 2035/085* (2013.01); *B29C 2035/0827* (2013.01); *B29C 2035/0844* (2013.01); *B29C 2035/0877* (2013.01); *B29L 2031/00* (2013.01); *C08F 10/02* (2013.01); *C08K 9/08* (2013.01)

(56) References Cited

U.S. PATENT DOCUMENTS

| | | | |
|---|---|---|---|
| 8,293,811 B2 * | 10/2012 | Muratoglu | C08F 10/02 522/111 |
| 2005/0194723 A1 * | 9/2005 | Muratoglu | A61L 27/16 264/488 |
| 2008/0215142 A1 * | 9/2008 | Muratoglu | A61L 27/16 623/1.49 |
| 2010/0190882 A1 * | 7/2010 | Muratoglu | C08F 10/02 522/129 |
| 2012/0292816 A1 * | 11/2012 | Muratoglu | C08F 10/02 264/274 |
| 2015/0190545 A1 * | 7/2015 | Oral | A61F 2/30 523/115 |

* cited by examiner

SPATIAL CONTROL OF ADDITIVES BY HIGH TEMPERATURE

CROSS REFERENCES TO RELATED APPLICATIONS

This application is a 371 application of PCT/US2013/053396 filed Aug. 2, 2013 which claims priority from U.S. Provisional Patent Application No. 61/679,952, filed Aug. 6, 2012.

STATEMENT REGARDING FEDERALLY SPONSORED RESEARCH

Not Applicable.

BACKGROUND OF THE INVENTION

1. Field of the Invention

The invention describes methods of making cross-linked total joint implants by controlling the spatial control of anti-cross-linking agents. The invention uses methods of extracting anti-cross-linking agents and controlling antioxidant concentrations in polymeric materials for joint implants.

2. Background of the Invention

Radiation cross-linking of polymers enhances many of their mechanical properties. For ultrahigh molecular weight polyethylene (UHMWPE), radiation cross-linking can also enhance its wear resistance under bi-directional motion similar to that experienced in human joints. However, radiation cross-linking can also decrease the toughness of UHMWPE with increasing radiation dose. Thus, controlling cross-linking spatially such that only portions of the polymer are cross-linked may be desirable to maintain the toughness of the material while improving its wear resistance.

Spatially controlling cross-linking in polymers can be performed in several ways; one approach is to use a spatial distribution of an additive in the polymer which can decrease cross-linking. This invention describes methods of extracting and/or incorporating additives in a polymeric material, for example, to spatially control the concentration profile of the additive in the polymeric material.

SUMMARY OF THE INVENTION

Additives can be incorporated into a polymeric material using different methods. One method involves blending one or more types of resin, flakes or powder of the polymeric material with different concentrations of additives. Then, the polymeric material can be used in unconsolidated form or consolidated into larger solid forms, for example rectangular blocks or cylindrical pucks from which test coupons, implant preforms, or implants can be machined.

Exposing the consolidated polymeric material containing one or more additives ("additives") to a high temperature may lead to oxidation of the polymer, and/or oxidation, consumption, degradation, and/or evaporation of the additives, thereby leading to the extraction of the additives. Loss of the additives when exposed to high temperature may be on the surface of the material, creating a concentration gradient in the material with the bulk having higher concentrations of additives than the surface.

One class of additives includes antioxidants. In this case, the additives can decrease cross-linking in UHMWPE when exposed to cross-linking conditions using radiation or chemical cross-linking methods.

In some embodiments, consolidated polymeric material with a spatially controlled distribution of additives is further cross-linked. Cross-linking can be initiated by ionizing radiation such as a gamma or electron beam irradiation.

A spatially controlled distribution of additives can be created before, during and after extraction of additives from desired surfaces by a combination of diffusion from the bulk and/or diffusion from external sources. In some embodiments, while extraction is being performed on one or more desired surfaces by high temperature exposure, an external doping source of additive is used from one or more surfaces where extraction of additive is not desired. The doping source may be used to replenish some of the additive that has diffused toward the extracted region on the surface.

If a spatial distribution of additives is not desired during high temperature melting, then all surfaces of the polymeric need to be masked to prevent extraction. Alternatively, the surface regions can be machined away to obtain a medical implant preform or medical implant with uniform additive concentration or uniform cross-linking after irradiation.

In any of embodiments, during the high temperature extraction of additive from surfaces, implant geometry may change due to thermal processes such as melting and recrystallization. In this case, implant preforms can be used for processing after which one or more machining steps can be used to obtain a final solid form intended for use such as an implant.

In one embodiment, the invention provides methods of making polymeric material with a spatially controlled distribution of additive comprising: (a) blending additive with a polymeric material; (b) consolidating the polymeric material; (c) exposing one or more surface(s) of the consolidated additive-blended polymeric material to high temperature; (d) cooling the heated consolidated antioxidant-blended polymeric material; thereby forming a polymeric material with a spatially controlled distribution of additive.

Cooling of any of the polymeric material(s) after high temperature exposure is performed until the temperature of the polymeric material is below the crystallization temperature. Although the final temperature of the polymeric material is desired to be close to room temperature (20° C. to 25° C.), cooling can be performed at any rate and any number of setpoints below or above room temperature in between. For example, a polymeric material can be cooled by exposing to liquid nitrogen (approximately −196° C.), then warmed to room temperature, or it can be brought first to 60° C., then cooled to room temperature. The cooling rate can be variable during cooling in a stepwise or in a continuous manner. Cooling can be done at the same environment as heating or in a different environment. Cooling can be performed in inert gas, a non-inert gas, air, vacuum, a liquid, a liquid with gas bubbled through, a liquid saturated with gas, a supercritical fluid or mixtures thereof. Inert gases can be nitrogen or argon or any other inert gas. Cooling can also be done in direct contact or in a chamber in contact with cooling fluid(s). Such a cooling fluid can be inert gas, water, ethanol, dry ice, liquid nitrogen. Heating and/or cooling can be done in static or dynamic flow of fluids in contact with the polymeric material or in contact with the chamber in which the polymeric material is maintained. The duration of cooling finally to room temperature can be between 1 minute to 1000 hours, or between 1 hour and 12 hours, more preferably about 2 hours.

In one embodiment, the invention provides methods of making polymeric material with a spatially controlled distribution of antioxidant(s) comprising: (a) blending antioxidant(s) with a polymeric material; (b) consolidating the polymeric material; (c) exposing one or more surface(s) of the consolidated antioxidant-blended polymeric material to high temperature; (d) cooling the heated consolidated antioxidant-blended polymeric material; thereby forming a polymeric material with a spatially controlled distribution of antioxidant(s).

In one embodiment, the invention provides methods of making polymeric material with a spatially controlled distribution of vitamin E comprising: (a) blending vitamin E with a polymeric material; (b) consolidating the polymeric material; (c) exposing one or more surface(s) of the consolidated vitamin E-blended polymeric material to high temperature; (d) cooling the heated consolidated vitamin E-blended polymeric material; thereby forming a polymeric material with a spatially controlled distribution of vitamin E.

In one embodiment, the invention provides methods of making cross-linked additive-blended polymeric material comprising: (a) blending additive with a polymeric material; (b) consolidating the polymeric material; (c) exposing one or more surface(s) of the consolidated additive-blended polymeric material to high temperature; (d) cooling the heated consolidated antioxidant-blended polymeric material; (e) irradiating the high temperature extracted consolidated additive-blended polymeric material thereby forming a cross-linked additive-blended polymeric material.

In one embodiment, the invention provides methods of making a cross-linked antioxidant-blended polymeric material with a spatial distribution of cross-linking comprising: (a) blending additive with a polymeric material; (b) consolidating the polymeric material; (c) exposing one or more surface(s) of the consolidated additive-blended polymeric material to high temperature; (d) cooling the heated consolidated antioxidant-blended polymeric material; (e) irradiating the high temperature extracted consolidated antioxidant-blended polymeric material thereby forming a cross-linked additive-blended polymeric material with a spatially controlled distribution of cross-linking.

In one embodiment, the invention provides methods of making a cross-linked vitamin E-blended polymeric material with a spatial distribution of cross-linking comprising: (a) blending vitamin E with a polymeric material; (b) consolidating the polymeric material; (c) exposing one or more surface(s) of the consolidated vitamin E-blended polymeric material to high temperature; (d) cooling the heated consolidated vitamin E-blended polymeric material; (e) irradiating the high temperature extracted consolidated vitamin E-blended polymeric material thereby forming a cross-linked additive-blended polymeric material with a spatially controlled distribution of cross-linking.

In one embodiment, the invention provides methods of making a medical implant comprising: (a) blending additive with a polymeric material; (b) consolidating the polymeric material; (c) machining the consolidated polymeric material into a medical implant preform; (d) exposing one or more surface(s) of the medical implant preform to high temperature; (e) cooling the medical implant preform; f) irradiating the medical implant preform.

In one embodiment, the invention provides methods of making a medical implant comprising: (a) blending additive with a polymeric material; (b) consolidating the polymeric material; (c) machining the consolidated polymeric material into a medical implant preform; (d) exposing one or more surface(s) of the medical implant preform to high temperature; (e) cooling the medical implant preform; (f) machining the medical implant preform, thereby forming a medical implant; and (g) irradiating the medical implant.

In one embodiment, the invention provides methods of making a hybrid, interlocked medical implant comprising: (a) blending additive with a polymeric material; (b) consolidating the polymeric material onto a second porous material; thereby forming a hybrid, interlocked medical implant preform; (c) exposing one or more surface(s) of the hybrid, interlocked medical implant preform to high temperature; (d) cooling the hybrid, interlocked medical implant preform; (e) machining the hybrid, interlocked medical implant preform, thereby forming a medical implant; and (f) irradiating the medical implant.

In one embodiment, the invention provides methods of making a medical implant with a spatially controlled distribution of cross-linking comprising: (a) blending additive with a polymeric material; (b) consolidating the polymeric material; (c) machining the consolidated polymeric material into a medical implant preform; (d) exposing one or more surface(s) of the medical implant preform to high temperature; (e) cooling the medical implant preform; and (f) irradiating the medical implant preform; thereby forming a medical implant with a spatially controlled distribution of cross-linking.

In some embodiments, after high temperature exposure for extraction of additive from one or more surface(s), a small amount can be machined from the polymeric material or medical implant preform to obtain a final medical implant complying with clearance requirements of a final medical implant design. This machining can be 1 micron to 5 millimeters, preferably 100 microns to 1 millimeters, most preferably about 200 microns (also micra).

In one embodiment, the invention provides methods of making a medical implant with a spatially controlled distribution of cross-linking comprising: (a) blending additive with a polymeric material; (b) consolidating the polymeric material; (c) machining the consolidated polymeric material into a medical implant preform; (d) exposing one or more surface(s) of the medical implant preform to high temperature; (e) cooling the medical implant preform; (f) machining the medical implant preform, thereby forming a medical implant, and (g) irradiating the medical implant; thereby forming a medical implant with a spatially controlled distribution of cross-linking.

In some embodiments, the incorporation of the additive can be performed by diffusion of the additive into already consolidated polymeric material. Such an additive-doped polymeric material doped by diffusion can be extracted on one or more surface(s) by exposing to high temperature to obtain a polymeric material with a spatially controlled distribution of additive. One or more additive can be antioxidant(s). One additive can be vitamin E.

In another embodiment, the invention provides methods of making additive-doped polymeric material comprising: (a) doping a consolidated polymeric material with antioxidant(s) by diffusion below or above the melting point; (b) exposing one or more surface(s) of the additive-doped polymeric material to high temperature; and (c) cooling the heated consolidated additive-doped polymeric material; thereby forming a polymeric material with a spatially controlled distribution of additive. One or more additive can be antioxidant(s). One additive can be vitamin E.

In one embodiment, the invention provides methods of making a cross-linked additive-doped polymeric material with a spatial distribution of cross-linking comprising: (a) consolidating the polymeric material; (b) doping the polymeric material with one or more additive; (c) exposing one or more surface(s) of the consolidated additive-doped polymeric material to high temperature; (d) cooling the heated consolidated additive-doped polymeric material; and (e) irradiating the high temperature extracted consolidated additive-doped polymeric material thereby forming a cross-linked additive-blended polymeric material with a spatially controlled distribution of cross-linking. One or more additive can be antioxidant(s). One additive can be vitamin E.

In one embodiment, the invention provides methods of making a cross-linked additive-doped medical implant with a spatial distribution of cross-linking comprising: (a) consolidating the polymeric material; (b) machining the consolidated polymeric material; thereby forming a medical implant preform; (c) doping the medical implant preform with one or more additive; (d) exposing one or more surface(s) of the consolidated additive-doped medical implant preform to high temperature; (e) cooling the heated medical implant preform; (f) irradiating the high temperature extracted medical implant preform thereby forming a medical implant with a spatially controlled distribution of cross-linking. One or more additive can be antioxidant(s). One additive can be vitamin E.

In one embodiment, the invention provides methods of making a cross-linked additive-doped medical implant with a spatial distribution of cross-linking comprising: (a) consolidating the polymeric material; (b) machining the consolidated polymeric material; thereby forming a medical implant preform; (c) doping the medical implant preform with one or more additive; (d) exposing one or more surface(s) of the consolidated additive-doped medical implant preform to high temperature; (e) cooling the heated medical implant preform; (f) machining the high temperature extracted medical implant preform; thereby forming a medical implant; and (g) irradiating the medical implant; thereby forming a medical implant with a spatially controlled distribution of cross-linking. One or more additive can be antioxidant(s). One additive can be vitamin E.

In one embodiment, the invention provides methods of making a cross-linked additive-doped polymeric material with a spatial distribution of cross-linking comprising: (a) blending one or more additive with the polymeric material; (b) consolidating the additive-blended polymeric material; (c) doping the polymeric material with one or more additive; d) exposing one or more surface(s) of the consolidated additive-blended and additive-doped polymeric material to high temperature; (d) cooling the heated consolidated additive-blended and additive-doped polymeric material it to room temperature; and (e) irradiating the high temperature extracted consolidated additive-blended and additive-doped polymeric material thereby forming a cross-linked additive-blended polymeric material with a spatially controlled distribution of cross-linking. One or more additive can be antioxidant(s). One additive can be vitamin E.

In one embodiment, the invention provides methods of making a cross-linked additive-doped medical implant with a spatial distribution of cross-linking comprising: (a) blending one or more additive with the polymeric material; (b) consolidating the additive-blended polymeric material; (c) machining the additive-blended polymeric material, thereby forming a medical implant preform; (d) doping the medical implant preform with one or more additive; (d) exposing one or more surface(s) of the medical implant preform to high temperature; (e) cooling the heated medical implant preform; and (f) irradiating the high temperature extracted medical implant preform; thereby forming a medical implant with a spatially controlled distribution of cross-linking. One or more additive can be antioxidant(s). One additive can be vitamin E.

In one embodiment, the invention provides methods of making a cross-linked additive-doped medical implant with a spatial distribution of cross-linking comprising: (a) blending one or more additive with the polymeric material; (b) consolidating the additive-blended polymeric material; (c) machining the additive-blended polymeric material, thereby forming a medical implant preform; (d) doping the medical implant preform with one or more additive; (e) exposing one or more surface(s) of the medical implant preform to high temperature; (f) cooling the heated medical implant preform; (g) machining the medical implant preform; thereby forming a medical implant; and (h) irradiating the high temperature extracted medical implant; thereby forming a medical implant with a spatially controlled distribution of cross-linking. One or more additive can be antioxidant(s). One additive can be vitamin E.

In another embodiment, the invention provides methods of making additive-containing polymeric material comprising: (a) blending one or more additive with polymeric material; (b) consolidating the additive-blended polymeric material; (c) exposing one or more surface(s) of the additive the consolidated material to high temperature while simultaneously using a doping source to diffuse additive from one or more surface(s); (d) cooling the material; thereby forming a polymeric material with a spatially controlled distribution of additive.

In another embodiment, the invention provides methods of making antioxidant containing polymeric material comprising: (a) blending one or more antioxidant(s) with polymeric material; (b) consolidating the antioxidant-blended polymeric material; (c) exposing the consolidated polymeric material to high temperature, simultaneously using a doping source to diffuse antioxidant(s) from one or more surface(s); (d) cooling the material; thereby forming a polymeric material with a spatially controlled distribution of antioxidant(s).

In any of the embodiments, the doping source can be a consolidated polymeric material containing one or more additive that is contacted with the desired surface(s) of the polymeric material. The doping source can also be a layer of additive previously contacted with the polymeric material. The doping source can be a bath of additive in pure form, as mixtures or as solutions or emulsions in solvent. The doping source can be the additive stored in the pores of a porous second material, which can be polymeric, metallic or ceramic.

In another embodiment, the invention provides methods of making additive-containing cross-linked polymeric material comprising: (a) blending one or more additive with polymeric material; (b) consolidating the additive-blended polymeric material; (c) exposing one or more surface(s) of the additive-blended and consolidated polymeric material at high temperature while simultaneously using a doping source to diffuse additive from one or more surface(s); (d) cooling the material; (e) irradiating the high temperature extracted additive-containing polymeric material; thereby forming a polymeric material with a spatially controlled distribution of cross-links.

In another embodiment, the invention provides methods of making antioxidant-containing cross-linked polymeric material comprising: (a) blending one or more antioxidant(s) with polymeric material; (b) consolidating the antioxidant-blended polymeric material; (c) exposing one or more surface(s) of the antioxidant-blended and consolidated polymeric material at high temperature while simultaneously using a doping source to diffuse antioxidant(s) from one or more surface(s); (d) cooling the material; (e) irradiating the high temperature extracted antioxidant-containing polymeric material; thereby forming a polymeric material with a spatially controlled distribution of cross-links.

In another embodiment, the invention provides methods of making vitamin E-containing cross-linked polymeric material comprising: (a) blending vitamin E with polymeric material; (b) consolidating the vitamin E-blended polymeric material; (c) exposing one or more surface(s) of the vitamin E-blended and consolidated polymeric material at high temperature while simultaneously using a doping source to diffuse antioxidant(s) from one or more surface(s); (d) cooling the material; (e) irradiating the high temperature extracted vitamin E-containing polymeric material; thereby forming a polymeric material with a spatially controlled distribution of cross-links.

In another embodiment, the invention provides methods of making additive-containing cross-linked medical implant comprising: (a) blending one or more additive with polymeric material; (b) consolidating the additive-blended polymeric material; (c) machining the polymeric material; thereby forming a medical implant preform; (d) exposing one or more surface(s) of the additive-blended medical implant preform at high temperature while simultaneously using a doping source to diffuse additive from one or more surface(s); (e) cooling the preform; and (f) irradiating the high temperature extracted medical implant preform; thereby forming a medical implant with a spatially controlled distribution of cross-links.

In another embodiment, the invention provides methods of making antioxidant-containing cross-linked medical implant comprising: (a) blending one or more antioxidant(s) with polymeric material; (b) consolidating the antioxidant-blended polymeric material; (c) machining the polymeric material; thereby forming a medical implant preform; (d) exposing one or more surface(s) of the antioxidant-blended medical implant preform at high temperature while simultaneously using a doping source to diffuse antioxidant(s) from one or more surface(s); (e) cooling the preform; and (f) irradiating the high temperature extracted medical implant preform; thereby forming a medical implant with a spatially controlled distribution of cross-links.

In another embodiment, the invention provides methods of making vitamin E-containing cross-linked medical implant comprising: (a) blending vitamin E with polymeric material; (b) consolidating the vitamin E-blended polymeric material; (c) machining the polymeric material; thereby forming a medical implant preform; (d) exposing one or more surface(s) of the vitamin E-blended medical implant preform at high temperature while simultaneously using a doping source to diffuse vitamin E from one or more surface(s); (e) cooling the preform; and (f) irradiating the high temperature extracted medical implant preform; thereby forming a medical implant with a spatially controlled distribution of cross-links.

In any of the embodiments, more than one antioxidant or additive can be blended with or diffused into the polymeric material. The purpose of the addition of various components can be different, for instance one additive can be used in creating the spatially controlled distribution of cross-links after irradiation due to its anticross-linking ability and another additive can be used to impart oxidation resistance.

In another embodiment, the invention provides methods of making additive-containing cross-linked medical implant comprising: (a) blending one or more additive with polymeric material; (b) consolidating the additive-blended polymeric material; (c) machining the polymeric material; thereby forming a medical implant preform; (d) exposing one or more surface(s) of the additive-blended medical implant preform at high temperature while simultaneously using a doping source to diffuse additive from one or more surface(s); (e) cooling the preform; (f) machining the high temperature extracted medical implant preform; thereby forming a medical implant; and (g) irradiating the medical implant; thereby forming a medical implant with a spatially controlled distribution of cross-links.

In another embodiment, the invention provides methods of making antioxidant-containing cross-linked medical implant comprising: (a) blending one or more antioxidant(s) with polymeric material; (b) consolidating the antioxidant-blended polymeric material; (c) machining the polymeric material; thereby forming a medical implant preform; (d) exposing one or more surface(s) of the antioxidant-blended medical implant preform at high temperature while simultaneously using a doping source to diffuse antioxidant(s) from one or more surface(s); (e) cooling the preform; (f) machining the high temperature extracted medical implant preform; thereby forming a medical implant; and (g) irradiating the medical implant; thereby forming a medical implant with a spatially controlled distribution of cross-links.

In another embodiment, the invention provides methods of making vitamin E-containing cross-linked medical implant comprising: (a) blending vitamin E with polymeric material; (b) consolidating the vitamin E-blended polymeric material; (c) machining the polymeric material; thereby forming a medical implant preform; (d) exposing one or more surface(s) of the vitamin E-blended medical implant preform at high temperature while simultaneously using a doping source to diffuse vitamin E from one or more surface(s); (e) cooling; (f) machining the high temperature extracted medical implant preform; thereby forming a medical implant; and (g) irradiating the medical implant; thereby forming a medical implant with a spatially controlled distribution of cross-links.

In any of the embodiments, after consolidation, the polymeric material can be heated to below or above its melting temperature to relieve the residual stresses from consolidation. For example, this temperature can be one or more temperature(s) between about 60° C. to about 200° C., more preferably about 100° C. to about 130° C. The duration for heating can be from 1 minute to more than 36 hours, more preferably from 1 hour to about 24 hours, most preferably about 8 hours. At this step, the temperature(s) and heating duration, to which the polymeric material is exposed, can be such that there is no extraction from the surfaces. Alternatively, the heating can be done with the surfaces covered to prevent extraction. If the heating is done at a temperature and a duration at which there was extraction from the surface(s), the polymeric material can be machined to remove the extracted layer.

In any of the embodiments, the additive blended or diffused into the polymer can comprise 0.001 wt % to more than 50 wt % of the polymeric material, preferably between 0.1 wt % and 5 wt %, more preferably about 1 wt %. In any of the embodiments, one or more antioxidant(s) can comprise 0.001 wt % to 100 wt % of the additive.

In any of the embodiments, the polymeric material at the beginning of the process can be in any unconsolidated form such as extrudate, pellet, resin powder, flakes, liquid or gel. The polymeric material can be consolidated by any polymer consolidation technique such as compression molding, ram extrusion, extrusion, hot or cold isostatic pressing, injection molding, direct compression molding. In the case of ultra-high molecular weight polyethylene, compression molding is the most commonly used technique, therefore consolidation can be used interchangeably with compression molding, but this does not limit the invention to consolidation by compression molding. The details of the consolidation process is described in the definitions; the consolidation process can be optimized in a manner clear to those skilled in the art to obtain consolidated polymeric material with high integrity, mechanical strength and toughness.

In any of the embodiments, the consolidated and/or machined forms of the polymeric material can have thickness from 100 microns to 100 centimeters, preferably between 1 millimeter to 20 centimeters, most preferably about 8 millimeters. The thickness of the polymeric material can vary within the consolidated and/or machined form depending on the design of the medical implant preform and medical implant.

In any of the embodiments, the high temperature, to which polymeric material is exposed for extraction of additive, can be from 200° C. to 500° C., more preferably from 220° C. to 300° C., most preferably about 290° C. The heating duration, which may include the time for the polymeric material to reach equilibrium at the extraction temperature, can be between 1 minute and 100 hours, more preferably between 1 hour and 4 hours, most preferably about 3 hours.

In any of the embodiments, the heating environment, for example for high temperature exposure, can be an inert gas, a non-inert gas, air, vacuum, a liquid, a liquid with gas bubbled through, a liquid saturated with gas, a supercritical fluid or mixtures thereof. Inert gases can be nitrogen or argon or any other inert gas. The pressure(s) during any step in processing can be between $10^{-9}$ atmospheres and 10000 atmospheres, for example between $10^{-6}$ atmospheres and 200 atmospheres. During high temperature extraction, full vacuum, partial vacuum, ambient pressure or pressurized atmospheres can be used.

In any of the embodiments, machining of the polymeric material, medical implant preform or medical implant shapes can be performed at any step of processing before packaging and sterilization of the implant. In any of the embodiments, the medical implant can be packaged and terminally sterilized in appropriate packaging. Sterilization can be done by gas sterilization methods such as ethylene oxide gas or gas plasma sterilization or ionizing radiation such as gamma sterilization.

In any of the embodiments, medical devices could be a permanent medical implant or a non-permanent medical implant. Medical devices selected from the group consisting of acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, interpositional devices for any joint, sutures, tendons, heart valves, stents, vascular grafts. The medical implant can be a non-permanent medical device, for example, a catheter, a balloon catheter, a tubing, an intravenous tubing, or a suture.

In any of the embodiments, other extraction methods such as extraction of the additive in a liquid, gas or fluid medium can be used before or after high temperature exposure. For example, extraction using organic solvents such as hexane, heptane or ethanol can be used. Alternatively, an aqueous medium such as an aqueous emulsion or solution can be used. These extraction methods can be used before or after high temperature exposure to modify the concentration profiles of additive. For example, the concentration of one or more additive can be lowered in the surface regions of the polymeric material or medical implant preform or medical implant.

In any of the embodiments, consolidated polymeric material could be masked during high temperature exposure or other extraction methods. Masking area could be anywhere from 0% to 99% of the total surface area. Parts of the same surface, for example articular surface, can be masked. In any of the embodiments, material used for masking could be any material whose dimensional change upon heating for high temperature exposure is small. Preferably, the masking material does not melt below or at the temperature used during high temperature exposure. If the masking material melts, it preferably does not exude or leach any parts into the polymeric material being masked. Examples of such materials can be metals such as aluminum, copper, iron or any other material which fits this description. The masking material can be of any practically feasible thickness, from 1 microns to 1 meter, preferably 100 microns to 500 microns.

In any of the embodiments, the steps of a process outlined in a method can be repeated once or many times. For example, high temperature exposure and cooling steps can be repeated. In any of the embodiments, heating and cooling can be applied at the same time to different parts of the polymeric material, medical implant preform or medical implant. For example, a medical implant preform can be cooled from a reservoir on its backside while being exposed to high temperature on its intended articular surfaces for extraction.

In any of the embodiments, polymeric material, medical implant preform or medical implants can be annealed after irradiation to redistribute one or more additive throughout the material. This annealing step can be used for the homogenization of the additive and can be performed below or above the melting point of the polymeric material. Annealing temperature can be between room temperature to 500° C., preferably between 100 and 170° C., most preferably 130° C. After this annealing step, the concentration profile of the additive does not need to be homogeneous.

In any of the embodiments, irradiation can be done by a gamma or electron beam irradiation. In any of the embodiments, irradiation temperature could be anywhere between 0° C. to 320° C., preferably between 25° C. and 130° C., most preferably between 40° C. and 130° C. Irradiation at elevated temperatures (warm irradiation), for example above 90° C., can have advantages such as increased cross-linking and increased grafting of the additive onto the polymer, decreasing elution. In any of the embodiments, irradiation environment could be nitrogen, argon or any other inert gas, air, oxygen or any other gas. In any of the embodiments, pressure during irradiation could be anywhere between $10^{-9}$ atm to 20 atm preferably between $10^{-6}$ atm to 1 atm. In any of the embodiments, total radiation dose could be between 1 kGy to 10000 kGy, preferably between 25 kGy to 250 kGy, most preferably about 200 kGy. Irradiation dose per pass can be varied, it can be between 0.00001 kGy/pass to 10000 kGy/pass, preferably about 25 kGy/pass to 100 kGy/pass. In the case of a gamma irradiation, the dose rate can be between 0.0000001 kGy/min to 10000 kGy/min, preferably about 0.01 kGy/min. The irradiation may be carried out in a sensitizing atmosphere. This may comprise a gaseous substance which is of sufficiently small molecular size to diffuse into the polymer and which, on irradiation, acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulphur monochloride, with chloro-tri-fluoroethylene (CTFE) or acetylene being particularly preferred. By "gaseous" is meant herein that the sensitizing atmosphere is in the gas phase at the irradiation temperature. In the case of electron beam irradiation, the beam energy could be between 500 keV and 20 MeV, preferably 10 MeV.

In any of embodiments, 0 millimeters to 10 centimeters of the material could be machined off from the extracted surface to get the desired geometry and dimensions of the medical device, preferably 0.1 millimeters to 1.5 millimeters of the material is machined off from the extracted surface.

In any of the embodiments, the medical implant is packaged and sterilized by ionizing radiation or gas sterilization, thereby forming a sterile and cross-linked oxidation-resistant medical implant.

In any of the embodiments, doping source could be blended polyethylene with antioxidant(s), polyethylene doped with antioxidant (s) via diffusion, free antioxidant(s), porous ceramic doped with antioxidant(s) via diffusion, porous polyethylene doped with antioxidant(s) via diffusion, porous polytetrafluoroethylene (e.g., Teflon®) doped with antioxidant(s) via diffusion.

In any of the embodiments if blended polyethylene with antioxidant(s) is used as a doping source, the concentration of antioxidant(s) could be anywhere between 0.01 wt % to 50 wt %, preferably between 0.5 wt % to 10 wt %.

In any of the embodiments, if free antioxidant(s) is used as a doping source, concentration could be 100% or it could be diluted with ethanol or any other solvent to reduce the concentration.

In any of the embodiments, doped porous ceramic, doped porous polyethylene, doped porous polytetrafluoroethylene, or doped polyethylene is obtained by keeping the doping material in antioxidant(s) solution for anywhere between 1 min to 100 days, preferably between 3 hours to 18 hours.

In any of the embodiments, the consolidated polymeric material or perform could be dipped in antioxidant(s) solution of concentration between 0.1 wt % to 100 wt %, preferably between 50 wt % to 100 wt %, before the extraction process.

A layer of blended polyethylene with antioxidant(s) is defined as consolidated polymeric material with uniform concentration of antioxidant(s). Therefore sequential layers of different or same antioxidant(s) concentration may be used to diffuse antioxidant(s) through different layers towards the back surface of medical implant or consolidated polymeric material. In any of the embodiments, when blended polyethylene is used as doping source, the number of sequential layers used as a doping source could be anywhere between 2 to 100 layers preferably between 2 to 4 layers.

In any of the embodiments, when blended polyethylene is used as a doping source, thickness of doping layers could be anywhere between 1 micron to 100 centimeters, preferably between 1 millimeters to 15 millimeters when blended polyethylene is used as doping source In any of the embodiments, doping source could be used throughout the duration of extraction or it could be a fraction of the extraction duration. Duration of doping source used could be anywhere between 1 minutes to 100 hours, preferably between 60 minutes to 8 hours.

In some embodiments, the invention comprises methods of making implants made out of surface extracted, cross-linked polymeric material. In some embodiments, the invention comprises methods of making implants made out of antioxidant-blended, surface extracted, cross-linked polymeric material. In some embodiments, the invention describes methods of providing wear resistant antioxidant-containing polymeric materials. In some embodiments, the invention describes methods of providing oxidation resistant antioxidant-containing polymeric materials.

These and other features, aspects, and advantages of the present invention will become better understood upon consideration of the following detailed description, drawings and claims.

DETAILED DESCRIPTION

Figure 1:
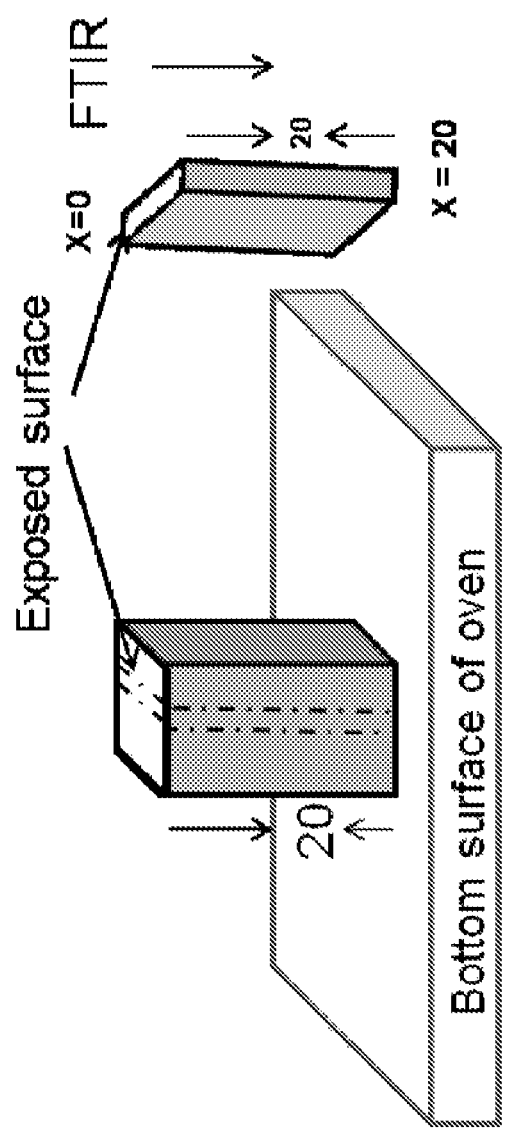
FIG. 1 is a schematic of the high temperature extraction of vitamin E from vitamin E-incorporated polymeric block (not drawn to scale—measurements in mm.).

The term 'cross-linked' refers to the state of a polymeric material with a cross-link density of at least 30 mol/m$^3$. The cross-link density is measured by swelling a roughly 3×3×3 mm cube of polymeric material in xylene. The samples are weighed before swelling in xylene at 130° C. for 2 hours and they are weighed immediately after swelling in xylene. The amount of xylene uptake is determined gravimetrically, then converted to volumetric uptake by dividing by the density of xylene (0.75 g/cm$^3$). By assuming the density of polyethylene to be approximately 0.94 g/cm$^3$, the volumetric swell ratio of cross-linked UHMWPE is then determined. The cross-link density is calculated using the swell ratio as described in Oral et al., Biomaterials 31: 7051-7060 (2010) and is reported in mol/m$^3$. Thus, a substantially cross-linked polymeric material has a cross-link density of about 30 mol/m$^3$ in at least one part of the polymeric material. The term 'highly cross-linked' refers to the state of a polymeric material with a cross-link density of about 100 mol/m$^3$ in at least one part of the polymeric material. For example, an implant with surfaces having a cross-link density of about 250 mol/m$^3$, and the bulk regions having a cross-link density of about 60 mol/m$^3$ would be highly cross-linked.

The term 'wear resistant' refers to the state of a polymeric material with a wear rate of less than 6 mg/million-cycles. The wear rate is tested on cylindrical pins (diameter=9 mm, length=13 mm) on a bidirectional pin-on-disc wear tester in undiluted bovine calf serum at 2 Hz in a rectangular pattern (5 mm×10 mm) under variable load with a maximum of 440 lbs as described in Bragdon et al., (J Arthroplasty 16: 658-665 (2001)). Initially, the pins are subjected to 0.5 million cycles (MC), after which they are tested to 1.25 million cycles with gravimetric measurements approximately every 0.125 MC. The wear rate is determined by the linear regression of the weight loss as a function of number of cycles from 0.5 to 1.25 MC. The term "highly wear resistant" refers to the state of a polymeric material with a wear rate of less than 3 mg/million-cycles.

"Polymeric materials" or "polymers" includes polyethylene. For example, ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHM-WPE starting material, prior to any irradiation. See U.S. Pat. No. 5,879,400, PCT/US99/16070, filed on Jul. 16, 1999, and PCT/US97/02220, filed Feb. 11, 1997. The term "polyethylene article" or "polymeric article" or "polymer" generally refers to articles comprising any "polymeric material" disclosed herein.

"Polymeric materials" or "polymers" also includes hydrogels, such as poly(vinyl alcohol), poly(acrylamide), poly(acrylic acid), poly(ethylene glycol), blends thereof, or interpenetrating networks thereof, which can absorb water such that water constitutes at least 1 to 10,000% of their original weight, typically 100 wt % of their original weight or 99% or less of their weight after equilibration in water.

"Polymeric material" or "polymer" can be in the form of resin, flakes, powder, consolidated stock, preform, implant, and can contain additives such as antioxidant(s). The "polymeric material" or "polymer" also can be a blend of one or more of different resin, flakes or powder containing different concentrations of an additive such as an antioxidant. The blending of resin, flakes or powder can be achieved by the blending techniques known in the art. The "polymeric material" also can be a consolidated stock of these blends.

The term 'irradiation' refers to exposing the polymeric material to a type of radiation source. Irradiation can be done by ultraviolet irradiation sources, gamma irradiation sources, electron beam irradiation sources or X-ray irradiation sources or others. Radiation cross-linking and thermal treatment methods are further defined as follows:

(i) Irradiation in the Molten State (IMS):

Melt-irradiation, or irradiation in the molten state ("IMS"), is described in detail in U.S. Pat. No. 5,879,400. In the IMS process, the polymer to be irradiated is heated to at or above its melting point. Then, the polymer is irradiated. Following irradiation, the polymer is cooled.

Prior to irradiation, the polymer is heated to at or above its melting temperature and maintained at this temperature for a time sufficient to allow the polymer chains to achieve an entangled state. A sufficient time period may range, for example, from about 5 minutes to about 3 hours. For UHMWPE, the polymer may be heated to a temperature between about 145° C. and about 320° C., preferably about 150° C. to about 200° C.

The temperature of melt-irradiation for a given polymer depends on the DSC (measured at a heating rate of 10° C./min during the first heating cycle) peak melting temperature ("PMT") for that polymer. In general, the irradiation temperature in the IMS process is about 2° C. higher than the PMT, more preferably between about 2° C. and about 20° C. higher than the PMT, and most preferably between about 5° C. and about 10° C. higher than the PMT. The temperature in the IMS process can be higher, up to 320° C.

The total dose of irradiation also may be selected as a parameter in controlling the properties of the irradiated polymer. In particular, the dose of irradiation can be varied to control the degree of cross-linking and crystallinity in the irradiated polymer. The total dose may range from about 0.1 MRad to about the irradiation level where the changes in the polymer characteristics induced by the irradiation reach a saturation point. For instance, the high end of the dose range could be 20 MRad for the melt-irradiation of UHMWPE, above which dose level the cross-link density and crystallinity are not appreciably affected with any additional dose. The preferred dose level depends on the desired properties that will be achieved following irradiation. Additionally, the level of crystallinity in polyethylene is a strong function of radiation dose level. See Dijkstra et al., Polymer 30: 866-73 (1989). For instance with IMS irradiation, a dose level of about 20 Mrad would decrease the crystallinity level of UHMWPE from about 55% to about 30%. This decrease in crystallinity may be desirable in that it also leads to a decrease in the elastic modulus of the polymer and consequently a decrease in the contact stress when a medical prosthesis made out of the IMS-treated UHMWPE gets in contact with another surface during in vivo use. Lower contact stresses are preferred to avoid failure of the polymer through, for instance, subsurface cracking, delamination, fatigue, etc. The increase in the cross-link density is also desirable in that it leads to an increase in the wear resistance of the polymer, which in turn reduces the wear of the medical prostheses made out of the cross-linked polymer and substantially reduces the amount of wear debris formed in vivo during articulation against a counterface. In general, the melt-irradiation and subsequent cooling will lead to a decrease in the crystallinity of the irradiated polymer.

(ii) Warm Irradiation:

Warm irradiation is described in detail in PCT International Application No. WO 97/29793. In the warm irradiation process, a polymer is provided at a temperature above room temperature and below the melting temperature of the polymer. Then, the polymer is irradiated. In one embodiment of warm irradiation, termed warm irradiation adiabatic melting (WIAM) the polymer may be irradiated at a high enough total dose and/or a high enough dose rate to generate enough heat in the polymer to result in at least a partial melting of the crystals of the polymer.

The adiabatic temperature rise depends on the dose level, level of insulation, and/or dose rate. Exemplary ranges of acceptable total dosages are disclosed in greater detail in WO 97/29793.

In some embodiments, UHMWPE is used as the starting polymer. In one embodiment, the total dose is about 0.5 MRad to about 1,000 Mrad. In another embodiment, the total dose is about 1 MRad to about 100 MRad. In yet another embodiment, the total dose is about 4 MRad to about 30 MRad. In still other embodiments, the total dose is about 20 MRad or about 15 MRad.

The polymer may be provided at any temperature below its melting point and above room temperature. The temperature selection depends on the specific heat and the enthalpy of melting of the polymer and the total dose level that will be used. The equation provided in PCT International Application No. WO 97/29793 may be used to calculate the preferred temperature range with the criterion that the final temperature of polymer may be below or above the melting point. Preheating of the polymer to the desired temperature may be done in an inert or non-inert environment.

Exemplary ranges of acceptable total dosages are disclosed in greater detail in PCT International Application No. WO 97/29793. In one embodiment, the UHMWPE is preheated to about 20° C. to about 135° C. In one embodiment, the UHMWPE is preheated to about 100° C. to just below the melting temperature of the polymer. In another embodiment, the UHMWPE is preheated to a temperature of about 100° C. to about 135° C. In yet other embodiments, the polymer is preheated to about 120° C. or about 130° C.

In general terms, the pre-irradiation heating temperature of the polymer can be adjusted based on the peak melting temperature (PMT) measure on the DSC at a heating rate of 10° C./minute during the first heat. In one embodiment, the polymer is heated to about 20° C. to about PMT. In another embodiment, the polymer is preheated to about 40° C., 50° C., 60° C., 70° C., 80° C. or 90° C. In another embodiment, the polymer is heated to about 100° C. In another embodiment, the polymer is preheated to about between 30° C. below PMT and 2° C. below PMT. In another embodiment, the polymer is preheated to about 12° C. below PMT.

In the WIAM embodiment of warm irradiation, the temperature of the polymer following irradiation is at or above the melting temperature of the polymer. Exemplary ranges of acceptable temperatures following irradiation are disclosed in greater detail in WO 97/29793. In one embodiment, the temperature following irradiation is about room temperature to PMT, or about 40° C. to PMT, or about 100° C. to PMT, or about 110° C. to PMT, or about 120° C. to PMT, or about PMT to about 200° C. In another embodiment, the temperature following irradiation is about 145° C. to about 190° C. In yet another embodiment, the temperature following irradiation is about 146° C. to about 190° C. In still another embodiment, the temperature following irradiation is about 150° C.

The dose rate of irradiation also may be varied to achieve a desired result. The dose rate is a prominent variable in the warm irradiation process. In the case of warm irradiation of UHMWPE, higher dose rates would provide the least amount of reduction in toughness and elongation at break. The preferred dose rate of irradiation would be to administer the total desired dose level in one pass under the electron-beam. One can also deliver the total dose level with multiple passes under the beam, delivering a (equal or unequal) portion of the total dose at each time. This would lead to a lower effective dose rate.

In some embodiments, double-sided irradiation may be used to achieve desired penetration depth and dose profiles in the polymeric material.

Ranges of acceptable dose rates are exemplified in greater detail in PCT International Application No. WO 97/29793. In general, the dose rates will vary between 0.5 MRad/pass and 50 MRad/pass. The upper limit of the dose rate depends on the resistance of the polymer to cavitation/cracking induced by the irradiation.

Depending on the polymer or polymer alloy used, and whether the polymer was irradiated below its melting point, there may be residual free radicals left in the material following the irradiation process. A polymer irradiated below its melting point with ionizing radiation contains cross-links as well as long-lived trapped free radicals. Some of the free radicals generated during irradiation become trapped at crystalline lamellae surfaces (see Kashiwabara, H. S. Shimada, and Y. Hori, Free Radicals and Crosslinking in Irradiated Polyethylene, Radiat. Phys. Chem., 1991, 37(1): p. 43-46) leading to oxidation-induced instabilities in the long-term (see Jahan, M. S. and C. Wang, Combined Chemical and Mechanical Effects on Free radicals in UHMWPE Joints During Implantation, Journal of Biomedical Materials Research, 1991, 25: p. 1005-1017; Sutula, L. C., et al., Impact of gamma sterilization on clinical performance of polyethylene in the hip", Clinical Orthopedic Related Research, 1995, 3129: p. 1681-1689.) The elimination of these residual, trapped free radicals through melt annealing is, therefore, desirable in precluding long-term oxidative instability of the polymer (see Jahan M. S. and C. Wang, "Combined chemical and mechanical effects on free radicals in UHMWPE joints during implantation", Journal of Biomedical Materials Research, 1991, 25: p. 1005-1017; Sutula, L. C., et al., "Impact of gamma sterilization on clinical performance of polyethylene in the hip", Clinical Orthopedic Related Research, 1995, 319: p. 28-4).

If there are residual free radicals remaining in the material, these may be reduced to substantially undetectable levels, as measured by electron spin resonance or other tests, through annealing of the polymer above the melting point of the polymeric system used. The melt annealing allows the residual free radicals to recombine with each other. If for a given system the preform does not have substantially any detectable residual free radicals following irradiation, then a melt annealing step may be omitted. Also, if for a given system, the concentration of the residual free radicals is low enough to not lead to degradation of device performance, the melt annealing step may be omitted. In a polymeric material where at least one additive is an antioxidant, a melting step after irradiation may be omitted or shortened. In a polymeric material where at least one additive is an antioxidant, an annealing step after irradiation may be omitted or shortened. Also, in a polymeric material where at least one additive is an antioxidant, reduction of the residual free radicals caused by radiation may not be necessary for oxidation resistance.

In some of the lower molecular weight and lower density polyethylenes, the residual free radicals may recombine with each other even at room temperature over short periods of time, for example, few hours to few days, to few months. In such cases, the subsequent melt-annealing may be omitted if the increased crystallinity and modulus resulting from the irradiation is preferred. Otherwise, the subsequent melt-annealing may be carried out to decrease the crystallinity and modulus. In the case where melt annealing is omitted, the irradiated preform can be directly machined into the final medical device. The subsequent melt-annealing may also be omitted if the polymer contains enough antioxidant to prevent oxidation in the long-term.

The reduction of free radicals to the point where there are substantially no detectable free radicals can be achieved by heating the polymer to above the melting point. The heating provides the molecules with sufficient mobility so as to eliminate the constraints derived from the crystals of the polymer, thereby allowing essentially all of the residual free radicals to recombine. Preferably, the polymer is heated to a temperature between the peak melting temperature (PMT) and 500° C., more preferably between about 3° C. above PMT and 500° C., more preferably between about 10° C. above PMT and 50° C. above PMT, more preferably between about 10° C. and 12° C. above PMT and most preferably about 15° C. above PMT.

During melt annealing of UHMWPE, the polymer is heated to a temperature of about 137° C. to about 320° C., more preferably about 140° C. to about 320° C., more preferably yet about 140° C. to about 190° C., more preferably yet about 145° C. to about 300° C., more preferably yet about 145° C. to about 190° C., more preferably yet about 146° C. to about 190° C., and most preferably about 150° C. Preferably, the temperature in the heating step is maintained for about 0.5 minutes to about 24 hours, more preferably about 1 hour to about 3 hours, and most preferably about 2 hours. The heating can be carried out, for example, in air, in an inert gas, e.g., nitrogen, argon or helium, in a sensitizing atmosphere, for example, acetylene, or in a vacuum. It is preferred that for the longer heating times, that the heating be carried out in an inert gas or under vacuum to avoid in-depth oxidation.

In certain embodiments, there may be a tolerable level of residual free radicals in which case, the post-irradiation annealing can also be carried out below the melting point of the polymer. Alternatively, annealing below the melting point can be performed to reduce free radicals to undetectable levels by combination with mechanical deformation after irradiation or annealing under pressure at elevated temperature.

During below the melt annealing of UHMWPE, the polymer is heated to a temperature of about 70° C. to about 300° C., more preferably about 100° C. to about 135° C., more preferably yet about 120° C. to about 130° C., most preferably about 125° C. In cases where the temperature is above the melting temperature of the polymeric material at ambient pressure, the pressure may be increased to elevate the melting temperature and maintain the polymeric material below the melting temperature. Preferably, the temperature in the heating step is maintained for about 0.5 minutes to about 24 hours, more preferably about 1 hour to about 3 hours, and most preferably about 2 hours. The heating can be carried out, for example, in air, in an inert gas (e.g., nitrogen, argon or helium), in a sensitizing atmosphere (e.g., acetylene), or in a vacuum. It is preferred that for the longer heating times, that the heating be carried out in an inert gas or under vacuum to avoid in-depth oxidation.

(iii) Sequential Irradiation:

The polymer is irradiated in a sequential manner. With e-beam the irradiation is carried out with multiple passes under the beam and with gamma radiation the irradiation is carried out in multiple passes through the gamma source. Optionally, the polymer is thermally treated in between each or some of the irradiation passes. The thermal treatment can be annealing below the melting point, at the melting point or above the melting point of the polymer of the polymer. The irradiation at any of the steps can be warm irradiation, cold irradiation, or melt irradiation, as described above. For example the polymer is irradiated with 30 kGy at each step of the cross-linking and it is first heated to about 120° C. and then annealed at about 120° C. for about 5 hours after each irradiation cycle.

The term "blending" generally refers to mixing of a polyolefin in its pre-consolidated form with an additive. If both constituents are solid, blending can be done dry or by using a third component such as a liquid to mediate the mixing of the two components, after which the liquid is removed by evaporating ('solvent blending'). If the additive is liquid, for example α-tocopherol, then the solid can be mixed with large quantities of liquid, then diluted down to desired concentrations with the solid polymer to obtain uniformity in the blend. In the case where an additive is also an antioxidant, for example vitamin E, or α-tocopherol, then blended polymeric material is also antioxidant-doped. Polymeric material, as used herein, also applies to blends of a polyolefin and a plasticizing agent, for example a blend of UHMWPE resin powder blended with α-tocopherol and consolidated. Polymeric material, as used herein, also applies to blends of an additive, a polyolefin and a plasticizing agent, for example UHMWPE soaked in α-tocopherol.

In one embodiment, UHMWPE flakes are blended with α-tocopherol; preferably the UHMWPE/α-tocopherol blend is heated to diffuse the α-tocopherol into the flakes. The UHMWPE/α-tocopherol blend is further blended with virgin UHMWPE flakes to obtain a blend of UHMWPE flakes where some flakes are poor in α-tocopherol and others are rich in α-tocopherol. This blend is then consolidated and irradiated. During irradiation the α-tocopherol poor regions are more highly cross-linked than the α-tocopherol poor regions. Following irradiation the blend is homogenized to diffuse α-tocopherol from the α-tocopherol rich to α-tocopherol poor regions and achieve oxidative stability throughout the polymer.

The products and processes of this invention also apply to various types of polymeric materials, for example, any polypropylene, any polyamide, any polyether ketone, or any polyolefin, including high-density-polyethylene, low-density-polyethylene, linear-low-density-polyethylene, ultra-high molecular weight polyethylene (UHMWPE), copolymers or mixtures thereof. The products and processes of this invention also apply to various types of hydrogels, for example, poly(vinyl alcohol), poly(ethylene glycol), poly (ethylene oxide), poly(acrylic acid), poly(methacrylic acid), poly(acrylamide), copolymers or mixtures thereof, or copolymers or mixtures of these with any polyolefin. Polymeric materials, as used herein, also applies to polyethylene of various forms, for example, resin, powder, flakes, particles, powder, or a mixture thereof, or a consolidated form derived from any of the above. Polymeric materials, as used herein, also applies to hydrogels of various forms, for example, film, extrudate, flakes, particles, powder, or a mixture thereof, or a consolidated form derived from any of the above.

Blending of additives in the polymeric material resin can be done by: (i) dissolving one or more additive in a solvent or a mixture of solvents, (ii) mixing the polymer resin with the additive solution, and (iii) drying the solvent(s) by evaporation, optionally using elevated temperature or vacuum.

Solvents can be chosen from organic solvents such as acetic acid, acetone, acetonitrile, benzene, butanols, butanone, carbon tetrachloride, chlorobenzene, chloroform, cyclohexane, 1,2-dicholoethane, diethyl ether, diethylene glycol, diethylene glycol diethyl ether, 1,2-dimethoxyethane, dimethyl ether, dimethylformamide, dimethyl sulfoxide, dioxane, ethanol, ethyl acetate, ethylene glycol, glycerin, heptane, hexane, methanol, pentane, propanols, pyridine, tetrahydrofuran, toluene, xylene or they can be aqueous solvents. Aqueous solvents can be pure water or solution of other compounds such as acids, salts, or bases in water. They can be aqueous solutions of surfactants (generally amphiphilic compounds) such as fatty acids. They can also be inorganic non-aqueous solvents such as liquid alumina. The solvent can also be a supercritical fluid such as supercritical carbon dioxide.

The solvent is typically selected depending on the solubility of the additives desired to be blended into the polymer. The polymer resin can optionally dissolve in the same solvent. Different additives can be dissolved in different solvents and mixed together before mixing in the polymer or can be separately mixed with the polymer powder. In each case more than one solvent can be used. Dissolution of the additives can be enhanced or enabled by raising the temperature or pressure or raising the temperature and pressure such that the solvent is in the supercritical state.

The terms "about" or "approximately" in the context of numerical values and ranges refers to values or ranges that approximate or are close to the recited values or ranges such that the invention can perform as intended, such as utilizing a method parameter (e.g., time, dose, dose rate/level, and temperature), having a desired degree of cross-linking and/or a desired lack of or quenching of free radicals, as is apparent to the skilled person from the teachings contained herein. This is due, at least in part, to the varying properties of polymer compositions. Thus, these terms encompass values beyond those resulting from systematic error. These terms make explicit what is implicit, as known to the person skilled in the art.

The term 'extraction' refers to the removal of one or more components from the polymeric material. It can refer to the removal of an antioxidant from the surface of an antioxidant-blended polymeric material in powder, resin, flake form or in consolidated form.

The term 'surface' refers to region in the implant which is highly cross-linked after irradiation. Since, amount of cross-linking will depend on the concentration of antioxidant before irradiation, we can define surface in terms of FTIR index of antioxidant (or concentration) before irradiation. For example, 'surface' for vitamin E is defined as region in the implant where FTIR index is below 0.04.

'Bulk' is defined as a region with low cross-linking potential. Since, amount of cross-linking will depend on the concentration of anti-cross-linking agent or antioxidant before irradiation, we can define surface in terms of FTIR index of antioxidant (or concentration) before irradiation. For example, 'bulk' for vitamin E is defined as region in the implant where FTIR index is above 0.16 (approximately 1 wt %).

The term 'backside surface' is defined as the surface(s) or region(s) of a joint implant, which would be intended to be in contact with the inside of an acetabular shell, a tibial plate or in direct contact with the bone. It generally means the opposite side of the implant from the articular surface in contact with the joint space. Not all of the backside surface needs to be in contact with the shell, plate or bone or any other opposing surface. Sometimes, the backside surface can be also an articular surface, intended in the design of the implant or unintended because of loosening.

The term 'annealing below melt' refers to heating a polymer material to any temperature below 'melting point' and cooling down slowly down to room temperature.

The term 'melt annealing' refers to heating a polymer material to any temperature above 'melting point' and cooling down slowly to room temperature.

The term 'melting point' or 'melt' refers to the peak melting temperature of the polymeric material measured by a differential scanning calorimeter at a heating rate of 10° C. per minute when heating from −20° C. to 200° C. There may be melting of part of the polymeric material at temperatures below this temperature.

The term 'consolidation' refers generally to processes used to convert the polymeric material resin, particles, flakes, i.e. small pieces of polymeric material into a mechanically integral large-scale solid form, which can be further processed, by for example machining in obtaining articles of use such as medical implants. Methods such as injection molding, extrusion, compression molding, isostatic pressing (hot or cold), etc. can be used.

In the case of UHMWPE, consolidation is most often performed by "compression molding". In some instances consolidation can be interchangeably used with compression molding. The molding process generally involves: (i) heating the polymeric material to be molded, (ii) pressurizing the polymeric material while heated, (iii) maintaining the polymeric material at the temperature and pressure, and (iv) cooling down and releasing pressure.

Heating of the polymeric material can be done at any rate. Temperature can be increased linearly with time or in a step-wise fashion or at any other rate. Alternatively, the polymeric material can be placed in a pre-heated environment. The mold for the consolidation can be heated together or separately from the polymeric material to be molded. Steps (i) and (ii), i.e. heating and pressurizing before consolidation can be done in multiple steps and in any order. For example, a polymeric material can be pressurized at room temperature to a set pressure level 1, after which it can be heated and pressurized to another pressure level 2, which still may be different from the pressure or pressure(s) in step (iii). Step (iii), where a high temperature and pressure are maintained is the 'dwell period' where a major part of the consolidation takes place. One temperature and pressure or several temperatures and pressures can be used during this time without releasing pressure at any point. For example, dwell temperatures in the range of 135° C. to 350° C. and dwell pressures in the range of 0.1 MPa to 100 MPa or up to 1000 MPa can be used. The dwell time can be from 1 minute to 24 hours, more preferably from 2 minutes to 1 hour, most preferably about 10 minutes. The temperature(s) at step (iii) are termed 'dwell' or 'molding' temperature(s).

The pressure(s) used in step (iii) are termed 'dwell' or 'molding' pressure(s). The order of cooling and pressure release (step iv) can be used interchangeably. In some embodiments, the cooling and pressure release may follow varying rates independent of each other.

In some embodiments, the consolidated polymeric material is fabricated through "direct compression molding" (DCM), which is compression molding using parallel plates or any plate/mold geometry which can directly result in an implant or implant preform. Preforms are generally oversized versions of implants, where some machining of the preform can give the final implant shape.

Compression molding can also be done such that the polymeric material is directly compression molded onto a second surface, for example a metal or a porous metal to result in an implant or implant preform. This type of molding results in a "hybrid interlocked polymeric material" or "hybrid interlocked medical implant preform" or "hybrid interlocked medical implant". Molding is conducted with a metal piece that becomes an integral part of the consolidated polymeric article. For example, a combination of antioxidant-containing polyethylene resin, powder, or flake and virgin polyethylene resin, powder or flake is direct compression molded into a metallic acetabular cup or a tibial base plate. The porous tibial metal base plate is placed in the mold, antioxidant blended polymeric resin, powder, or flake is added on top. Prior to consolidation, the pores of the metal piece can be filled with a waxy or plaster substance through half the thickness to achieve polyethylene interlocking through the other unfilled half of the metallic piece. The pore filler is maintained through the processing and irradiation to prevent infusion of components in to the pores of the metal. In some embodiments, the article is machined after processing to shape an implant. Alternatively, in some embodiments, the porous metal can be used as an external doping source where it is filled with additive such as antioxidant(s) during high temperature exposure after consolidation into the hybrid interlocked medical implant preform. In some embodiments, there is more than one metal piece integral to the polymeric article. The metal(s) may be porous only in part or non-porous. In another embodiment, one or some or all of the metal pieces integral to the polymeric article is a porous metal piece that allows bone in-growth when implanted into the human body. In one embodiment, the porous metal of the implant is sealed using a sealant to prevent or reduce the infusion of additive/antioxidant (in diffusion steps after consolidation) into the pores during the selective doping of the implant. Preferably, the sealant is water soluble. But other sealants are also used. The final cleaning step that the implant is subjected to also removes the sealant. Alternatively, an additional sealant removal step is used. Such sealants as water, saline, aqueous solutions of water soluble polymers such as poly-vinyl alcohol, water soluble waxes, plaster of Paris, or others are used. In addition, a photoresist like SU-8, or other, may be cured within the pores of the porous metal component. Following processing, the sealant may be removed via an acid etch or a plasma etch.

Compression molding can also be done by "layered molding". This refers to consolidating a polymeric material by compression molding one or more of its resin forms, which may be in the form of flakes, powder, pellets or the like or consolidated forms in layers such that there are distinct regions in the consolidated form containing different concentrations of additives such as antioxidant(s). Whenever a layered-molded polymeric material is described in the examples below and is used in any of the embodiments it can be fabricated by:

- layered molding of polymeric resin powder or its additive blends where one or more layers contain additive and one or more layers contain one or more additives, or antioxidants of different or identical concentrations;
- molding together of previously molded layers of polymeric material containing different or identical concentration of additives such as antioxidant(s); or
- molding of UHMWPE resin powder with or without additive on to a at least one previously molded polymeric material with or without additive.

The layer or layers to be molded can be heated in liquid(s), in water, in air, in inert gas, in supercritical fluid(s) or in any environment containing a mixture of gases, liquids or supercritical fluids before pressurization. The layer or layers can be pressurized individually at room temperature or at an elevated temperature below the melting point or above the melting point before being molded together. The temperature at which the layer or layers are pre-heated can be the same or different from the molding or dwell temperature(s). The temperature can be gradually increased from pre-heat to mold temperature with or without pressure. The pressure to which the layers are exposed before molding can be gradually increased or increased and maintained at the same level.

During molding, different regions of the mold can be heated to different temperatures. The temperature and pressure can be maintained during molding for 1 second up to 1000 hours or longer. During cool-down under pressure, the pressure can be maintained at the molding pressure or increased or decreased. The cooling rate can be 0.0001° C./minute to 120° C./minute or higher. The cooling rate can be different for different regions of the mold. After cooling down to about room temperature, the mold can be kept under pressure for 1 second to 1000 hours. Or the pressure can be released partially or completely at an elevated temperature.

The term 'heating' refers to the thermal treatment of the polymer at or to a desired heating temperature. In one aspect, heating can be carried out at a rate of about 10° C. per minute to the desired heating temperature. In another aspect, the heating can be carried out at the desired heating temperature for a desired period of time. In other words, heated polymers can be continued to heat at the desired temperature, below or above the melting point, for a desired period of time. Heating time at or to a desired heating temperature can be at least 1 minute to 48 hours to several weeks long. In one aspect the heating time is about 1 hour to about 24 hours. In another aspect, the heating can be carried out for any time period as set forth herein, before or after irradiation. Heating temperature refers to the thermal condition for heating in accordance with the invention. Heating can be performed at any time in a process, including during, before and/or after irradiation. Heating can be done with a heating element. Other sources of energy include the environment and irradiation.

The term "high temperature exposure" refers to thermal treatment of the polymer or a starting material to a temperature between about 200° C. and about 500° C. or more, for example, temperature of about 200° C., about 250° C., about 280° C., about 300° C., about 320° C., about 350° C., about 380° C., about 400° C., about 420° C., about 450° C., about 480° C. or more. Heating time at "high temperature melting" can be at least 30 minutes to 48 hours to several weeks long. In one aspect the "high temperature melting" time is continued for about 1 minute to about 48 hours or more. For example, the heating is continued for at least for one minute, 10 minutes, 20 minutes, 30 minutes, one hour, two hours, five hours, ten hours, 24 hours, or more.

The term "annealing" refers to heating or a thermal treatment condition of the polymers in accordance with the invention. Annealing generally refers to continued heating of the polymers at a desired temperature below its peak melting point for a desired period of time, but in the invention refers to the thermal treatment of polymeric material at any desired temperature for a period of time. Annealing time can be at least 1 minute to several weeks long. In one aspect the annealing time is about 4 hours to about 48 hours, preferably 24 to 48 hours and more preferably about 24 hours. "Annealing temperature" refers to the thermal condition for annealing in accordance with the invention.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but are not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term 'sterile' refers to what is known in the art; to a condition of an object that is sufficiently free of biological contaminants and is sufficiently sterile to be medically acceptable, i.e., will not cause an infection or require revision surgery.

The term 'cross-linking' refers to what is known in the art as a processing method for polymeric materials comprising the chemically linking of parts of the polymeric material. Polymeric materials, for example, UHMWPE, can be cross-linked by a variety of approaches, including those employing cross-linking chemicals (such as peroxides and/or silane) and/or irradiation. Cross-linked UHMWPE can be obtained according to the teachings of U.S. Pat. No. 5,879,400, PCT/US99/16070, filed on Jul. 16, 1999, PCT/US97/02220, filed Feb. 11, 1997, U.S. Patent Application Publication No. 2003/0149125 (U.S. application Ser. No. 10/252,582), filed Sep. 24, 2002, and U.S. Pat. No. 6,641,617.

The term 'substantial cross-linking' refers to the state of a polymeric material with a cross-link density of 30 mol/m$^3$. The cross-link density is measured by swelling a roughly 3×3×3 mm cube of polymeric material in xylene. The samples are weighed before swelling in xylene at 130° C. for 2 hours and they are weighed immediately after swelling in xylene. The amount of xylene uptake is determined gravimetrically, then converted to volumetric uptake by dividing by the density of xylene; 0.75 g/cm$^3$. By assuming the density of polyethylene to be approximately 0.94 g/cm$^3$, the volumetric swell ratio of cross-linked UHMWPE was then determined. The cross-link density is calculated using the swell ratio as described in Oral et al., Biomaterials 31: 7051-7060 (2010) and is reported in mol/m$^3$. Thus, a substantially cross-linked polymeric material has a cross-link density of about 30 mol/m$^3$ in at least one part of the polymeric material. The term 'highly cross-linked' refers to the state of a polymeric material with a cross-link density of about 100 mol/m$^3$ in at least one part of the polymeric material. For example, an implant with surfaces having a cross-link density of about 250 mol/m³, and the bulk regions having a cross-link density of about 60 mol/m³ would be highly cross-linked.

The term 'antioxidant' refers to additives that protect the host polymer against oxidation under various aggressive environments, such as during high temperature consolidation, high temperature cross-linking, low temperature cross-linking, irradiation, etc. Antioxidants/free radical scavengers/anti-cross-linking agents can be chosen from but not limited to glutathione, lipoic acid, vitamins such as ascorbic acid (vitamin C), vitamin B, vitamin D, vitamin E, tocopherols (synthetic or natural, alpha-, gamma-, delta-), acetate vitamin esters, water soluble tocopherol derivatives, tocotrienols, water soluble tocotrienol derivatives; melatonin, carotenoids including various carotenes, lutein, pycnogenol, glycosides, trehalose, polyphenols and flavonoids, quercetin, lycopene, lutein, selenium, nitric oxide, curcuminoids, 2-hydroxytetronic acid; cannabinoids, synthetic antioxidants such as tertiary butyl hydroquinone, 6-amino-3-pyrodinoles, butylated hydroxyanisole, butylated hydroxytoluene, ethoxyquin, tannins, propyl gallate, other gallates, Aquanox family; Irganox® and Irganox® B families including Irganox® 1010, Irganox® 1076, Irganox® 1330, Irganox® 1035; Irgafos® family; phenolic compounds with different chain lengths, and different number of OH groups; enzymes with antioxidant properties such as superoxide dismutase, herbal or plant extracts with antioxidant properties such as St. John's Wort, green tea extract, grape seed extract, rosemary, oregano extract, mixtures, derivatives, analogues or conjugated forms of these. They can be primary antioxidants with reactive OH or NH groups such as hindered phenols or secondary aromatic amines, they can be secondary antioxidants such as organophosphorus compounds or thiosynergists, they can be multifunctional antioxidants, hydroxylamines, or carbon centered radical scavengers such as lactones or acrylated bis-phenols. The antioxidants can be selected individually or used in any combination. Also, antioxidants can be used with in conjunction with other additives such as hydroperoxide decomposers.

Irganox®, as described herein refers to a family of antioxidants manufactured by Ciba Specialty Chemicals. Different antioxidants are given numbers following the Irganox® name, such as Irganox® 1010, Irganox® 1035, Irganox® 1076, Irganox® 1098, etc. Irgafos® refers to a family of processing stabilizers manufactured by Ciba Specialty Chemicals. Irganox® family has been expanded to include blends of different antioxidants with each other and with stabilizers from different families such as the Irgafos® family. These have been given different initials after the Irganox® name, for instance, the Irganox® HP family are synergistic combinations of phenolic antioxidants, secondary phosphate stabilizers and the lactone Irganox® HP-136. Similarly, there are Irganox® B (blends), Irganox® L (aminic), Irganox® E (with vitamin E), Irganox® ML, Irganox® MD families. Herein we discuss these antioxidants and stabilizers by their tradenames, but other chemicals with equivalent chemical structure and activity can be used. Addition, these chemicals can be used individually or in mixtures of any composition.

Polymeric material: "Polymeric materials" or "polymer" generally refers to what is known in the art as a macromolecule composed of chemically bonded repeating structural subunits. Polymeric materials include polyethylene, for example, ultrahigh molecular weight polyethylene (UHMWPE). Ultra-high molecular weight polyethylene (UHMWPE) refers to linear substantially non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400, PCT/US99/16070, filed on Jul. 16, 1999, and PCT/US97/02220, filed Feb. 11, 1997. The term "polyethylene article" or "polymeric article" or "polymer" generally refers to articles comprising any "polymeric material" disclosed herein.

"Polymeric materials" or "polymers" can also include structural subunits different from each other. Such polymers can be di- or tri- or multiple unit-copolymers, alternating copolymers, star copolymers, brush polymers, grafted copolymers or interpenetrating polymers. They can be essentially solvent-free during processing and use such as thermoplastics or can include a large amount of solvent such as hydrogels. Polymeric materials also include synthetic polymers, natural polymers, blends and mixtures thereof. Polymeric materials also include degradable and non-degradable polymers.

"Polymeric materials" or "polymer" also include such as poly(vinyl alcohol), poly(acrylamide), poly(acrylic acid), poly(ethylene glycol), poly(ethylene oxide), blends thereof, or interpenetrating networks thereof, which can absorb water such that water constitutes at least 1 to 10,000% of their original weight, typically 100 wt % of their original weight or 99% or less of their weight after equilibration in water.

"Polymeric material" or "polymer" can be in the form of resin, flakes, powder, consolidated stock, implant, and can contain additives such as antioxidant(s). The "polymeric material" or "polymer" also can be a blend of one or more of different resin, flakes or powder containing different concentrations of an additive such as an antioxidant. The blending of resin, flakes or powder can be achieved by the blending techniques known in the art. The "polymeric material" also can be a consolidated stock of these blends.

'Blending' generally refers to mixing of a polymeric material in its pre-consolidated form with an additive. If both constituents are solid, blending can be done by using other component(s) such as a liquid to mediate the mixing of the two components, after which the liquid is removed by evaporating. If the additive is liquid, for example, α-tocopherol, then the polymeric material can be mixed with large quantities of liquid. This high concentration blend can be diluted down to desired concentrations with the addition of lower concentration blends or virgin polymeric material without the additive to obtain the desired concentration blend. This technique also results in improved uniformity of the distribution of the additive in the polymeric material. In the case where an additive is also an antioxidant, for example vitamin E, or α-tocopherol, then blended polymeric material is also antioxidant-doped. Polymeric material, as used herein, also applies to blends of a polyolefin and a cross-linking agent, for example a blend of UHMWPE resin powder blended with peroxide(s) and consolidated. Polymeric material, as used herein, also applies to blends of antioxidant (s), polyolefin(s) and cross-linking agent(s).

The products and processes of this invention also apply to various types of polymeric materials, for example, any polypropylene, any polyamide, any polyether ketone, or any polyolefin, including high-density-polyethylene, low-density-polyethylene, linear-low-density-polyethylene, ultra-high molecular weight polyethylene (UHMWPE), copolymers or mixtures thereof. The products and processes of this invention also apply to various types of hydrogel-forming polymers, for example, poly(vinyl alcohol), poly(vinyl acetate), poly(ethylene glycol), poly(ethylene oxide), poly (acrylic acid), poly(methacrylic acid), poly(acrylamide), copolymers or mixtures thereof, or copolymers or mixtures of these with any polyolefin. Polymeric materials, as used herein, also applies to polyethylene of various forms, for example, resin, powder, flakes, particles, powder, or a mixture thereof, or a consolidated form derived from any of the above. Polymeric materials, as used herein, also applies to hydrogels of various forms, for example, film, extrudate, flakes, particles, powder, or a mixture thereof, or a consolidated form derived from any of the above.

The term "additive" refers to any material that can be added to a base polymer in less than 50 v/v %. This material can be an organic or inorganic material with a molecular weight less than that of the base polymer. An additive can impart different properties to the polymeric material, for example, it can be a cross-linking agent or an antioxidant.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example. The term "permanent device" refers to what is known in the art that is intended for implantation in the body for a period longer than several months. Permanent devices include medical devices, for example, acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, and vascular grafts. The term "medical implant" refers to what is known in the art as a device intended for implantation in animals or humans for short or long term use. The medical implants, according to an aspect of the invention, comprises medical devices including acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, vascular grafts.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but are not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term "annealing" refers to heating or a thermal treatment condition of the polymers in accordance with the invention. Annealing generally refers to continued heating of the polymers at a desired temperature below its peak melting point for a desired period of time, but in the invention refers to the thermal treatment of polymeric material at any desired temperature for a period of time. Annealing time can be at least 1 minute to several weeks long. In one aspect the annealing time is about 4 hours to about 48 hours, preferably 24 to 48 hours and more preferably about 24 hours. "Annealing temperature" refers to the thermal condition for annealing in accordance with the invention.

The term 'heating' refers to the thermal treatment of the polymer at or to a desired heating temperature. In one aspect, heating can be carried out at a rate of about 10° C. per minute to the desired heating temperature. In another aspect, the heating can be carried out at the desired heating temperature for a desired period of time. In other words, heated polymers can be continued to heat at the desired temperature, below or above the melting point, for a desired period of time. Heating time at or to a desired heating temperature can be at least 1 minute to 48 hours to several weeks long. In one aspect the heating time is about 1 hour to about 24 hours. In another aspect, the heating can be carried out for any time period as set forth herein, before or after irradiation. Heating temperature refers to the thermal condition for heating in accordance with the invention. Heating can be performed at any time in a process, including during, before and/or after irradiation. Heating can be done with a heating element. Other sources of energy include the environment and irradiation.

The term 'sterile' refers to what is known in the art; to a condition of an object that is sufficiently free of biological contaminants and is sufficiently sterile to be medically acceptable, i.e., will not cause an infection or require revision surgery.

Cross-linking: Polymeric Materials, for example, UHMWPE can be cross-linked by a variety of approaches, including those employing cross-linking chemicals (such as peroxides and/or silane) and/or irradiation. Cross-linked UHMWPE can be obtained according to the teachings of U.S. Pat. No. 5,879,400, PCT/US99/16070, filed on Jul. 16, 1999, PCT/US97/02220, filed Feb. 11, 1997, U.S. Patent Application Publication No. 2003/0149125 (U.S. application Ser. No. 10/252,582), filed Sep. 24, 2002, and U.S. Pat. No. 6,641,617, the entirety of which are hereby incorporated by reference.

The term 'masking' refers to covering of one or more surface(s) or regions within surface(s) during any of the processes described herein. Generally, masking involves bringing the polymeric material, medical implant preform or medical implant in contact with a masking material. Masking area could be anywhere from 0% to 99% of the total surface area of any of the surface(s). Parts of the same surface, for example articular surface, can be masked. In any of the embodiments, material used for masking could be any material whose dimensional change upon heating for high temperature exposure is small. Preferably, the masking material does not melt below or at the temperature used during high temperature exposure. If the masking material melts, it preferably does not exude or leach any parts into the polymeric material being masked. Examples of such materials can be metals such as aluminum, copper, iron or any other material which fits this description. The masking material can be of any practically feasible thickness, from 1 microns to 1 meter, preferably 100 microns to 500 microns. Masking materials can be continuous or multiple masks of different materials and shapes and thicknesses can be used simultaneously. For example, medical implant preforms can be seated on a metal bar with conforming surfaces and simultaneously several masks can be used to cover parts of the rim and locking mechanisms while being exposed to high temperature. Depending on the thickness and material used, masks can be flexible, pliable or rigid.

The term "toughness" of a material refers to its ability to distribute an applied stress such that failure does not occur until there are very high stresses. It is quantified by the area under the stress-strain curve of a material. For example, a higher work-to-failure, which is the area under the engineering stress-strain curve obtained from tensile mechanical testing, is attributed directly to increased toughness. For example, toughness also refers to impact toughness, which is the work-to-failure as measured by impact testing. In the examples, this is demonstrated by IZOD impact testing according to ASTM F648.

The term 'fatigue strength' refers to the resistance of a material to crack formation under cyclic stresses for a prolonged period of time under stress levels lower than its yield strength. It is often characterized by fatigue crack propagation resistance as described, for example in ASTM E647.

The term "doping" refers to a process known in the art (see, for example, U.S. Pat. Nos. 6,448,315 and 5,827,904). In this connection, doping generally refers to contacting a polymeric material with a component or the solution/emulsion of a component under certain conditions, as set forth herein, for example, doping UHMWPE with an antioxidant under supercritical conditions. "Doping" also refers to introducing additive into the base polymeric material in quantities less than 50 v/v %. A polymeric material treated in such a way for example to incorporate an antioxidant is termed as an "antioxidant-doped" polymeric material. The polymeric material can be 'doped' by other additives as well, such as a cross-linking agent, in which case the polymeric material treated in such a way may be termed as 'cross-linking agent-doped'.

Doping may also be done by diffusing an additive into the polymeric material by immersing the polymeric material, by contacting the polymeric material with the additive in the solid state, or with a bath of the additive in the liquid state, or with a mixture of the additive in one or more solvents in solution, emulsion, suspension, slurry, aerosol form or in a gas or in a supercritical fluid. The doping process by diffusion can involve contacting a polymeric material, medical implant or device with an additive, such as vitamin E, for about an hour up to several days, preferably for about one hour to 24 hours, more preferably for one hour to 16 hours. The environment for the diffusion of the additive (bath, solution, emulsion, paste, slurry and the like) can be heated to room temperature or up to about 200° C. and the doping can be carried out at room temperature or up to about 200° C. Preferably, the antioxidant can be heated to 100° C. and the doping is carried out at 100° C. A polymeric material incorporated with an additive by diffusion in such a way is termed an 'additive-diffused' polymeric material. For example, a polymeric material immersed in a bath of antioxidant(s) for enough time to dope at least some parts of the polymeric material with the antioxidant(s), is termed an 'antioxidant-doped' or 'antioxidant-diffused' polymeric material.

To increase the depth of diffusion of the antioxidant, the material can be doped for longer durations, at higher temperatures, at higher pressures, and/or in presence of a supercritical fluid.

The doped polymeric material can be annealed by heating below or above the melting point of the polymeric material subsequent to doping. The annealing is preferably for about an hour up to several days, more preferably for about one hour to 24 hours, most preferably for one hour to 16 hours. The doped polymeric material can be heated to room temperature or up to about 350° C. and the annealing can be carried out at room temperature or up to about 350° C. Preferably, the doped polymeric material can be heated to 120° C. and the annealing is carried out at 120° C. Annealing can be performed in liquid(s), in air, in other gases such as oxygen, in inert gas, in supercritical fluid(s), or in vacuum. Annealing can also be performed in ambient pressure, above ambient pressure or below ambient pressure. Annealing can also be performed while the polymeric material is immersed in liquid antioxidant, such as vitamin E, or a solution/emulsion of antioxidant(s).

By "crystallinity" is meant the fraction of the polymer that is crystalline. The crystallinity is calculated by knowing the weight of the sample (w, in grams), the heat absorbed by the sample in melting (E, in J/g) and the heat of melting of polyethylene crystals ($\Delta H$=291 J/g), and using Equation 1 according to ASTM F2625 and the like or their successors:

$$\% \text{ Crystallinity} = E/w \times \Delta H \quad (\text{Eq. 1})$$

The invention is further illustrated in the following Examples which are presented for purposes of illustration and not of limitation.

EXAMPLES

Example 1

Surface Extraction of Vitamin E from Vitamin E-containing UHMWPE Pucks Using a Nitrogen Convection Oven A 5 wt % concentration mixture of vitamin E with UHMWPE (GUR 1050) was prepared by first mixing isopropyl alcohol (IPA) with vitamin E (Acros™ 99% D,L-α-tocopherol, DSM Nutritionals, NJ), then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E.

Two pucks (diameter 10 cm, thickness 1-1.1 cm) of the 1 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press (3895 Auto-M, Carver, Wabash, Ind.) where it was sintered, then compressed to 20 MPa at about 194° C. for 10 minutes, then cooled to room temperature under pressure. Then, the puck was cooled in approximately 1.5 hours under pressure.

Two pucks were placed on top of each other (to obtain a sample with double the effective diffusion distance from the surface) and masked with aluminum foil from 5 sides except one circular surface. They were placed in a pre-heated nitrogen convection oven at 290° C. with the unmasked surface exposed to nitrogen flow. The pucks were kept in the oven under these conditions for approximately 290 minutes. Samples were removed from the oven and were cooled in air at room temperature.

The sample was removed from the oven and cut at a distance far from the side walls near the center (FIG. 1) and the cut surface was microtomed to get a thin 150 micron film for Fourier Transform Infrared Spectroscopy (FTIR) analysis of vitamin E index. Spectra were collected in transmission with a resolution of 4 cm$^{-1}$ with an average of 32 scans. A vitamin E index was calculated by normalizing the area of the peak at 1260 cm$^{-1}$ (from 1226 cm$^{-1}$ to 1295 cm$^{-1}$) to the peak at 1895 cm$^{-1}$ (1850 cm$^{-1}$ to 1985 cm$^{-1}$). Vitamin E index plotted against depth of the sample is presented in FIG. 2. Here x=0 refers to the exposed surface available for extraction while x=20 refers to the masked surface in contact with the bottom surface of oven. Results are only presented for first 10 mm of the sample. The vitamin E index at and close to the surface was decreased, thereby creating a UHMWPE with a gradient in vitamin E concentration.

Example 2

Radiation Cross-linking of a Surface Extracted UHMWPE Containing Vitamin E

A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 0.75 wt % vitamin E.

Two pucks (diameter 10 cm, thickness 1-1.1 cm) of the 0.75 wt % vitamin E-containing UHMWPE blend were prepared via compression molding. The powder was preheated in a vacuum oven under partial vacuum/inert gas at 190-210° C. for approximately 2 hours. Then, the mold/powder was transferred to an automatic press (3895 Auto-M, Carver, Wabash, Ind.) where it was sintered, then compressed to 20 MPa at about 194° C. for 10 minutes, then cooled to room temperature under pressure. Then, the puck was cooled in approximately 1.5 hours under pressure.

Two pucks were placed on top of each other (to obtain a sample with double the effective diffusion distance from the surface) and masked with aluminum foil from 5 sides except one circular surface. They were placed in a pre-heated nitrogen convection oven at 290° C. with the unmasked surface exposed to nitrogen flow. The pucks were kept in the oven under these conditions for approximately 3.5 hours. Samples were removed from the oven and were cooled in air at room temperature.

After cooling down, the top puck was irradiated by electron beam irradiation using a Van-de-Graff generator at 3.0 MeV to a dose of 175 kGy at 25 kGy/pass.

Figure 3:
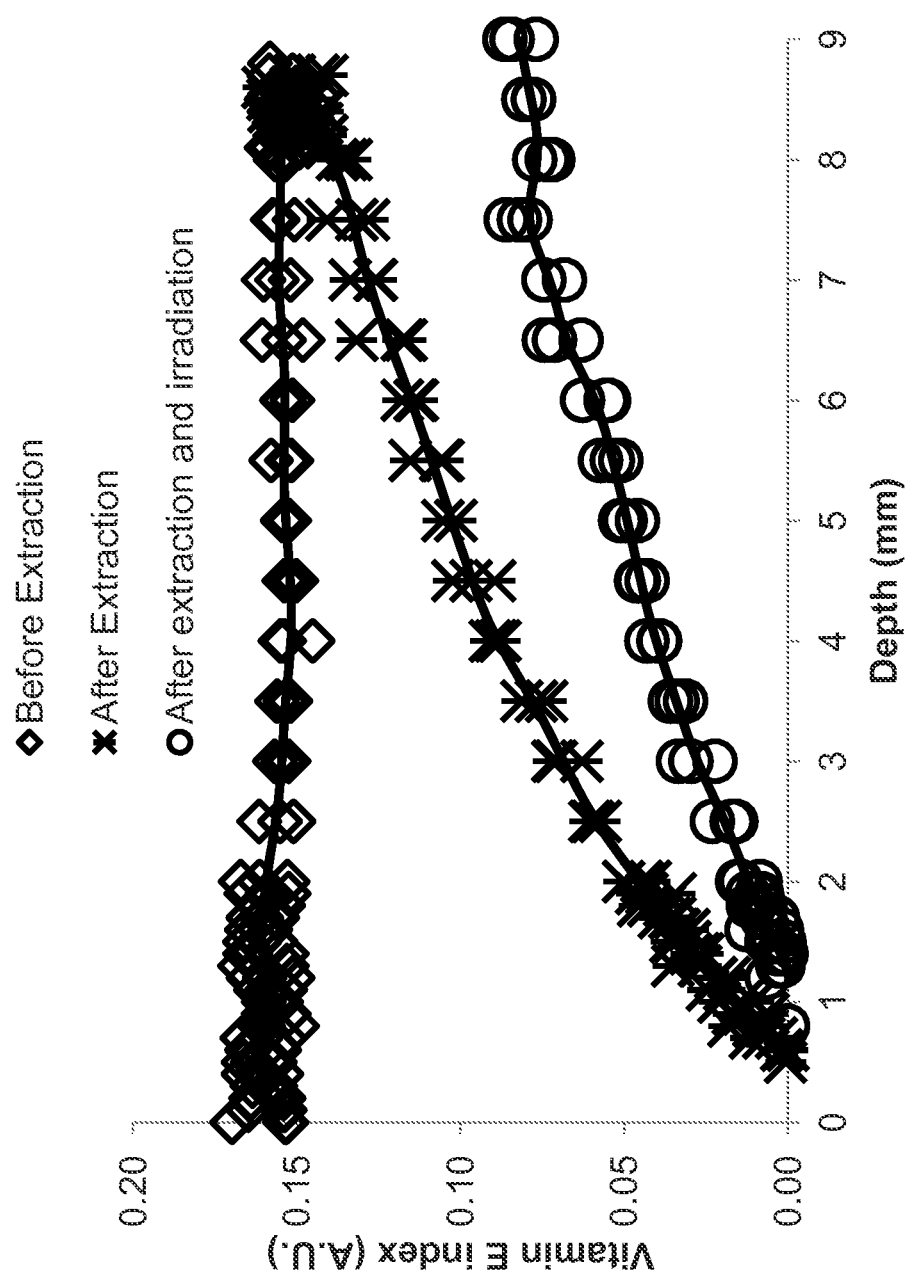
FIG. 3 is a vitamin E concentration profile of vitamin E-blended UHMWPE blocks extracted at high temperature at 290° C. for 290 minutes before and after irradiation at 175 kGy.

The vitamin E index as a function of depth is shown before and after irradiation in FIG. 3. The vitamin E index was decreased after irradiation and the vitamin E index at x=2 mm was below 0.04.

Figure 4:
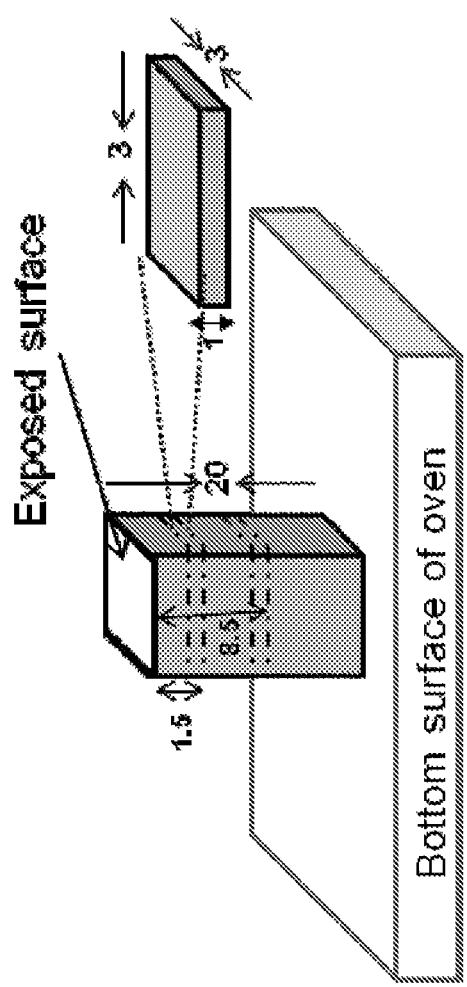
FIG. 4 is a schematic of how samples were obtained for cross-link density from the extracted and irradiated samples. Not drawn to scale—measurements in mm.)

The cross-link density of sections from the irradiated pucks was calculated. Samples (3×3×1 mm) were cut by razor blade as shown in FIG. 4. Samples were obtained at an approximate depth of 1.5 mm and 8.5 mm respectively from the extracted surface. The samples were swollen in xylene pre-heated to 130° C. for 2 hours. Weights of sample were measured before and after xylene swelling.

Cross-link density was calculated using Equation 2:

$$d_x = \frac{\ln(1 - q_{eq}^{-1}) + q_{eq}^{-1} X q_{eq}^{-2}}{\left(q_{eq}^{-\frac{1}{3}} - q_{eq}^{-2}\right)} \quad \text{(Eq. 2)}$$

where $$X = 0.33 + \frac{0.55}{q_{eq}}.$$

Volumetric equilibrium expansion ratio, $q_{eq}$, was calculated from weight swelling ratio using density of dry polyethylene as 0.94 g cm$^{-3}$ and that of xylene as 0.75 g cm$^{-3}$ at 130° C. The control was a virgin UHMWPE puck (diameter 10 cm, thickness 1.1 cm) prepared as described above and irradiated to 25 kGy. Cross-link density measurements were done for virgin material by extracting samples (3×3×1 mm) at approximately 1.5 mm and 8.5 mm from the exposed surface. Comparison of cross-link density at surface (1.5 mm) for virgin (80±10 mol/m$^3$) and surface extracted (210±10 mol/m$^3$) samples shows that the values much higher than conventional material.

Example 3

Optimal Wear Resistance at the Surface

A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain a vitamin E-blended GUR 1050 resin powder with 1 wt % vitamin E.

Two pucks (diameter 10 cm, thickness 1-1.1 cm) of the 1 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Two pucks were placed on top of each other (to obtain a sample with double the effective diffusion distance from the surface) and masked with aluminum foil from 5 sides except one circular surface. They were placed in a pre-heated nitrogen convection oven at 290° C. with the unmasked surface exposed to nitrogen flow. The pucks were kept in the oven under these conditions for approximately 3.5 hours. Samples were removed from the oven and were cooled in air at room temperature until steady state is reached.

Figure 5:
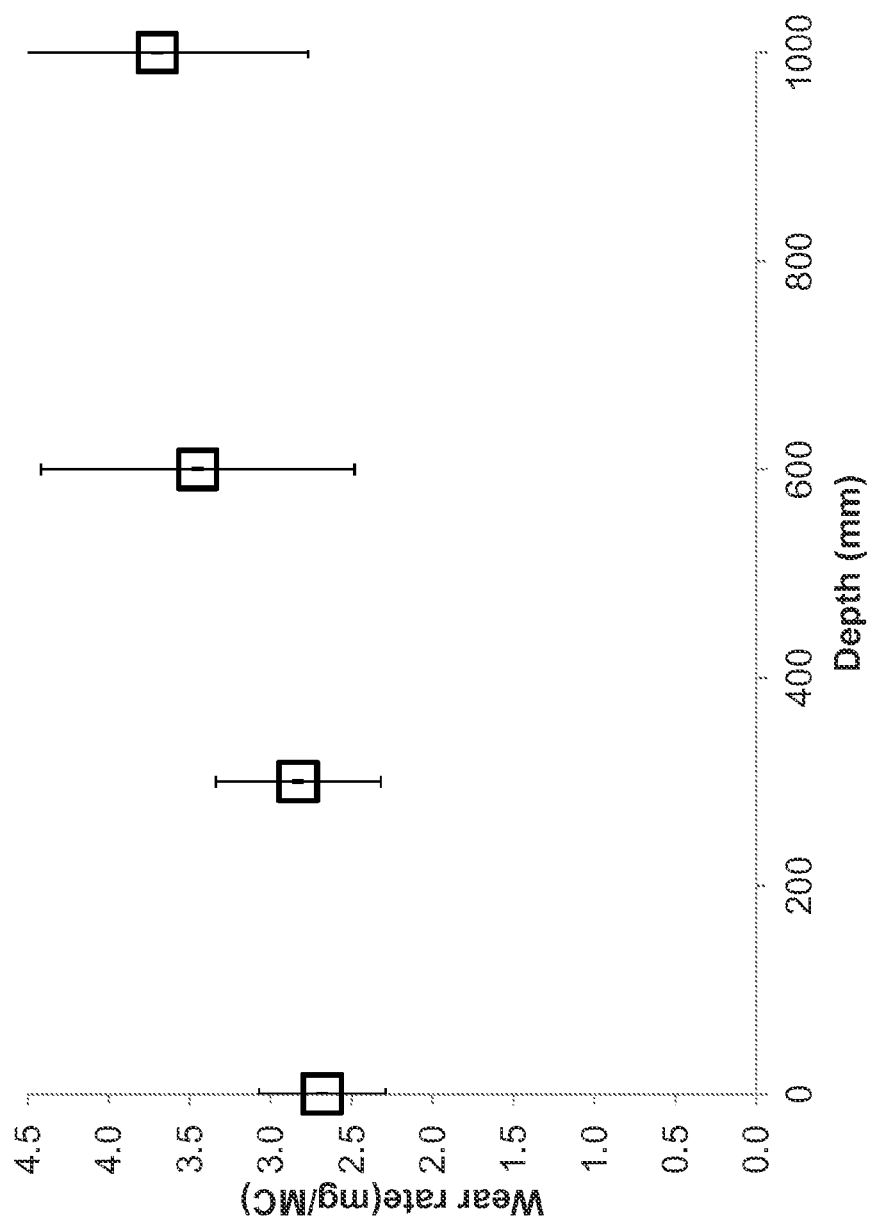
FIG. 5 is an average wear rate for first 1000 micron depth for extracted material irradiated to 175 kGy.

As specified earlier, cylindrical pins of 9 mm diameter and 9 mm length were machined from the top 10 mm of the material by machining off 1 mm from the exposed surface of multidirectional pin-on-disk wear test was conducted for the irradiated materials. Wear test was conducted for a week (approximately 1.1 million cycles). Pins were machined off 300 microns after 1 week of testing and wear rate testing was done. Similar procedure was repeated 3 times until we have reached 1000 micron away from the originally machined surface or 2 mm from the original surface. Pins were tested against CoCr in bovine serum at 2 Hz as previously described (Bragdon et al., "A new pin-on-disk wear testing method for simulating wear of polyethylene on cobalt-chrome alloy in total hip arthroplasty", J Arthroplasty, 2001 16(5): p. 658-65). Weight loss was measured approximately every 0.125 MC and wear rate is reported as a linear regression of weight loss versus number of cycles from 0.5 MC to 1 MC. Wear rate in mg/MC is plotted again depth of the material in FIG. 5. A similar procedure was followed for a virgin control irradiated to 25 kGy and wear rate was measured to be 8.2±1.3 mg/MC. The surface of the extracted sample had a much lower wear rate (p<0.01) as compared to the conventional material (virgin, 25kGy) even after 2 mm was machined off from the extracted and irradiated surface.

Example 4

Surface Extraction of Vitamin E from Vitamin E Containing Samples Through Vacuum Oven A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain blends with 0.75 or 2 wt % vitamin E.

Two pucks (diameter 10 cm, thickness 1-1.1 cm) of the 2 wt % and 0.75 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled over approximately 1.5 hours under pressure.

Figure 2:
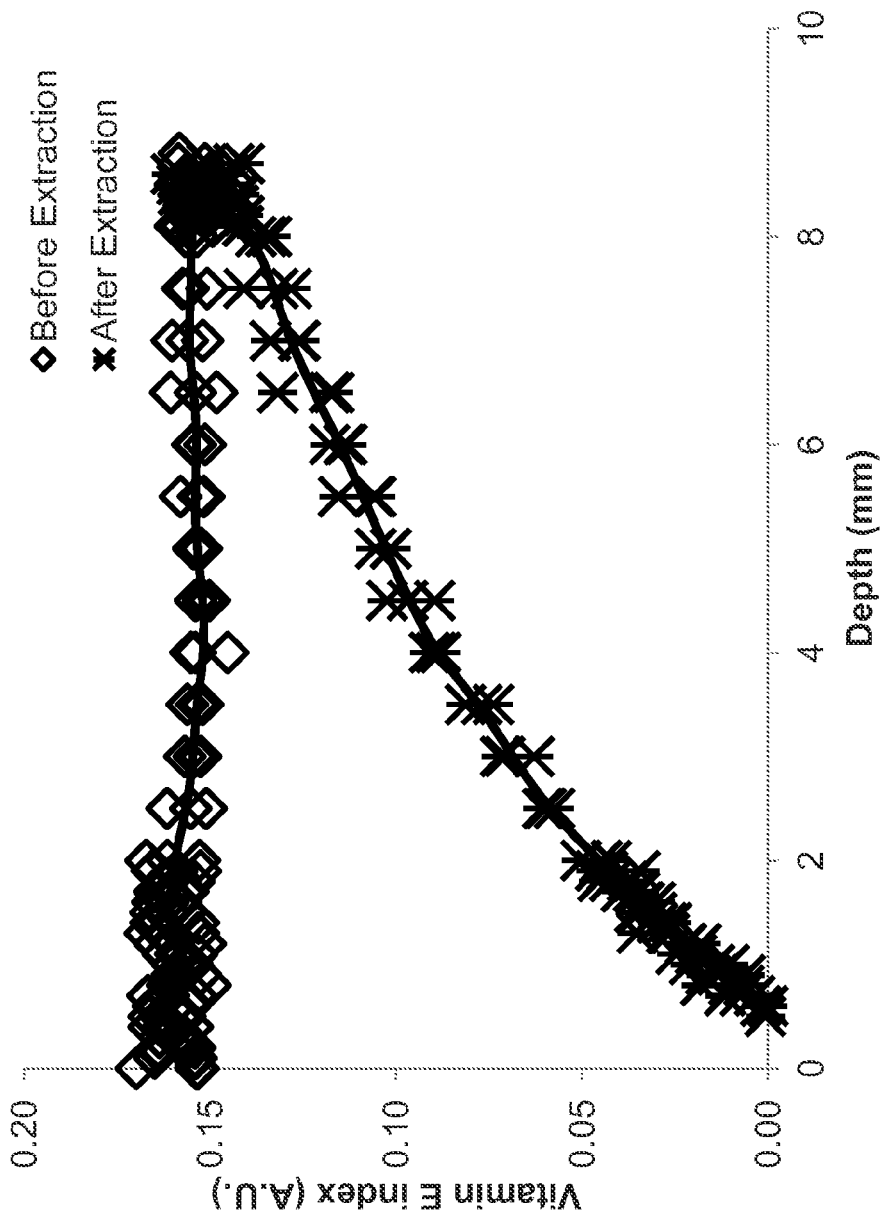
FIG. 2 is a vitamin E concentration profile from the surface towards the bulk of a UHMWPE block extracted at 290° C. for 290 minutes in a convection oven in nitrogen.
Figure 6:
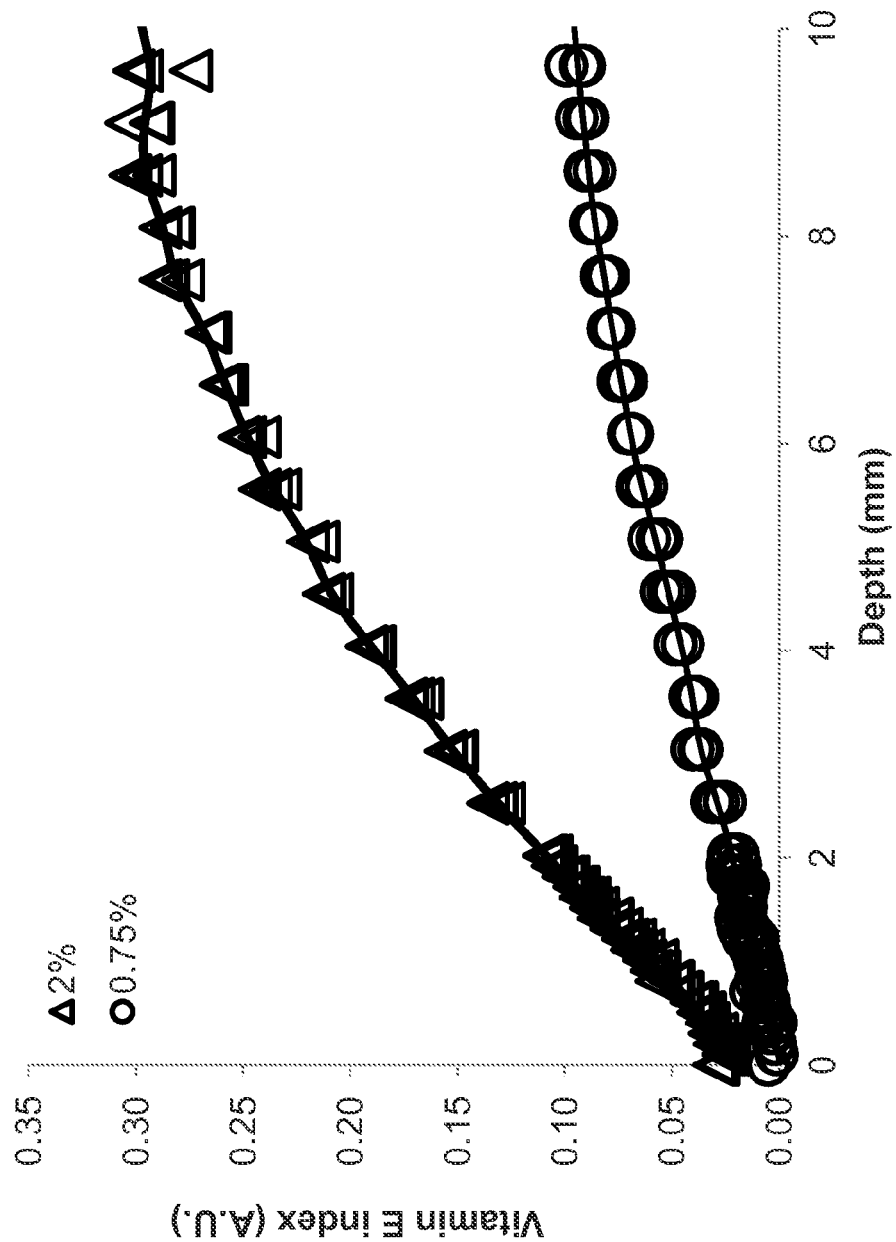
FIG. 6 is a vitamin E concentration profile of samples having initial concentration of 2% and 0.75% respectively, extracted in vacuum oven at 220° C. for 16 hours.

Cuboids (20×10×10 mm) were cut from these pucks and were masked with aluminum foil on 5 sides and kept in a vacuum oven at 220° C. for 16 hours. One 10×10 mm surface was left unexposed. Pressure in the vacuum oven was kept at $10^{-6}$ atm. Thereafter cubes were taken out from the oven and cooled in air at room temperature until steady state was reached. Cubes were cut from the center and 150 micron sections were microtomed to be used in FTIR analysis (FIG. 1). Vitamin E index was plotted as a function of depth in FIG. 6, where x=0 is the unmasked surface and x=20 is masked surface in contact with the surface of oven. Results are presented for the first 10 mm of the cuboid.

As evident from the plot, surface concentration of vitamin E was lower compared to bulk concentration of vitamin E. Therefore surface extraction of vitamin E can be achieved by high temperature exposure and in vacuum.

Example 5

Surface Extraction of Vitamin E from Vitamin E-containing by High Temperature Exposure in Air A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press (3895 Auto-M, Carver, Wabash, Ind.) where it was sintered, then compressed to 20 MPa at about 194° C. for 10 minutes, then cooled to room temperature under pressure. Then, the puck was cooled in approximately 1.5 hours under pressure.

Figure 7:
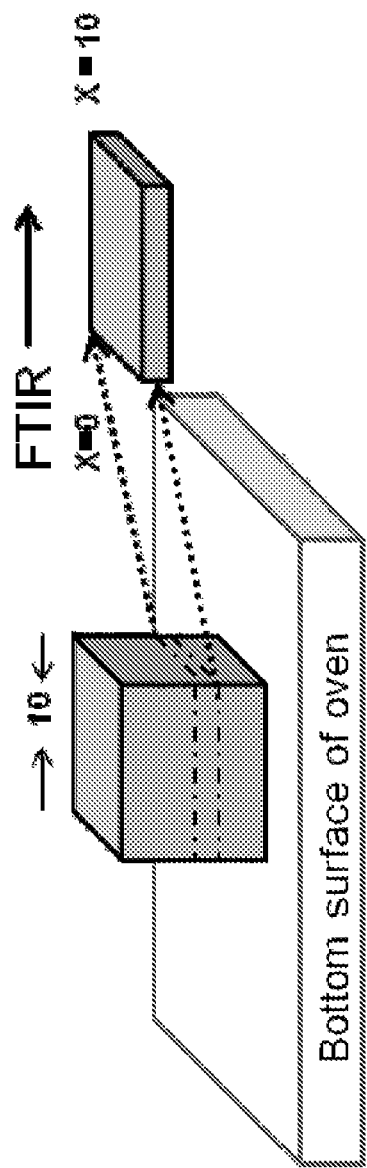
FIG. 7 is a schematic of surface extraction of vitamin E from vitamin E incorporated polymer block in an oven and microtomed sections obtained for FTIR (not drawn to scale—measurements in mm.).
Figure 8:
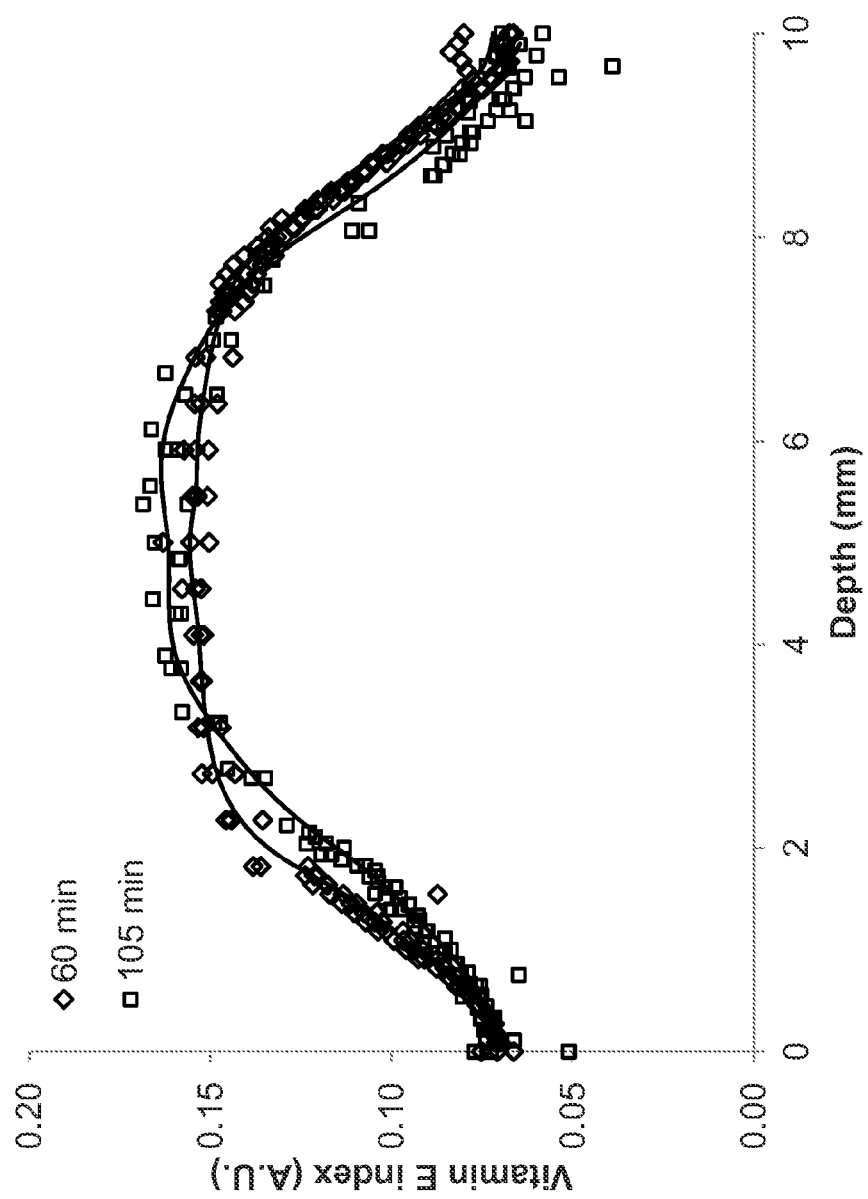
FIG. 8 is a vitamin E concentration profile of samples having initial concentration of 1 wt % vitamin E which were kept in an oven in air at 220° C. for 60 minutes and 105 minutes respectively.

Cubes machined from the puck (10 mm) were kept in an air oven on a metal mesh for 60 minutes and 105 minutes respectively. Thereafter, samples were cooled in air at room temperature until they reached a steady state. FTIR analysis was done by cutting the cube from the center and microtoming 150 micron sections from the center (FIG. 7). Vitamin E index as a function of depth inside the cube is shown in FIG. 8. Here x=0 refers to one side of the cube, while x=10 refers to an opposing side of the cube. The surface concentration of vitamin E was lower than the bulk for both 60 minutes and 105 minutes exposure times and the amount of extraction increased as the duration increased.

Example 6

Surface Extraction of Vitamin E from Vitamin E Containing Samples by Placing them in an Air Convection Oven at an Elevated Temperature A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 9:
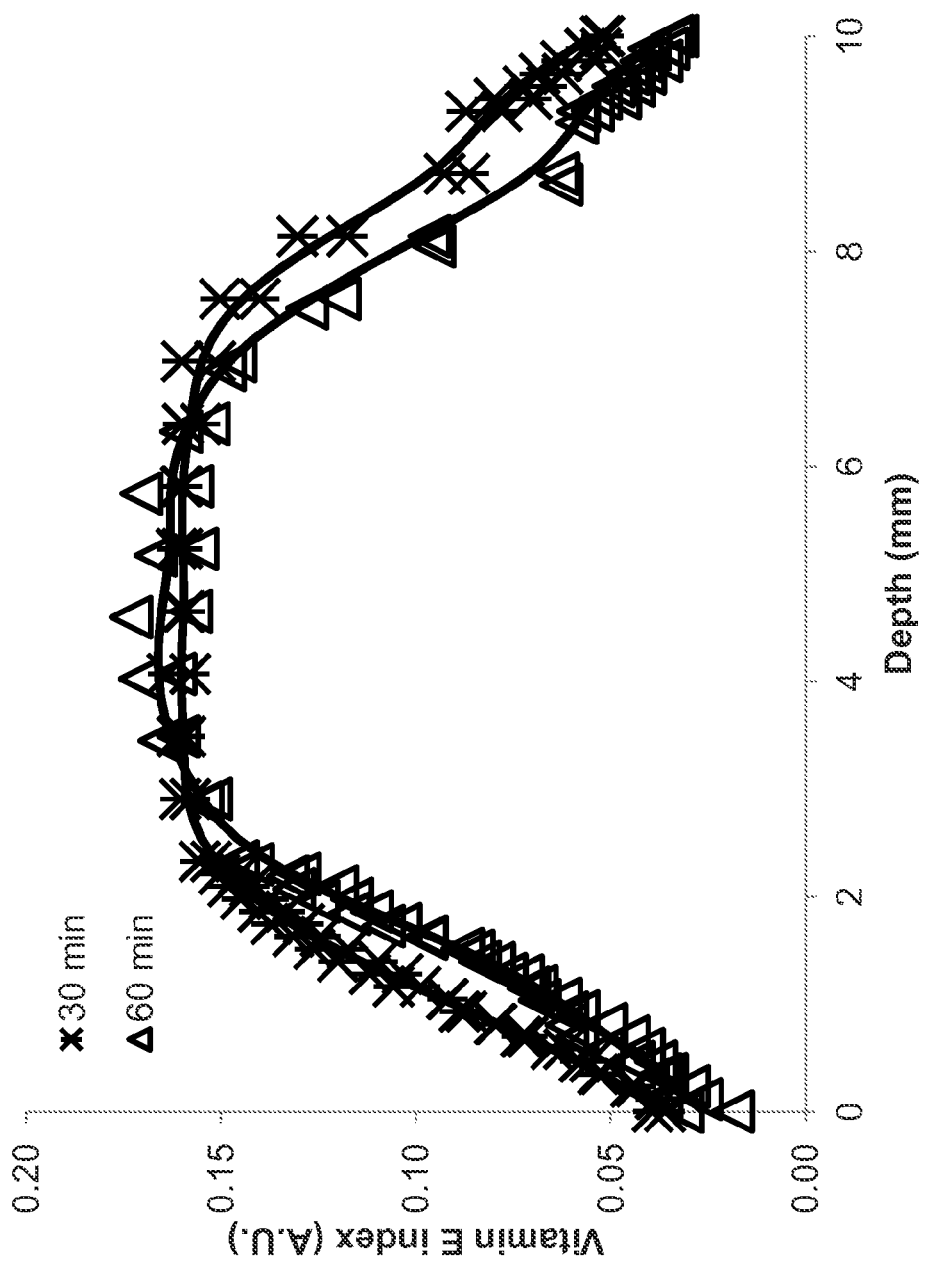
FIG. 9 is a vitamin E concentration profile of samples having initial concentration of 1% vitamin E which were kept in a convection oven in air at 220° C. for 30 minutes and 60 minutes respectively.

Two 1 cm cubes are machined from the puck and kept in an air convection oven at 220° C. for 30 minutes and 60 minutes respectively. Thereafter cubes were taken out and cooled at room temperature until steady state was reached. FTIR analysis was conducted on 150 micron sections that were microtomed from the center of the cube. The sections are parallel to the surface of the oven at x=0 refers to one side of the cube while x=10 refers to an opposing side of the same cube (FIG. 7). Referring to FIG. 9, results are plotted as a function of depth in the sample. Vitamin E index at the surface was low compared to the bulk suggesting that high temperature exposure in air is a viable method for extraction of vitamin E from vitamin E-blended UHMWPE.

Example 7

Manipulation of Vitamin E Profile by Changing Time in Nitrogen Convection Oven

A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C.

for approximately 2 hours. Then, the mold/powder was transferred to an automatic press where it was sintered, then compressed to 20 MPa at about 194° C. for 10 minutes, then cooled to room temperature under pressure. Then, the puck was cooled over approximately 1.5 hours under pressure.

Figure 10:
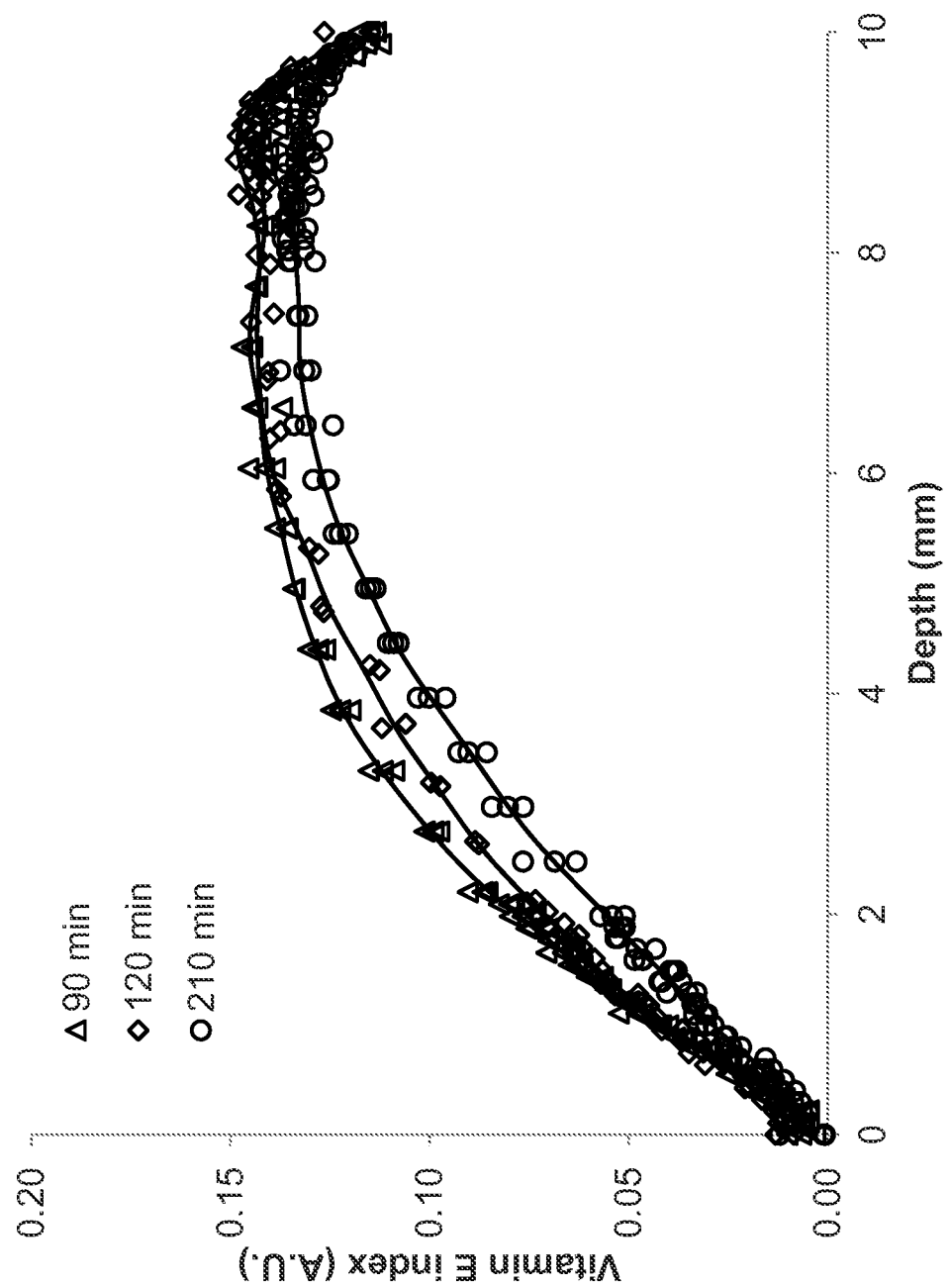
FIG. 10 is a vitamin E concentration profile of samples having initial concentration of 1% vitamin E which were kept in a convection oven in nitrogen at 290° C. for 90 minutes, 120 minutes and 210 minutes respectively.

Cubes (10×10×10 mm) were machined and masked with aluminum foil on 5 sides and kept in a nitrogen convection oven at a temperature of 290° C. Samples were kept for different durations namely—90 minutes, 120 minutes and 210 minutes, with the exposed surface in contact with nitrogen. Thereafter, cubes were cooled in air at room temperature until steady state was reached. FTIR analysis was carried out by cutting the cube from the center and scanning the surface perpendicular to the bottom surface of the oven, similar to the method described in FIG. 1 for a 20 mm cuboid. Vitamin E profile as a function of depth is plotted in FIG. 10. x=0 refers to the exposed surface in contact with nitrogen, while x=10 refers to the bottom surface, which was masked and in contact with bottom surface of oven. The amount of vitamin E extracted increased with increasing duration of high temperature exposure. Therefore, a desired vitamin E concentration profile could be obtained by manipulating extraction duration.

Example 8

Manipulation of Vitamin E Profile by Changing Extraction Duration in Vacuum Oven As illustrated earlier, vitamin E profile and thereby wear properties can be manipulated by changing the duration of high temperature exposure in nitrogen. A similar set of experiments to determine the effect of duration on concentration profile were conducted in vacuum.

A 5 wt % concentration mixture of vitamin E with UHMWPE (GUR 1050) was prepared by first mixing isopropyl alcohol (IPA) with vitamin E (D,L-α-tocopherol, DSM Nutritionals, Parsipanny, N.J.), then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was compressed to 20 MPa at about 194° C. for 10 minutes, then cooled to room temperature under pressure. Then, the puck was cooled in approximately 1.5 hours under pressure.

Figure 11:
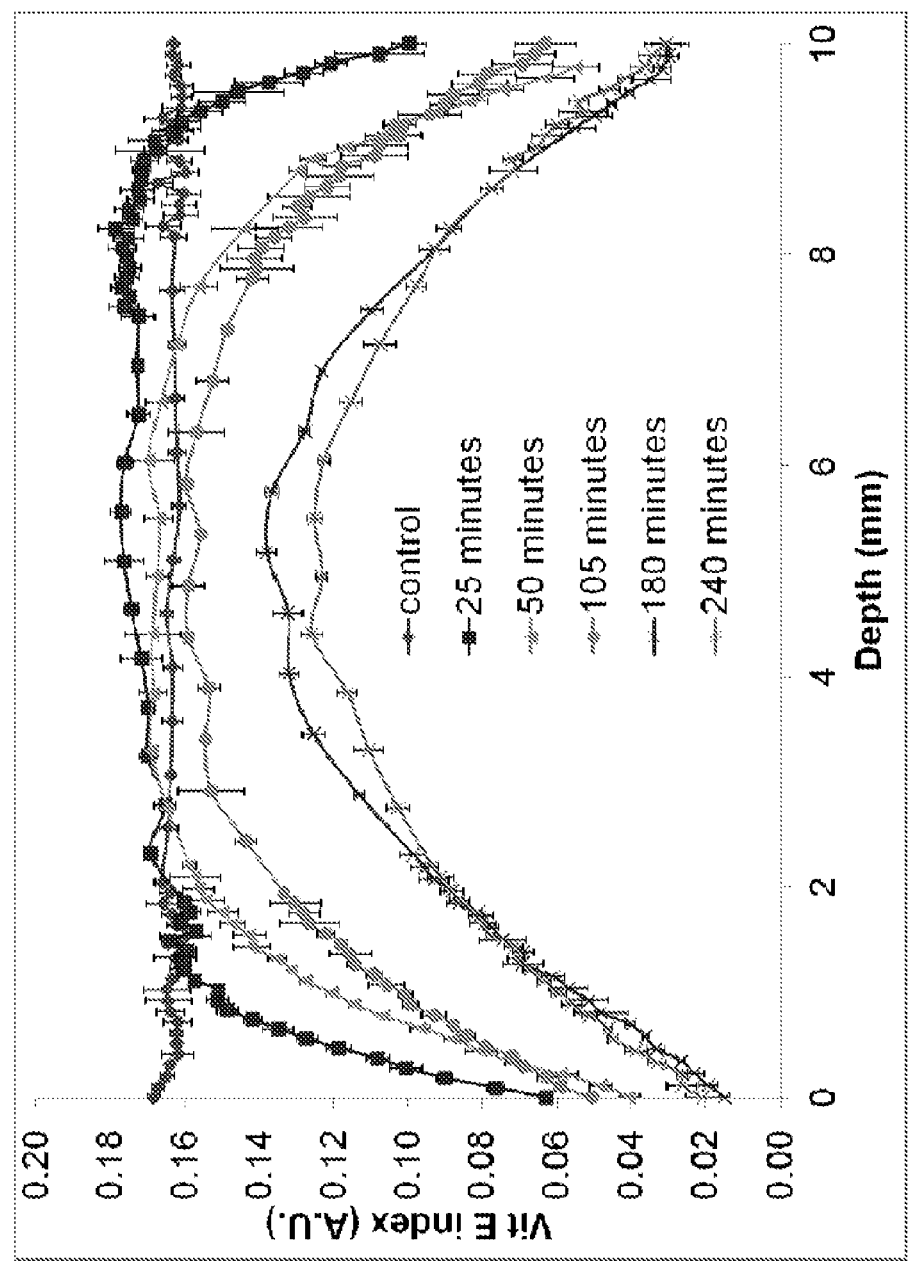
FIG. 11 shows vitamin E concentration profiles of 1 wt % vitamin E blended UHMWPE after exposure to 220° C. in vacuum ($2 \times 10^{-6}$ atm argon) for 25, 50, 105, 180 or 240 minutes.

Cubes (10 mm) were machined from 1 wt % vitamin E blended UHMWPE pucks and kept without masking on a metal mesh in a vacuum oven at 220° C. and a pressure of 2×10$^{-6}$ atm (argon) for 25 minutes, 50 minutes, 105 minutes, 180 minutes and 240 minutes. Cubes were removed after the respective time had elapsed and were then cooled in air at room temperature until steady state was reached. FTIR analysis was conducted on 150 micron sections cut from the center of the cube. Due to the fact that the cubes were unmasked, FTIR analysis was done on a surface which was cut from the center of the cube but was parallel to the bottom of the oven (FIG. 7). Results are plotted in FIG. 11, with x=0 referring one side surface of the cube and x=10 referring to the opposing side surface. The amount of vitamin E extracted from the surface increased with increasing high temperature exposure duration in vacuum; thereby a desired vitamin E profile in the sample could be obtained by manipulating extraction duration.

Example 9

Manipulation of Vitamin E Profile by Changing Temperature in Nitrogen Convection Oven A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled over approximately 1.5 hours under pressure.

Figure 12:
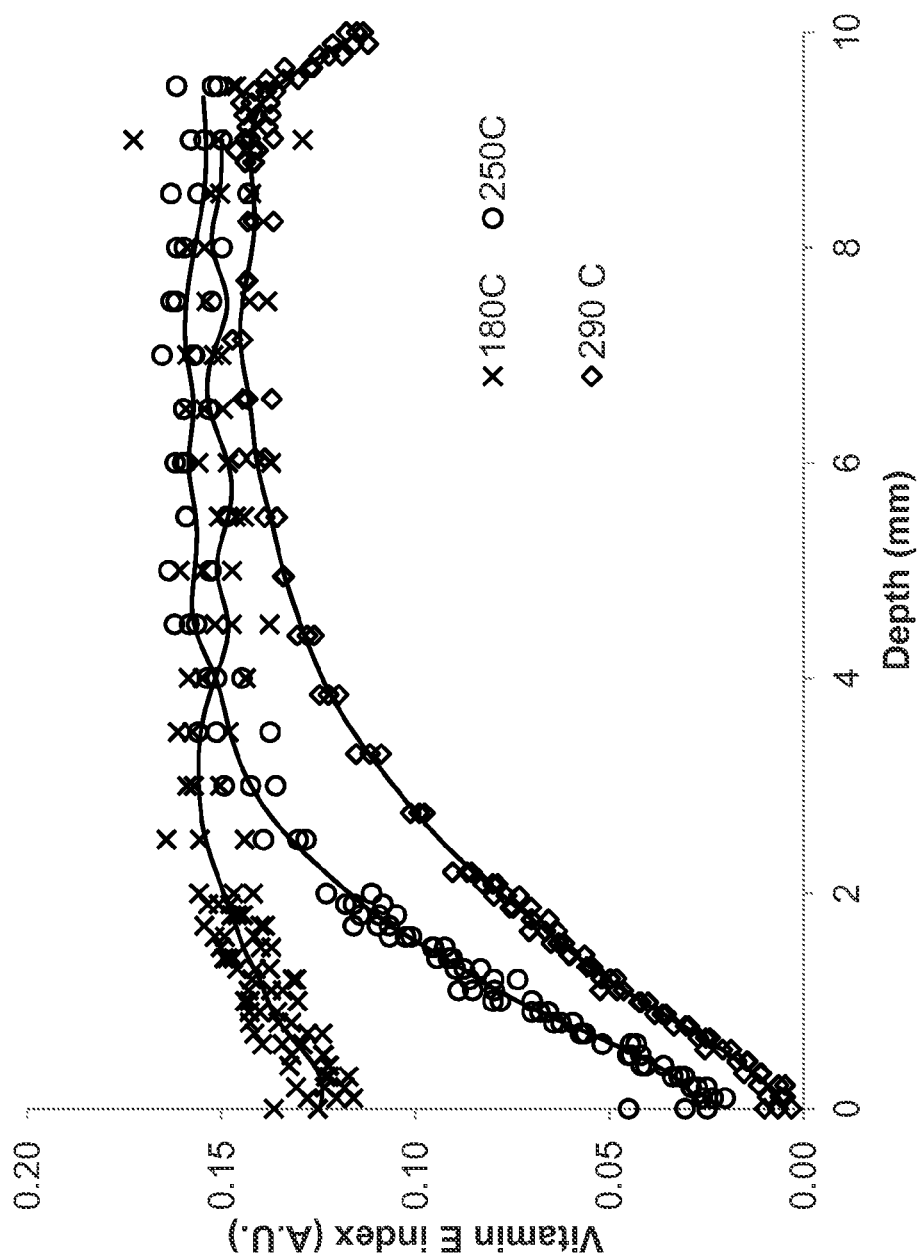
FIG. 12 shows vitamin E concentration profiles of 1 wt % blended UHMWPE after exposure to 180° C., 250° C. or 270° C. for 90 minutes.

Two cubes (10 mm) were machined and masked on 5 sides with aluminum foil before placing in a nitrogen convection oven for 90 minutes. Cubes were kept at temperatures of 180° C., 250° C. and 290° C. respectively. After 90 minutes, cubes were taken out and cooled at room temperature until steady state was reached. FTIR analysis was performed by cutting the sample from the center and microtoming a 150 micron section perpendicular to the bottom surface of the oven (FIG. 7). Vitamin E index was plotted against depth in FIG. 12. Here x=0 represented the exposed surface to nitrogen, while x=10 mm was the masked surface which was kept in contact with bottom surface of oven. As the temperature was increased in the nitrogen convection oven, the amount of extraction of vitamin E from the sample increased.

Example 10

Manipulation of Vitamin E Profile by Changing Exposure Temperature in Air

A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was compressed to 20 MPa at about 194° C. for 10 minutes, then cooled to room temperature under pressure. Then, the puck was cooled in approximately 1.5 hours under pressure.

Figure 13:
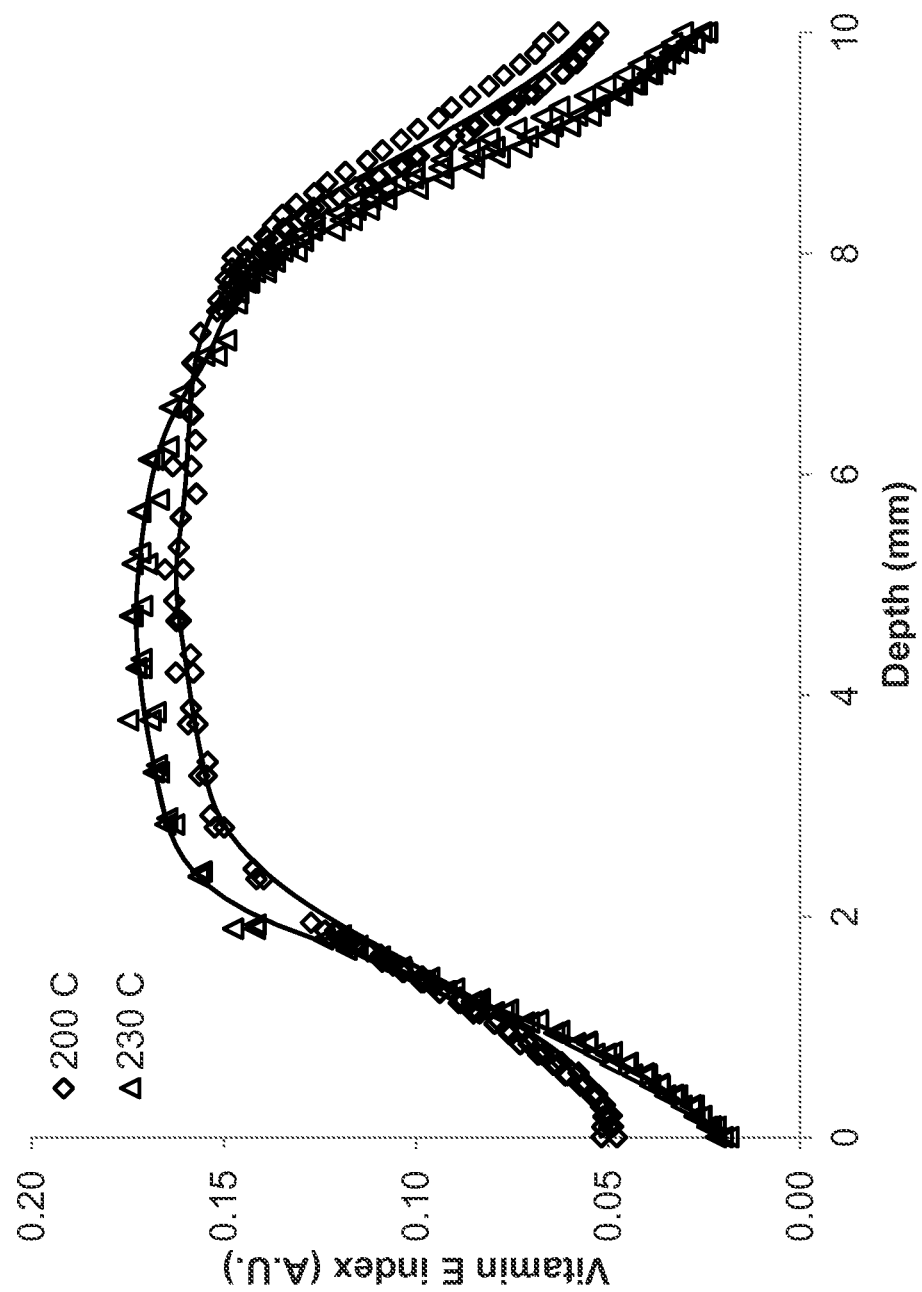
FIG. 13 shows vitamin E concentration profiles of 1 wt % vitamin E-blended UHMWPE after exposure to 200° C. or 230° C. for 60 minutes in air.

Two cubes (10×10×10 mm) were machined and placed in an air convection oven without masking for 60 minutes at temperatures of 200° C. or 230° C. Thereafter, samples were taken out of the oven and cooled in air at room temperature. FTIR analysis was done on cubes by cutting it from the center on a surface parallel to the oven (FIG. 7). Results are plotted as a function of depth in FIG. 13. Increasing temperature from 200° C. to 230° C. resulted in more extraction from the surface (2 mm.) without affecting the bulk concentration of vitamin E.

Example 11

Manipulation of Vitamin E Profile by Changing Initial Concentration of Vitamin E in the Sample A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 blends with 1 or 0.75 wt % vitamin E.

Figure 14:
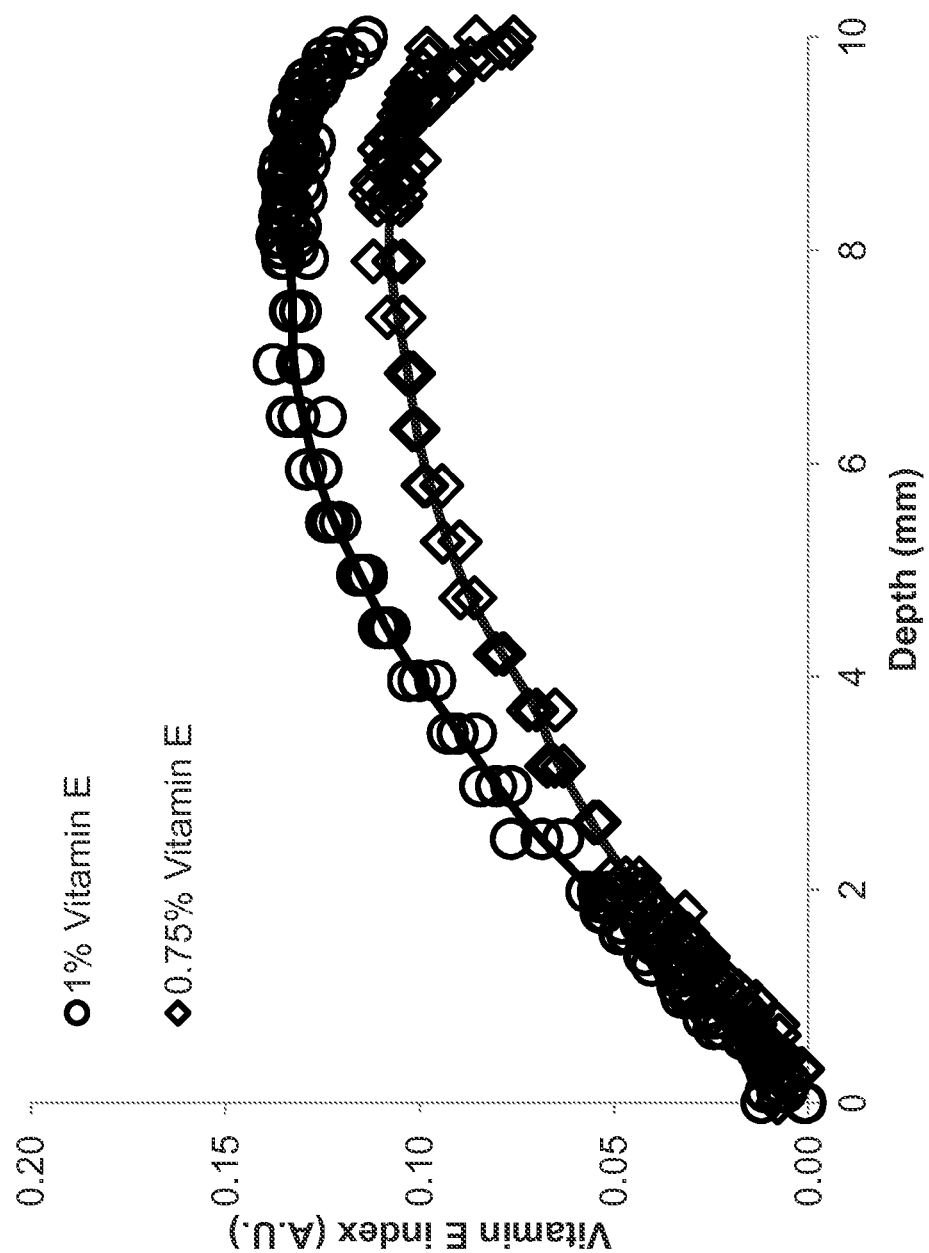
FIG. 14 shows vitamin E concentration profiles of 0.75 wt % and 1 wt % vitamin E-blended UHMWPE's exposed to 290° C. for 210 minutes in nitrogen.

Two pucks (diameter 10 cm, thickness 1-1.1 cm) of 1 wt % and 0.75 wt % vitamin E-containing UHMWPE blends were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure. Cubes (10×10×10 mm) were machined from these pucks and masked on 5 sides with aluminum foil and kept in an inert gas convection oven in nitrogen for 210 minutes. Thereafter, samples were taken out and cooled in air at room temperature until steady state was reached. Cubes were cut from the center and FTIR analysis was done on a 150 micron microtomed surface which was perpendicular to the bottom surface of the cube. Vitamin E profile as a function of depth in the sample is presented in FIG. 14. Here x=0 is the surface that was exposed to nitrogen while x=10 was the masked surface in contact with bottom surface of the oven (FIG. 1). Vitamin E concentration profile in the sample could be manipulated by changing its initial concentration in the sample.

Example 12

Manipulation of Vitamin E Concentration Profile by Changing the Masking Area

A 5 wt % concentration mixture of vitamin E with UHMWPE (GUR 1050) was prepared by first mixing isopropyl alcohol (IPA) with vitamin, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E concentration.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 15:
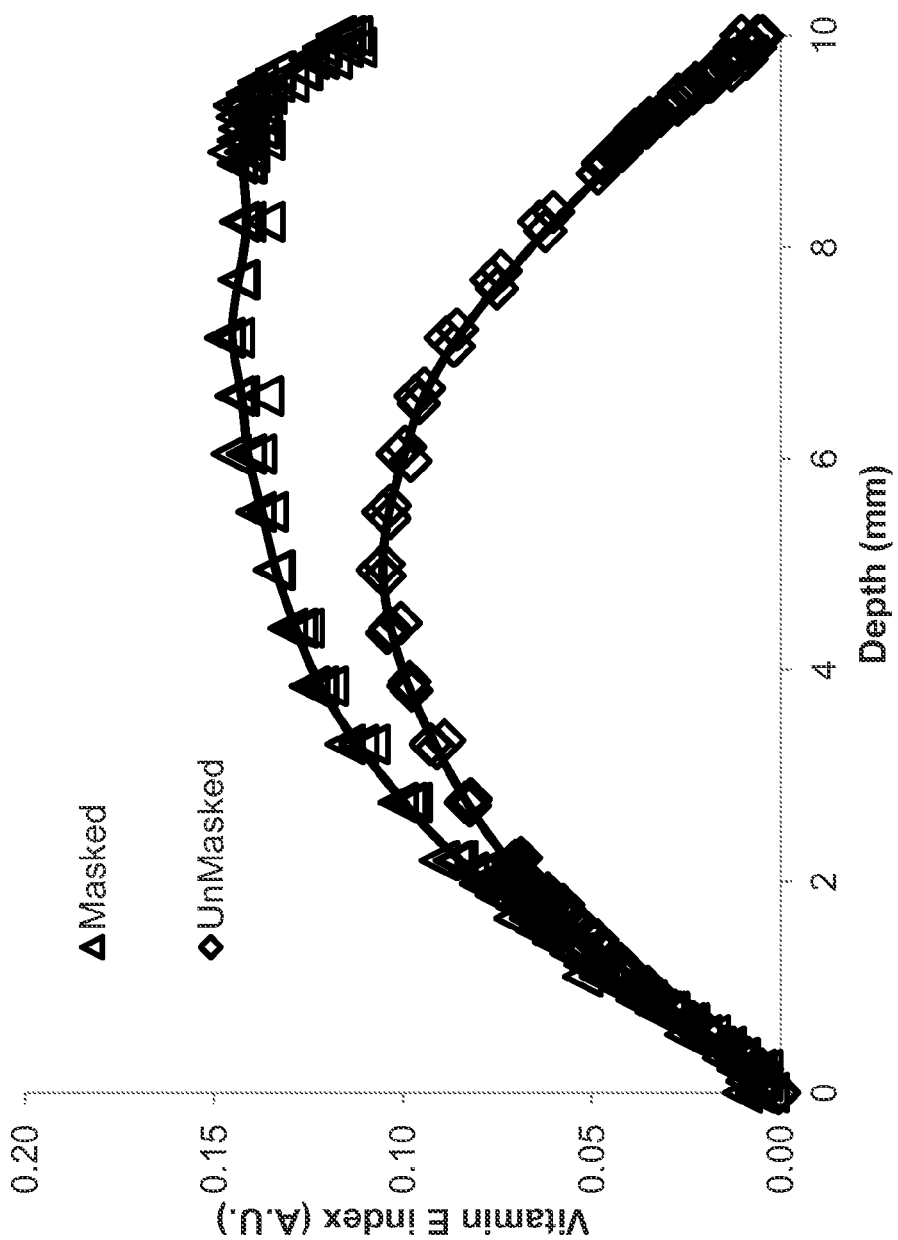
FIG. 15 shows vitamin E concentration profiles of 1 wt % vitamin E blended UHMWPE cubes exposed to 290° C. for 90 minutes without masking and with masking of all but one surface.

Two cubes (10×10×10 mm) were machined from these pucks. One of the cubes was masked with aluminum foil on 5 sides, leaving one side exposed, while the other cube was completely unmasked. The cubes were kept on a metal mesh in a nitrogen convection oven at 290° C. for 90 minutes, with the exposed side of the masked cube in contact with nitrogen convection. Thereafter, samples were taken out and cooled down in air at room temperature. The masked cube was analyzed by cutting it from the center and FTIR analysis was performed on a 150 micron microtomed surface perpendicular to the bottom surface of the cube using the method described for cuboids described in FIG. 1. The unmasked cube was analyzed by performing FTIR analysis on a 150 micron section cut from the center of the cube but parallel to the bottom surface of the oven. Vitamin E profile as a function of depth in the samples is presented in FIG. 15. Here x=0 was the surface which was exposed to nitrogen while x=10 was the masked surface in contact with bottom surface of the oven (FIG. 1). For unmasked samples, x=0 refers to one side surface of the cube and x=10 refers to the opposite side surface (FIG. 7). The results showed that the vitamin E concentration profile in the sample was significantly different for masked and unmasked samples and that masking prevented extraction of the vitamin E from the masked surfaces.

Example 13

Manipulation of Vitamin E Concentration Profile by Cyclic Heating and Cooling

A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E concentration.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 16:
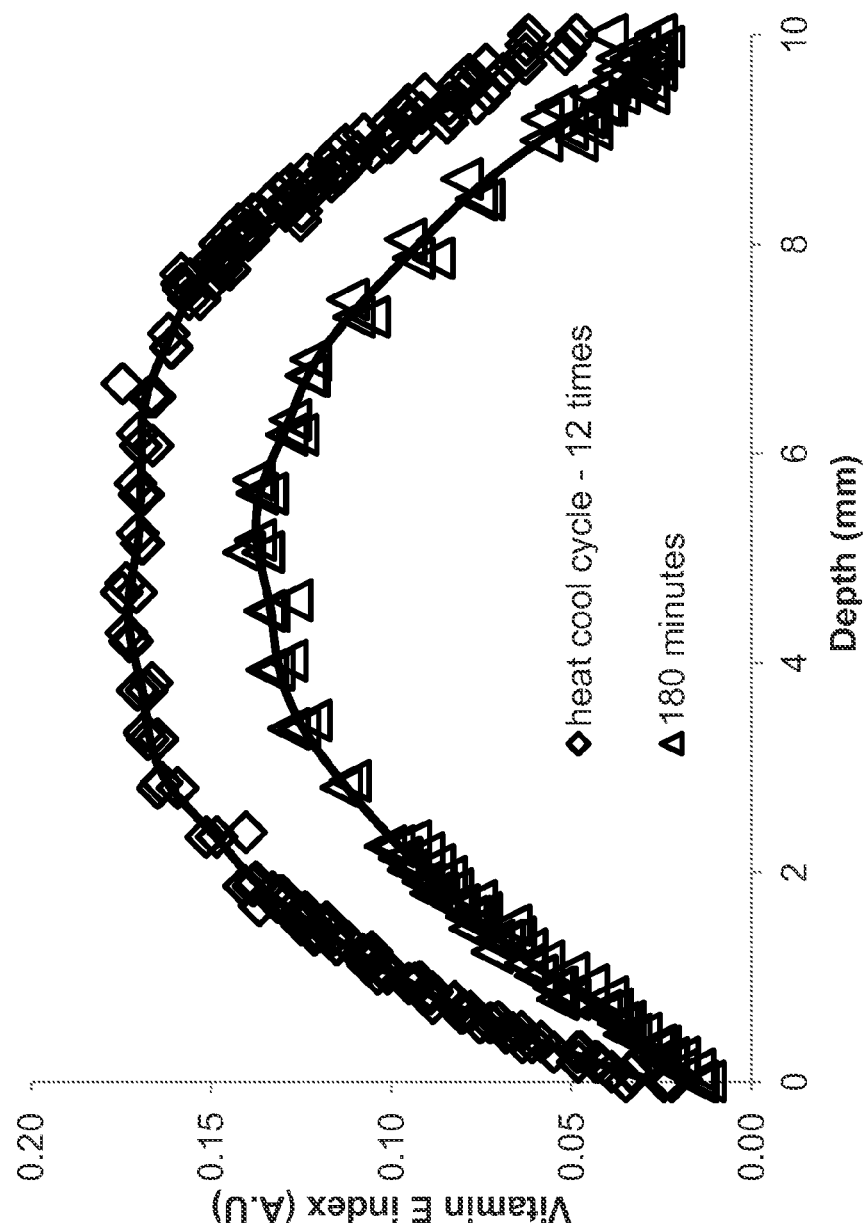
FIG. 16 is a vitamin E concentration profile of 1 wt % vitamin E-blended UHMWPE after exposure to 220° C. for 180 minutes continuous heating versus 180 minutes during 15 minute heating/3 minute cooling cycles.

Two cubes (10 mm) were machined from the puck and first was kept in a vacuum oven at a pressure of $2 \times 10^{-6}$ atm (argon) and at a temperature of 220° C. for 180 minutes. Thereafter, it was taken out of the oven and cooled to about room temperature. Another cube was kept in the vacuum oven at the same pressure and temperature but for 15 minutes. Thereafter, sample was taken out and cooled in water for 3 minutes. The complete heating/cooling cycle was repeated 12 times for a total heating time of 180 minutes. FTIR analysis was conducted on 150 micron sections obtained from the center of the cube and parallel to the bottom surface of the oven (FIG. 7). Results are presented for both the cubes in FIG. 16. The vitamin E concentration profile was different for these samples, which suggested that the vitamin E concentration profile could be manipulated by conducting a cyclic heating cooling treatment as compared to single heating cooling operation during high temperature extraction of vitamin E-blends.

Example 14

Manipulation of Vitamin E Profile by Treatment with Tween 20 Surfactant after Extraction in Ovens A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E concentration.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 17:
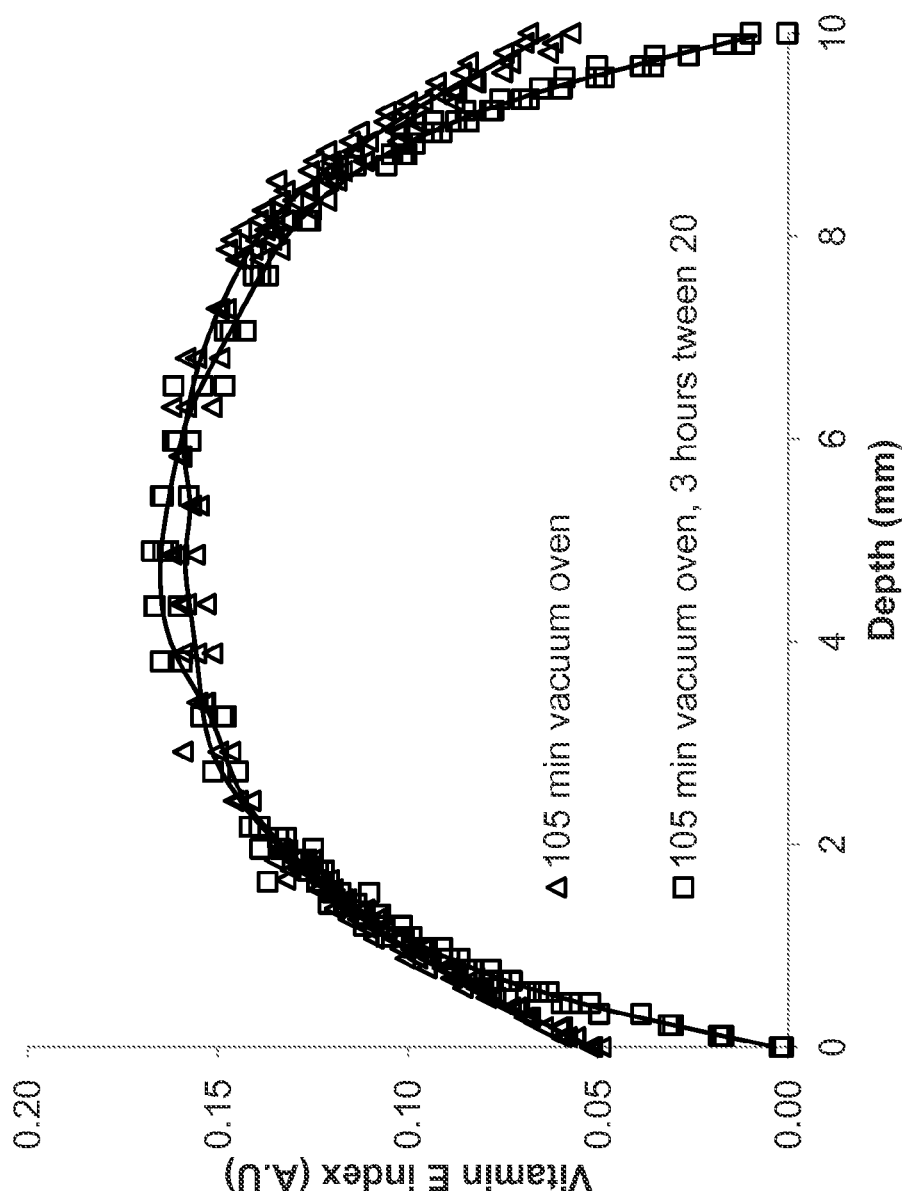
FIG. 17 is a vitamin E concentration profile of 1 wt % vitamin E blended UHMWPE after exposure to 220° C. in vacuum ($2\times10^{-6}$ atm argon) for 105 minutes and further extraction for 3 hours in a boiling aqueous Tween 20 solution (20 wt %).

Two cubes (10×10×10 mm) were machined from the puck and were kept in a vacuum oven at a pressure of $2 \times 10^{-6}$ atm (argon) and a temperature of 220° C. for 105 minutes. Thereafter, samples were taken out of the oven and cooled in air to about room temperature. One of the cubes was boiled in Tween 20 (20% by weight in water) solution for 3 hours. FTIR analysis was conducted on 150 micron sections obtained from the center of the cube which were parallel to the bottom surface of the oven (FIG. 7). Results are compared for both the samples in FIG. 17. The vitamin E concentration at the surface (1 mm) of the high temperature exposed and Tween 20 extracted UHMWPE was less than the high temperature exposed UHMWPE. These results showed that the vitamin E concentration profile could be further modified by further extraction in a solution of Tween 20 after extraction by high temperature exposure.

Example 15

Manipulation of Vitamin E Profile by Treatment with Hexane/Ethanol after Extraction in Ovens A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E concentration.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press (3895 Auto-M, Carver, Wabash, Ind.) where it was sintered, then compressed to 20 MPa at about 194° C. for 10 minutes, then cooled to room temperature under pressure. Then, the puck was cooled for approximately 1.5 hours under pressure.

Figure 18:
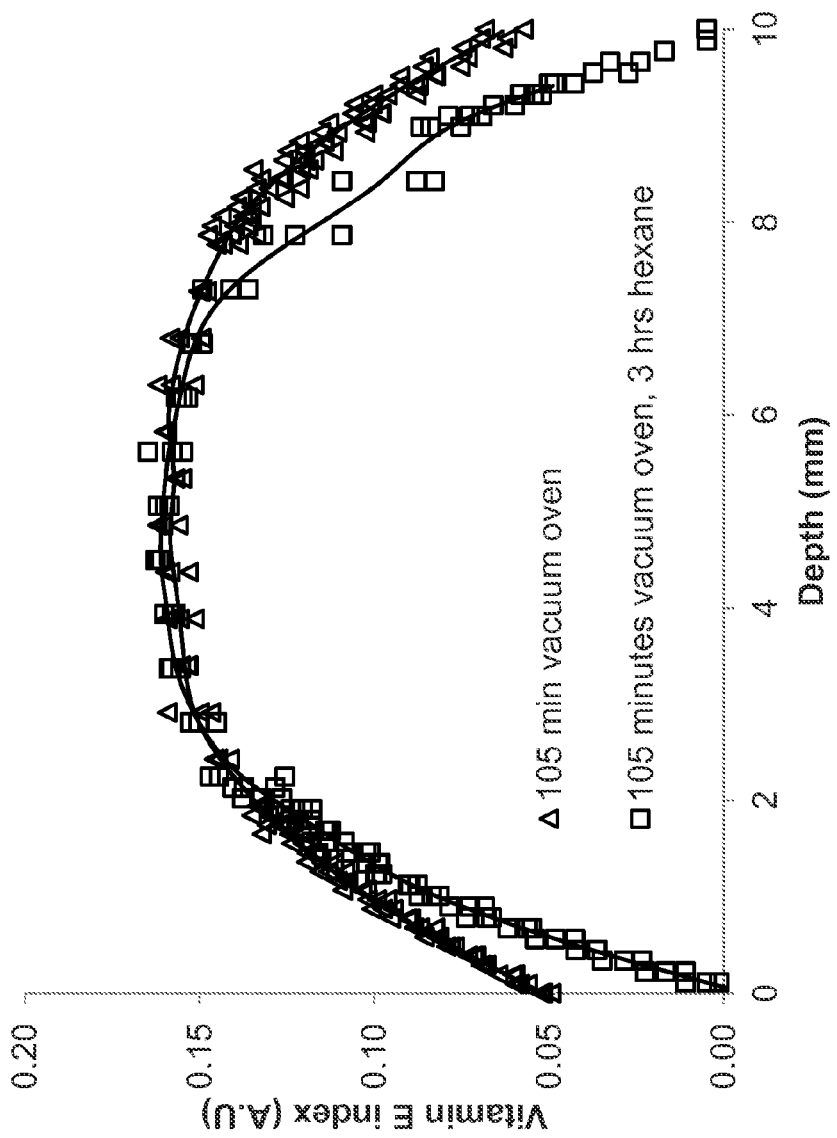
FIG. 18 is a vitamin E concentration profile of 1 wt % vitamin E blended UHMWPE after exposure to 220° C. in vacuum ($2\times10^{-6}$ atm argon) for 105 minutes and further extraction for 3 hours in a boiling hexane.

Two cubes (10 mm) were machined from the puck and were kept in a vacuum oven at a pressure of $2 \times 10^{-6}$ atm and a temperature of 220° C. for 105 minutes. Thereafter, samples were taken out of the oven and cooled in air at room temperature. One of the cubes was boiled in hexane for 3 hours. FTIR analysis was conducted on 150 micron sections obtained from the center of the cube which were parallel to the bottom surface of the oven (FIG. 7). Results are compared for both samples in FIG. 18. The vitamin E concentration at the surface (1 mm) of the high temperature exposed and hexane extracted UHMWPE was less than the high temperature exposed UHMWPE. These results showed that the vitamin E concentration profile could be further modified by further extraction in an organic solvent after extraction by high temperature exposure.

Example 16

Manipulation of Vitamin E Profile by Treatment with Tween 20 Surfactant Before Extraction at High Temperature A 5 wt % concentration mixture of vitamin E with UHMWPE (GUR 1050) was prepared by first mixing isopropyl alcohol (IPA) with vitamin, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E concentration.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 19:
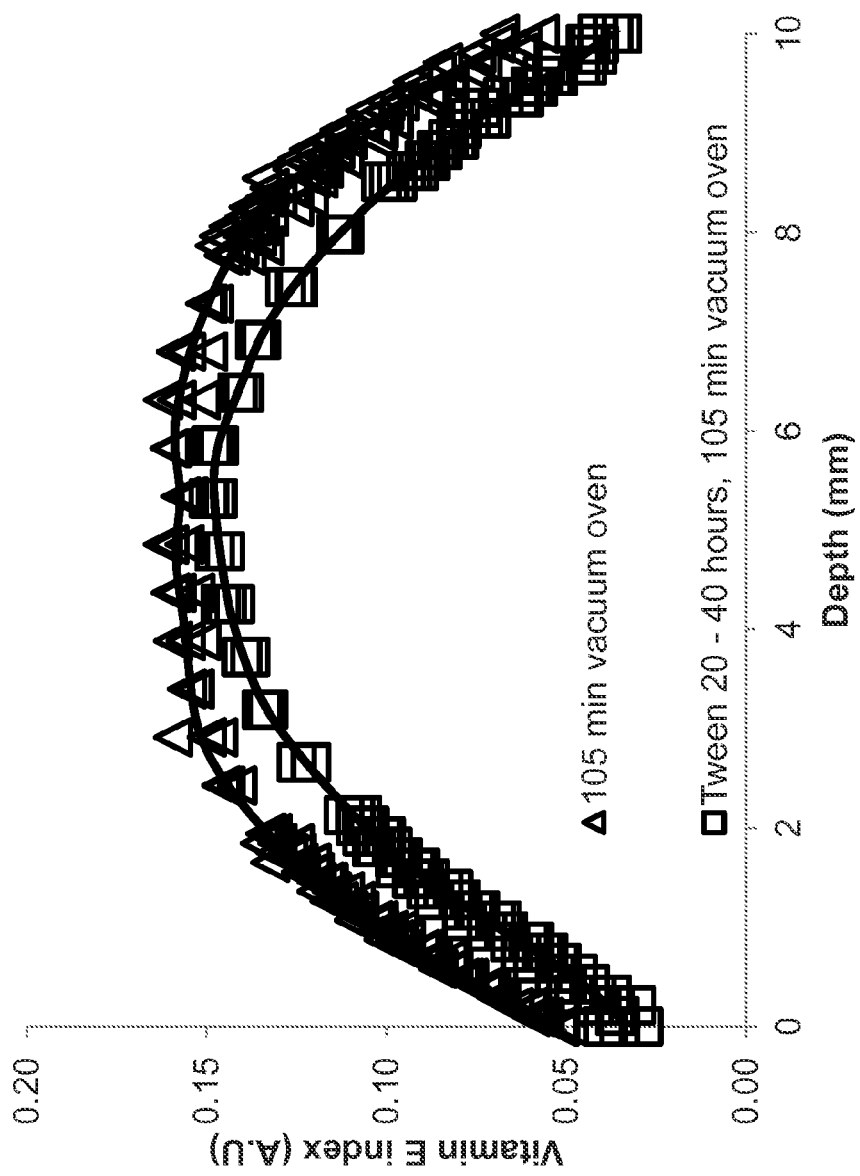
FIG. 19 is a vitamin E concentration of 1 wt % vitamin E-blended UHMWPE extracted using a 20 wt % Tween 20 solution in water followed by high temperature exposure at 200° C. for 105 minutes in $2\times10^{-6}$ atm (argon).

Two cubes (10×10×10 mm) were machined from the puck and one of them was boiled in Tween 20 solution (20 wt % in water) for 40 hours. The cube was removed after 40 hours and both the cubes (both treated and untreated with Tween 20) were kept in a vacuum oven at a pressure of $2 \times 10^{-6}$ atm (argon) and a temperature of 220° C. for 105 minutes. Thereafter, samples were taken out of the oven and cooled in air to about room temperature. FTIR analysis was conducted on 150 micron sections obtained from the center of the cube which were parallel to the bottom surface of the oven (FIG. 7). Results are compared for both the samples in FIG. 19. The vitamin E concentration of the UHMWPE blends extracted using a Tween 20 solution followed by high temperature exposure at 220° C. were lower in the surface and in the bulk compared to UHMWPE blends extracted using just high temperature exposure for the same duration at 220° C. These results showed that the vitamin E concentration of vitamin E blends of UHMWPE could be manipulated via extraction using a surfactant solution before high temperature exposure.

Example 17

Manipulation of Vitamin E Profile by Doing Oven Extraction on Oven Extracted and Tween 20 Treated Samples A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E concentration.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 20:
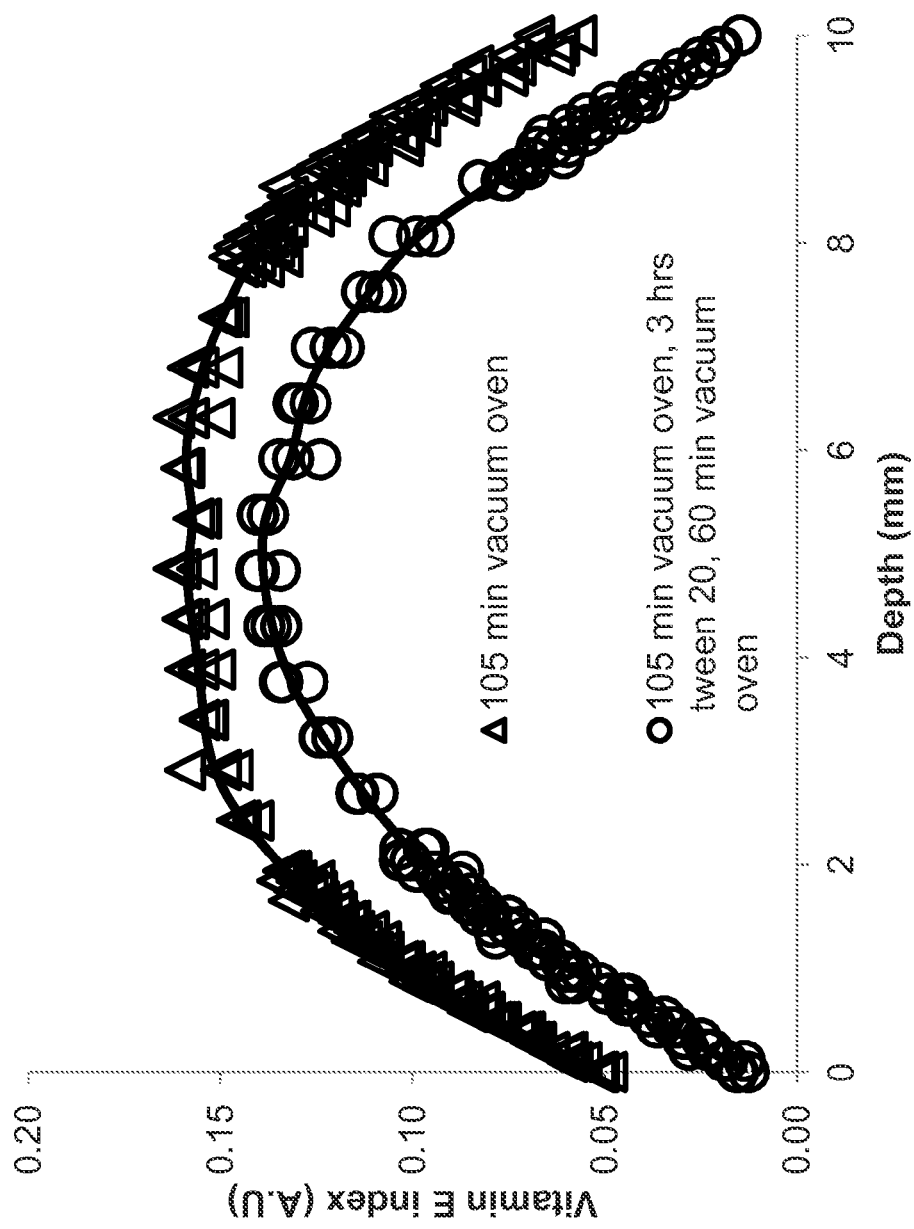
FIG. 20 is a vitamin E concentration profile of 1 wt % vitamin E-blended UHMWPE exposed to 220° C. for 105 minutes, then extracted using a Tween 20 solution followed by further exposure to 220° C. compared to 1 wt % vitamin E blended UHMWPE exposed to 220° C. alone for 105 minutes

Two cubes (10×10×10 mm) were machined from the puck and kept in a vacuum oven at a pressure of $2 \times 10^{-6}$ atm (argon) and a temperature of 220° C. for 105 minutes. Thereafter, samples were taken out of the oven and cooled in air at room temperature. One of the cubes was boiled in a Tween 20 solution (20 wt % in water) for 3 hours and cooled in air. Thereafter, this cube was kept in vacuum oven at $2 \times 10^{-6}$ atm pressure (argon) and a temperature of 220° C. for 60 minutes. FTIR analysis was conducted on 150 micron sections obtained from the center of both the cubes which were parallel to the bottom surface of the oven (FIG. 7). Results are compared for both the samples in FIG. 20. The vitamin E concentration profile of 1 wt % vitamin E-blended UHMWPE exposed to 220° C. for 105 minutes, then extracted using a Tween 20 solution followed by further exposure to 220° C. was lower in the surface and in the bulk compared to 1 wt % vitamin E blended UHMWPE exposed to 220° C. alone for 105 minutes. Thus, the vitamin E concentration of vitamin E blended UHMWPEs could be manipulated by multiple high temperature exposure and surfactant solution extraction steps.

Example 18

Manipulation of Vitamin E Profile by Oven Extraction on Oven Extracted and Ethanol Treated Samples A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E concentration.

A puck (diameter 10 cm, thickness 1-1.1 cm) of 1 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled for approximately 1.5 hours under pressure.

Figure 21:
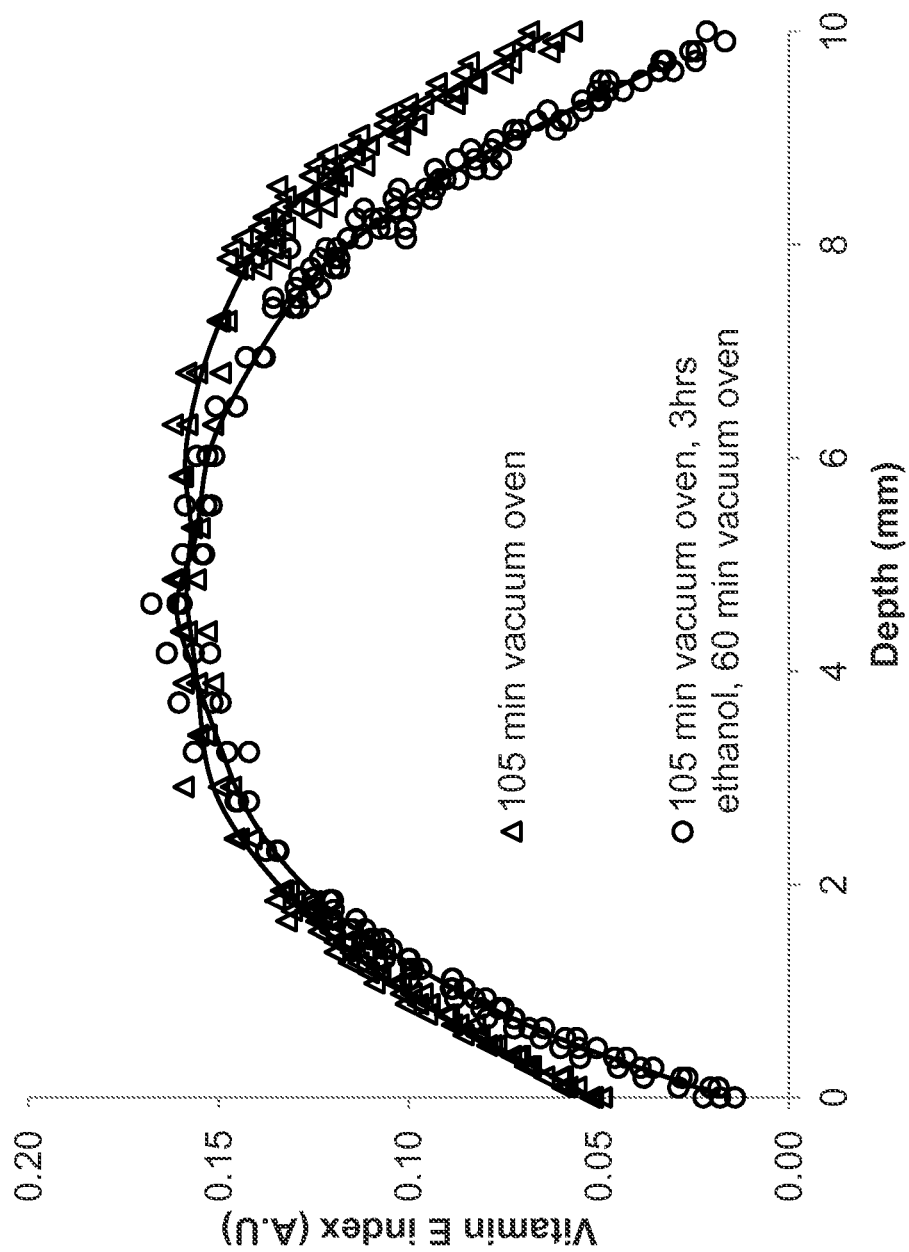
FIG. 21 is a vitamin E concentration profile of 1 wt % vitamin E-blended UHMWPE after exposure to 220° C. in vacuum ($2\times10^{-6}$ atm argon) for 105 minutes followed by 3 hours boiling in ethanol followed by exposure to 220° C. for 60 minutes.

Two cubes (10×10×10 mm) were machined from the puck and kept in a vacuum oven at a pressure of $2 \times 10^{-6}$ atm and a temperature of 220° C. for 105 minutes. Thereafter, samples were taken out of the oven and cooled in air at room temperature. One of the cubes was boiled in ethanol for 3 hours and cooled in air. Thereafter, this cube was kept in a vacuum oven at $2 \times 10^{-6}$ atm pressure (argon) and a temperature of 220° C. for 60 minutes. FTIR analysis was conducted on 150 micron sections obtained from the center of both the cubes which were parallel to the bottom of surface of the oven (FIG. 7). Results are compared for both the samples in FIG. 21. The vitamin E concentration profile of 1 wt % vitamin E-blended UHMWPE exposed to 220° C. for 105 minutes, then to boiling ethanol for 3 hours, then to 220° C. for 60 minutes showed a decreased surface concentration of vitamin E. Therefore, these results showed that the vitamin E profile could be modified via performing multiple steps of high temperature exposure followed by solvent extraction by ethanol.

Example 19

Surface Extraction of Vitamin E from Vitamin E-containing Samples Along with the Diffusion of Vitamin E from the Back Surface Towards Load Bearing Surface in a Nitrogen Convection Oven A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 3 wt % and 0.3 wt % vitamin E.

Two pucks (diameter 10 cm, thickness 1-1.1 cm) of 3 wt % and 0.3 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled for approximately 1.5 hours under pressure.

Figure 22:
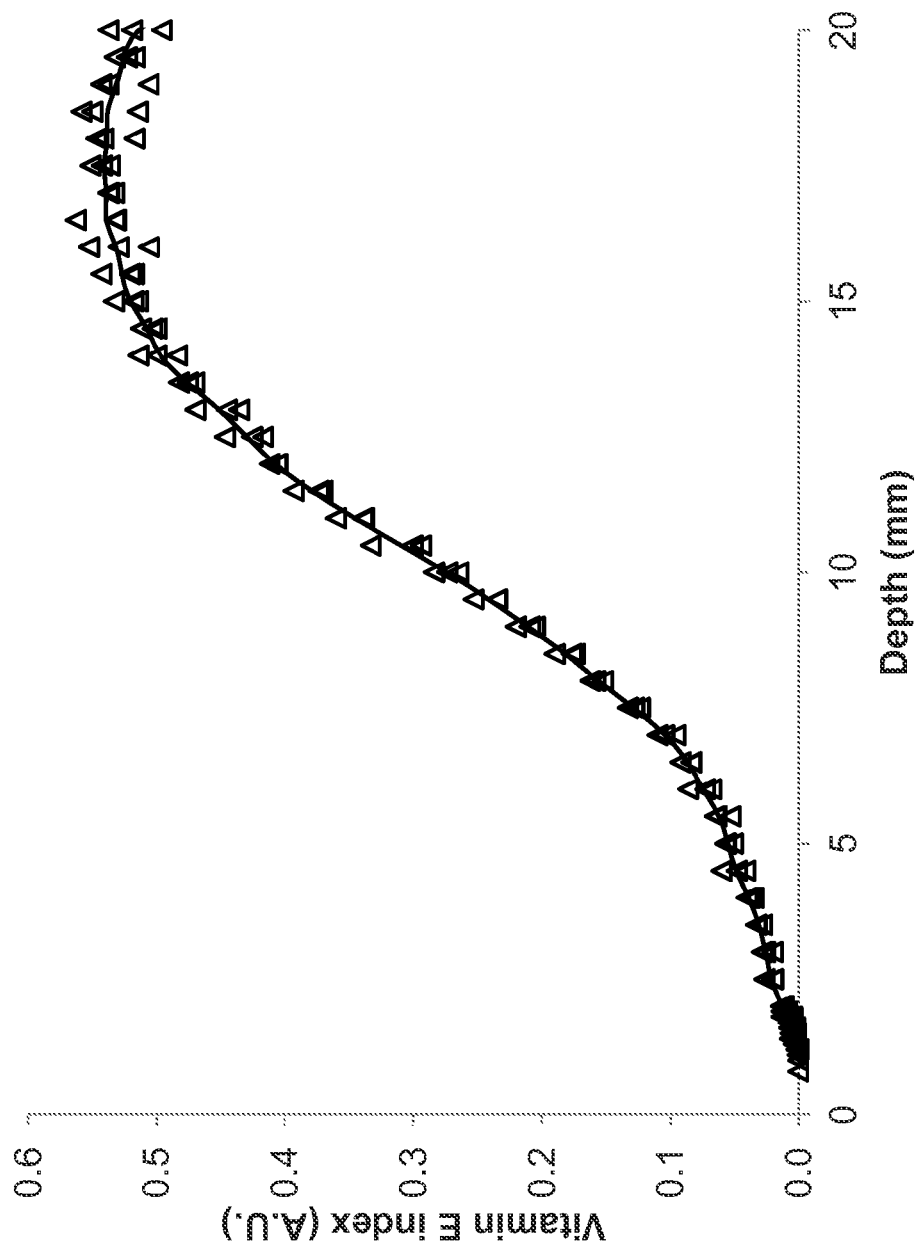
FIG. 22 is a vitamin E concentration profile of a 0.3 wt % vitamin E-blended cube (10 mm-thick) which was exposed to 290° C. for 120 minutes in contact with a 3 wt % vitamin E blended cube (contact at 10 mm).
Figure 23:
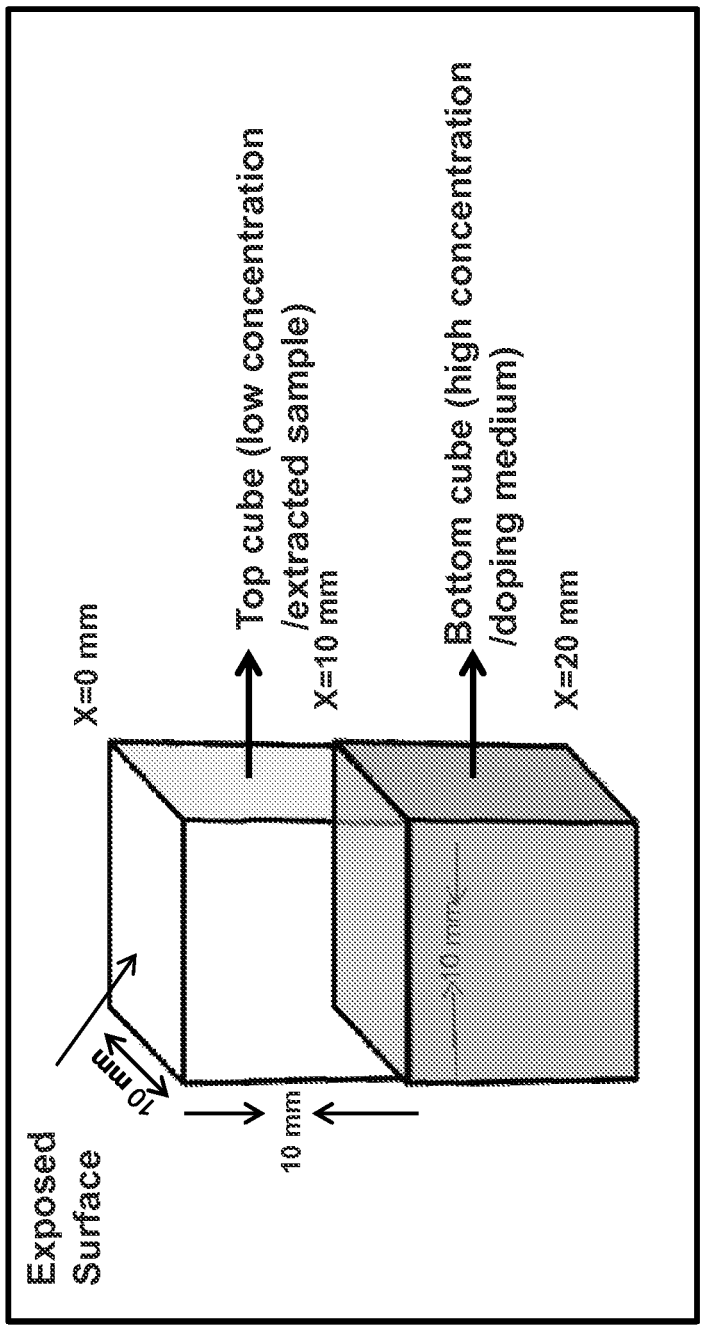
FIG. 23 shows a schematic of the high temperature extraction of vitamin E from exposed surface in oven with simultaneous doping of vitamin E from back surface through a doping medium (10 mm. cube) (Not drawn to scale—measurements in mm.).

Two cubes (10×10×10 mm) each were machined from these pucks and the lower concentration cube (0.3 wt % vitamin E cube) was placed on the higher concentration cube (0.3 wt % vitamin E cube) before masking 5 of the six sides with aluminum foil. One circular surface with a lower concentration (0.3 wt % vitamin E cube) was left unmasked. The samples were placed in a pre-heated nitrogen convection oven at 290° C. with the unmasked surface exposed to nitrogen flow. The pucks were kept in the oven under these conditions for approximately 120 minutes. Samples were removed from the oven and were cooled in air to about room temperature. FTIR analysis was conducted on the 150 micron sections that were obtained away from the edges (FIG. 1). Results are plotted as a function of depth in FIG. 22. Here x=0 represents surface of the top puck which initially had 0.3 wt % of vitamin E while x=20 mm represents the bottom surface which was masked and in contact with the bottom surface of the oven (FIG. 23). These results showed that simultaneous diffusion of sample from the backside surface and extraction from the surface was a viable alternative to manufacture polymeric material with low vitamin E concentration in the surface and high vitamin E concentration in the bulk.

Example 20

Radiation Cross-linking of Surface Extracted and Bulk Diffused Vitamin E Containing UHMWPE Pucks A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 3 wt % and 0.3 wt % vitamin E.

Two pucks (diameter 10 cm, thickness 1-1.1 cm) of 3 wt % and 0.3 wt % vitamin E-containing UHMWPE blend were prepared via compression molding. The powder was preheated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled for approximately 1.5 hours under pressure.

Figure 24:
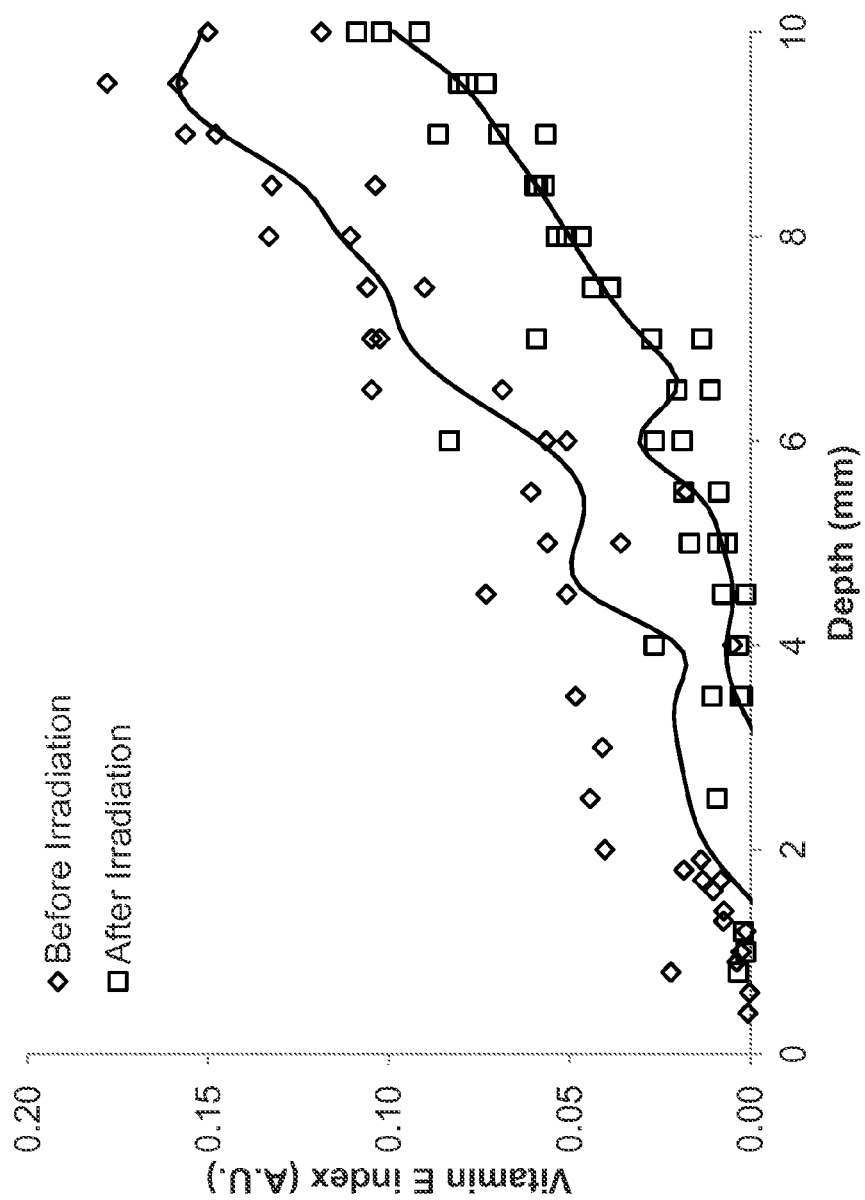
FIG. 24 is a vitamin E concentration profile of a 0.3 wt % vitamin E-blended puck (10 mm-thick) which was exposed to 290° C. for 290 minutes in contact with a 3 wt % vitamin E blended puck (contact at 10 mm.) before and after irradiation to 175 kGy.

Two pucks (10 cm diameter, 10 mm thick) were placed on top of each other (to extract from the top puck and diffuse vitamin E from the bottom puck towards the surface of the top puck) and masked with aluminum foil on five sides except for the top surface (0.3 wt % vitamin E puck). Samples were placed in a pre-heated nitrogen convection oven at 290° C. with the unmasked surface exposed to nitrogen flow. The pucks were kept in the oven under these conditions for approximately 290 minutes. Samples were removed from the oven and were cooled in air to about room temperature. After cooling, the top puck was irradiated by electron beam irradiation using a Van-de-Graff generator at 3.0 MeV to a dose of 175 kGy at 25 kGy/pass. FTIR analysis was conducted on the irradiated samples as described in FIG. 1. The vitamin E index as a function of depth is compared before and after irradiation in FIG. 24. The vitamin E index was decreased after irradiation and the vitamin E index at x=2 mm was below the detection limit designated as a vitamin E index of 0.02.

The cross-link density of sections from the irradiated pucks was calculated. Samples (3×3×1 mm) were cut by razor blade as shown in FIG. 4. The samples were swollen in xylene pre-heated to 130° C. for 2 hours. Weights of sample were measured before and after xylene swelling.

Cross-link density was calculated using Equation 2.

Figure 25:
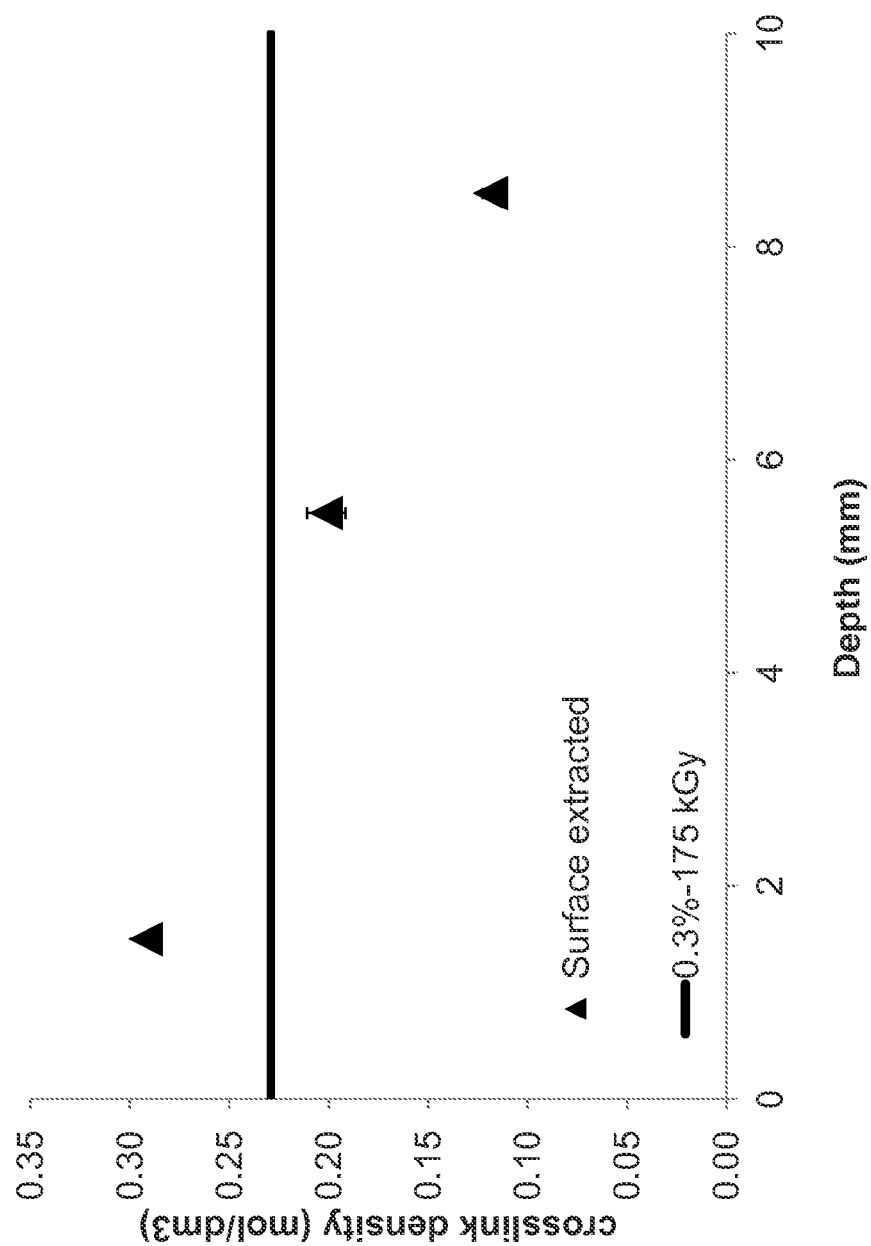
FIG. 25 shows the cross-link density of 0.3 wt % UHM-WPE puck (10 mm. thick) irradiated to 175 kGy compared to the cross-link density of a 0.3 wt % vitamin E-blended puck (10 mm.-thick) which was exposed to 290° C. for 290 minutes in contact with a 3 wt % vitamin E blended puck (contact at 10 mm.) also irradiated to 175 kGy.

The volumetric equilibrium expansion ratio, $q_{eq}$, was calculated from the weight swelling ratio using a density for dry polyethylene of 0.94 g cm$^{-3}$ and a density for xylene of 0.75 g cm$^{-3}$ at 130° C. Cross-link density is plotted as a function of depth in FIG. 25. The control was a 0.3 wt % vitamin E blended UHMWPE puck (diameter 10 cm, thickness 1.1 cm) prepared as described above and irradiated to 175 kGy. Cross-link density of extracted and doped sample was higher than the control puck at the surface (p<0.01) while it was lower in bulk compared to same control (p<0.01)

Example 21

Wear Rate of Surface Extracted and Bulk Diffused Vitamin E Containing UHMWPE Pucks A 5 wt % concentration mixture of vitamin E with UHMWPE (GUR 1050) was prepared by first mixing isopropyl alcohol (IPA) with vitamin, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 3 wt % and 0.3 wt % vitamin E respectively.

Two pucks (diameter 10 cm, thickness 1-1.1 cm) of 3 wt % and 0.3 wt % vitamin E-containing UHMWPE blend were prepared via compression molding. The powder was preheated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Two pucks were placed on top of each other (to extract from the top puck and diffuse vitamin E from the bottom puck) and masked with aluminum foil on 5 sides except one circular surface with the lower concentration (0.3 wt % vitamin E puck). Samples were placed in a pre-heated nitrogen convection oven at 290° C. with the unmasked surface exposed to nitrogen flow. The pucks were kept in the oven under these conditions for approximately 290 minutes. Samples were removed from the oven and were cooled in air at room temperature. After cooling, the top puck was irradiated by electron beam irradiation using a Van-de-Graff generator at 3.0 MeV to a dose of 175 kGy at 25 kGy/pass.

As specified earlier, cylindrical pins of 9 mm diameter and 9 mm length were machined from the top 10 mm of the material by machining off 1 mm from the exposed surface and bi-directional pin-on-disk wear test was conducted for the irradiated materials. Wear testing was conducted for approximately 1 million cycles. Pins were tested against CoCr in bovine serum at 2 Hz. Weight loss was measured approximately every 0.125 MC and wear rate is reported as a linear regression of weight loss versus number of cycles from 0.5 MC to 1 MC. Wear rate for extracted and irradiated materials was 1.6±0.3 mg/MC and was statistically similar to the wear rate of 0.1 wt % vitamin E blended material irradiated to 100 kGy (1.1±0.2 mg/MC, p=0.13). These results are indicative that a highly wear resistant UHMWPE can be achieved by high temperature exposure for extraction of vitamin E from the surface with simultaneous doping from vitamin E-blended UHMWPE followed by irradiation.

Example 22

Surface Extraction Accompanied by Diffusion of Vitamin E from the Posterior Surface Through Doped Porous Ceramic A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 0.3 wt % vitamin E concentration.

A puck (diameter 10 cm, thickness 1-1.1 cm) of 0.3 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 26:
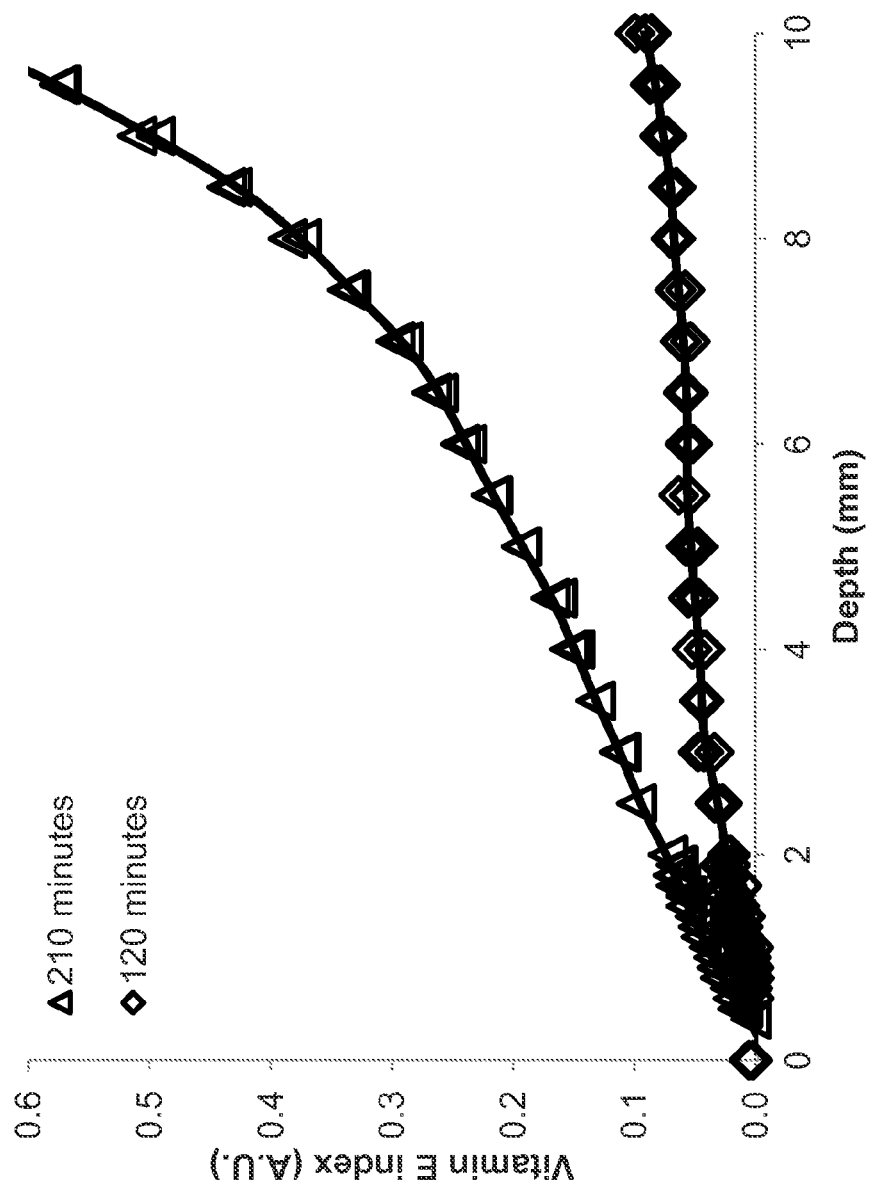
FIG. 26 shows the vitamin E concentration profile of a 0.3 wt % vitamin E-blended cuboid (20 mm.-thick) which was exposed to nitrogen at 290° C. for 120 minutes and 210 minutes and was simultaneously contacted with vitamin E doped porous ceramic (contact at 20 mm.).

Two cuboids (20×10×10 mm) were machined out of these pucks. Separately, two pieces of porous ceramic (Fisher, Pittsburgh, Pa.) were machined in form of small cylinders of 1 cm diameter and 1 cm as thickness. Thereafter, they were doped in pure vitamin E overnight for around 14 hours. Each cuboid was placed on one porous ceramic cylinder such that one 10×10 mm surface of the cuboid was in contact with ceramic. The whole assembly is masked with aluminum foil such that only one 10×10 mm surface (surface opposite to the one in contact with ceramic) was left exposed. Samples were kept in a nitrogen convection oven at 290° C. for either 120 minutes or 210 minutes. After the designated time, samples were taken out of the oven and cooled in air at room temperature until steady state was reached. FTIR analysis was conducted on 150 micron sections obtained from the center of the cuboids such that x=0 represents the surface exposed to nitrogen while x=20 is the surface in contact with the ceramic, similar to the method described in FIG. 1. As shown in FIG. 26, the surface had very low concentrations of vitamin E as compared to the bulk for both durations.

Example 23

Surface Extraction Along with Diffusion of Vitamin E from the Dip Coated Back Surface A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 0.3 wt % vitamin E concentration.

A puck (diameter 10 cm, thickness 1-1.1 cm) of 0.3 wt % vitamin E-containing UHMWPE blend was prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled for approximately 1.5 hours under pressure.

Figure 27:
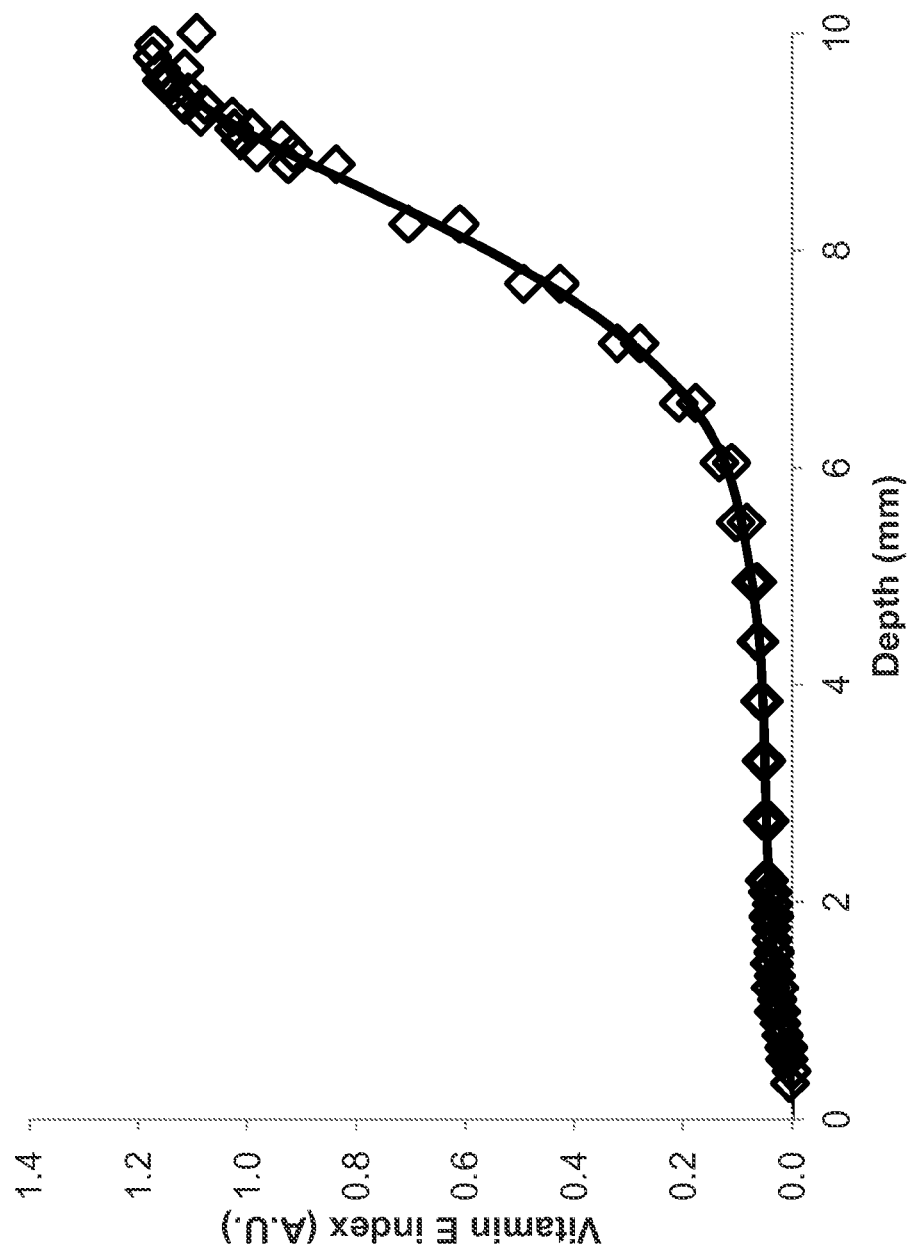
FIG. 27 shows the vitamin E concentration profile of a 0.3 wt % vitamin E-blended cube (10 mm.-thick) which was exposed to nitrogen at 290° C. for 30 minutes. Cube was dip-coated on 5 sides (x=10 mm.) with vitamin E at room temperature before extraction in oven.

A cube (10×10×10 mm) was machined out of the puck and dipped in vitamin E on 5 sides. The process of dip coating is better controlled using a dip coater which aids in controlling the speed of dipping, thereby providing a uniform film thickness on the sample. The 5 coated sides were masked with aluminum foil and the sample was kept in a nitrogen convection oven with the unexposed (non-coated) surface in contact with nitrogen. The oven was maintained at 290° C. and the sample was heated for 30 min. Thereafter, the sample was removed and cooled in air at room temperature until steady state was reached. FTIR analysis was conducted on 150 micron sections obtained from the center of the cubes where x=0 represents the surface exposed to nitrogen and x=10 is the bottom surface that was dip coated, masked with aluminum foil and in contact with the bottom surface of the oven (FIG. 1). As depicted in FIG. 27, the surface had very low concentrations of vitamin E as compared to the bulk; therefore dip coating along with surface extraction by high temperature exposure is a viable alternative to obtain lower surface concentration of vitamin E on the samples as compared to the bulk.

Example 24

Manipulation of Vitamin E Profile in Surface Extracted and Back Side Vitamin E Doped Samples by Changing Time A 5 wt % concentration mixture of vitamin E with UHMWPE (GUR 1050) was prepared by first mixing isopropyl alcohol (IPA) with vitamin, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 3 wt % and 0.3 wt % vitamin E respectively.

Two pucks (diameter 10 cm, thickness 1-1.1 cm) of 3 wt % and 0.3 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 28:
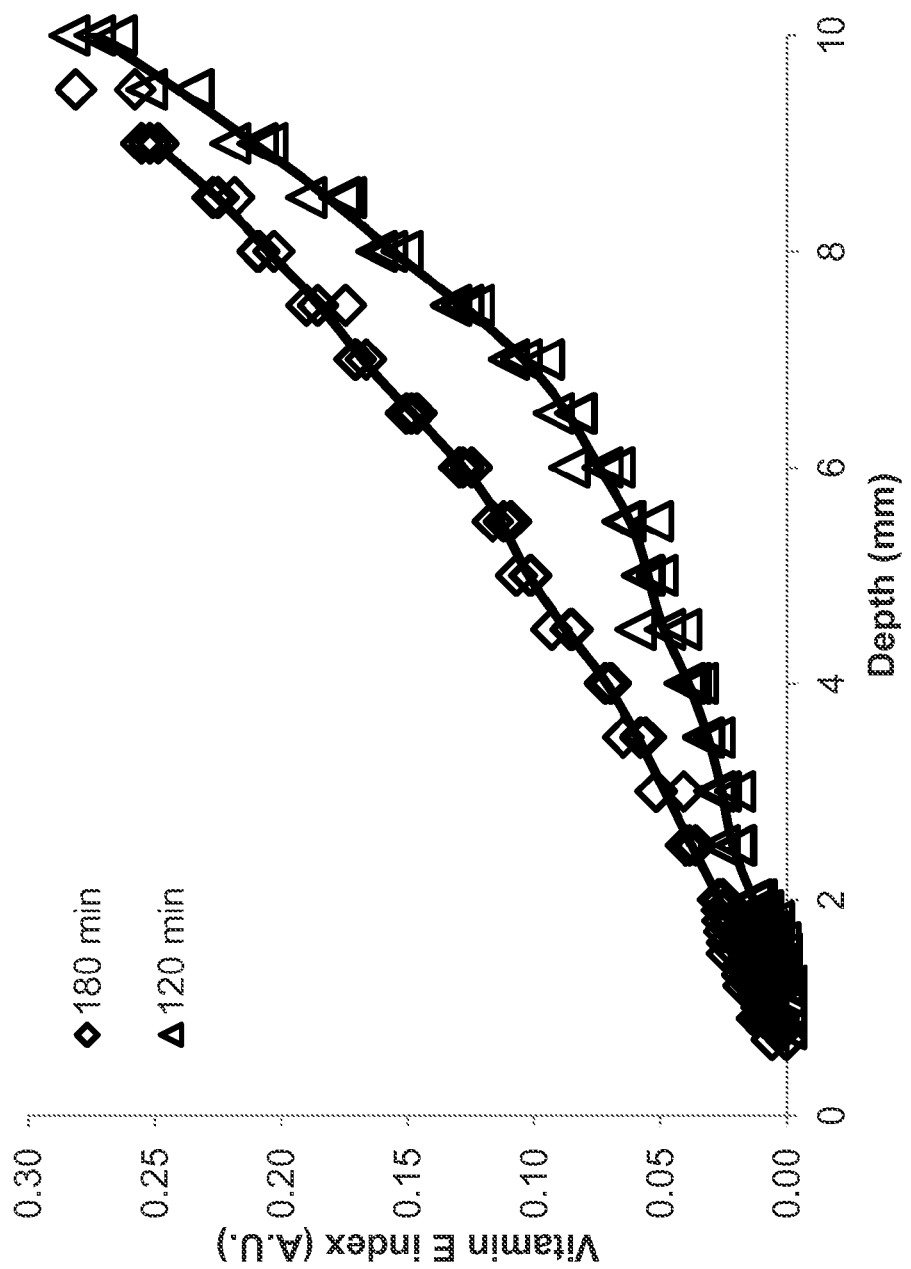
FIG. 28 shows the vitamin E concentration profile of a 0.3 wt % vitamin E-blended cube (10 mm.-thick) which was in contact with a 3 wt % vitamin E blended cube (contact at 10 mm.) and was exposed to 290° C. for 120 minutes and 180 minutes respectively.

Two cubes (10×10×10 mm) each were machined from these pucks and the lower concentration cube was placed on the higher concentration cube before masking with aluminum foil on 5 sides of the sample. One circular surface with the lower concentration (0.3 wt % vitamin E cube) was left unmasked. They were placed in a pre-heated nitrogen convection oven at 290° C. with the unmasked surface exposed to nitrogen flow. One set of cubes was treated in the oven for 120 minutes while other set was treated for 180 minutes. Samples were removed from the oven and were cooled in air at room temperature. FTIR analysis was conducted on 150 micron sections obtained away from the edges (FIG. 1). Results are plotted as a function of depth in FIG. 28. Here x=0 represents the surface of the top puck which initially had 0.3 wt % of vitamin E concentration while x=20 mm represents the bottom surface which is masked and in contact with the bottom surface of the oven. Data is presented for the first 10 mm depth of the sample. As high temperature exposure increased from 120 minutes to 180 minutes, the diffusion amount from the back side increased leading to an increase in vitamin E concentration in the sample.

Example 25

Manipulation of Vitamin E Profile in Surface Extracted and Back Side Vitamin E Doped Samples by Changing Initial Concentration of Vitamin E in Samples Before Extraction A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 2 wt % and 0.3 wt % vitamin E.

Two pucks (diameter 10 cm, thickness 1-1.1 cm) of 3 wt % and 0.3 wt % vitamin E-containing UHMWPE blend were prepared via compression molding. Virgin (0% vitamin E) pucks were prepared by similar procedure, without mixing the vitamin E mixture with the UHMWPE powder. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled for approximately 1.5 hours under pressure.

Figure 29:
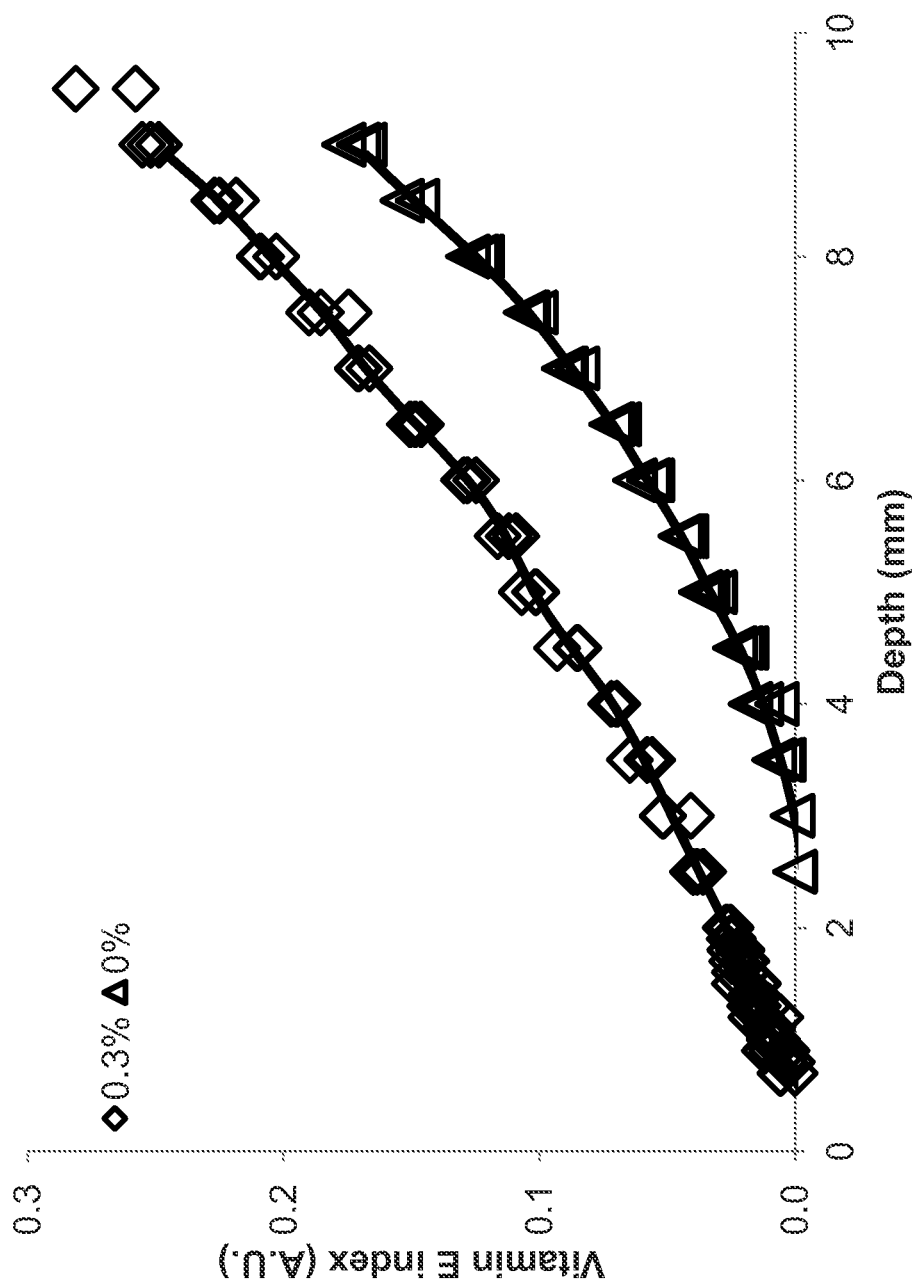
FIG. 29 shows the vitamin E concentration profile of samples having initial concentration of 0% and 0.3 wt % vitamin E respectively, extracted in convection oven in nitrogen at 290° C. for 180 minutes while in contact with a 3 wt % vitamin E blended cube (contact at 10 mm.).

Two cubes (10×10×10 mm) of concentration 0.3% and 3% were placed on top of each other (to extract from the top puck and diffuse vitamin E from the bottom puck towards the surface of the top puck) and masked with aluminum foil on 5 sides except for the top surface (0.3 wt % vitamin E puck). An additional sample was prepared by placing a virgin cube (10×10×10 mm) on top of 3% vitamin E concentration cube (10×10×10 mm) and masking the 5 sides except the extraction surface (virgin puck). These two samples were placed in a pre-heated nitrogen convection oven at 290° C. with the unmasked surface exposed to nitrogen flow. The cubes were kept in the oven under these conditions for approximately 180 minutes. Samples were removed from the oven and were cooled in air to about room temperature. FTIR analysis was conducted on these samples as described in FIG. 1. The vitamin E index as a function of depth is compared for both the samples in FIG. 29. The samples with an initial concentration of 0.3% in the top cube had surface concentrations greater than the samples with a virgin cube as the top cube.

Example 26

Manipulation of Vitamin E Profile in Surface Extracted and Back Side Vitamin E Doped Samples by Changing Initial Concentration of Vitamin E in Doping Medium A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 0.3 wt %, 2 wt %, and 3 wt % vitamin E.

Four pucks (diameter 10 cm, thickness 1-1.1 cm) of 5 wt %, 3 wt %, 2 wt % and 0.3 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 30:
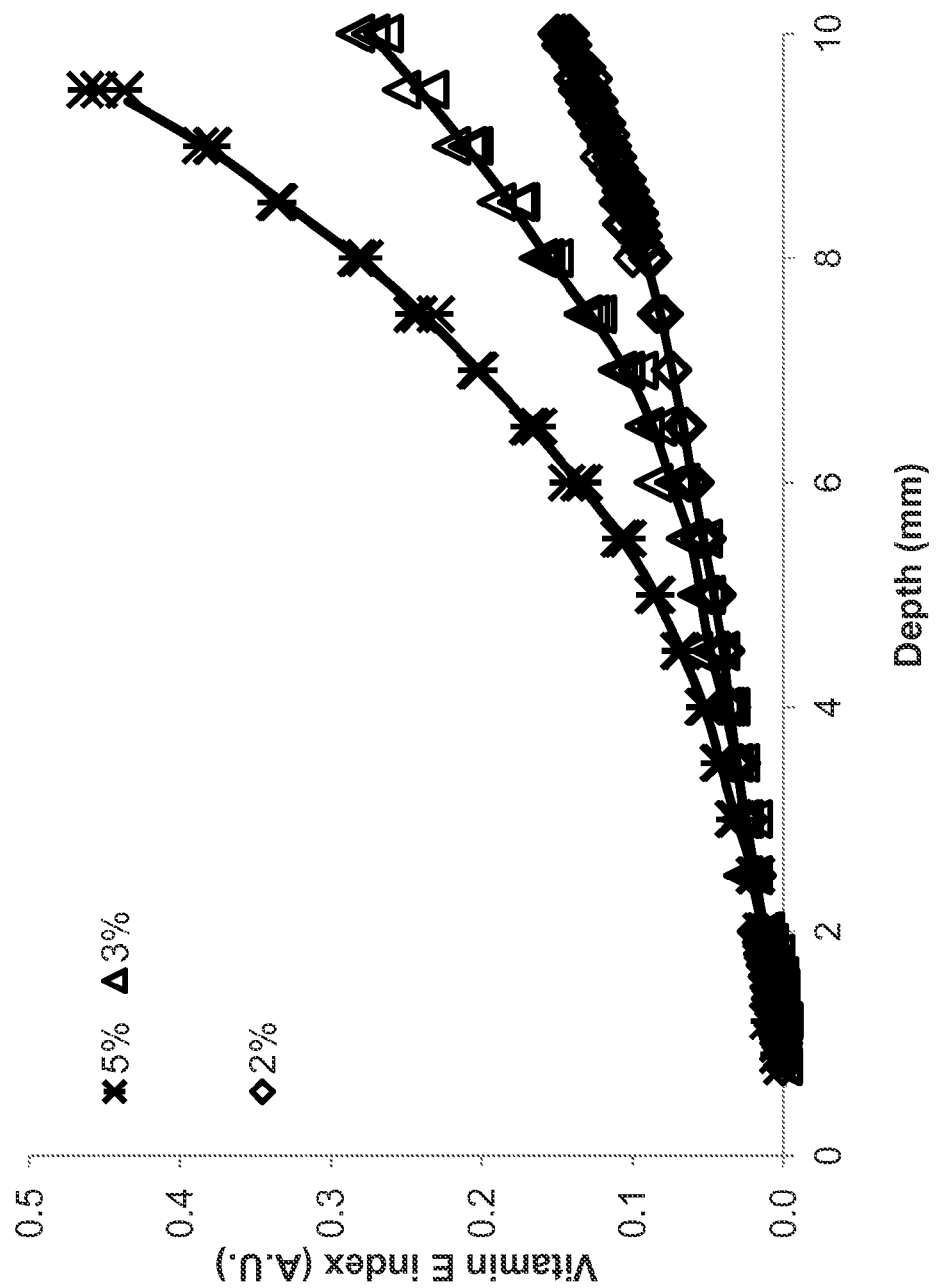
FIG. 30 shows a vitamin E concentration profile of samples having initial concentration 0.3 wt % vitamin E respectively, extracted in convection oven in nitrogen at 290° C. for 180 minutes while in contact with vitamin E blended cubes of 2 wt %, 3 wt % and 5 wt % vitamin E concentration respectively (contact at 10 mm.).

Two cubes (10×10×10 mm) of concentration 0.3% and 2% were placed on top of each other (to extract from the top puck and diffuse vitamin E from the bottom puck towards the surface of the top puck) and masked with aluminum foil on 5 sides except for the top surface (0.3 wt % vitamin E puck). Another sample was prepared by placing 0.3 wt % (10×10×10 mm) on top of 3% vitamin E concentration cube (10×10×10 mm) and masking the 5 sides except the extraction surface (virgin puck). A third sample was prepared in a similar way except that a 5 wt % cube was used as the bottom cube. These three samples were placed in a pre-heated nitrogen convection oven at 290° C. with the unmasked surface exposed to nitrogen flow. The cubes were kept in the oven under these conditions for approximately 180 minutes. Samples were removed from the oven and were cooled in air to about room temperature. FTIR analysis was conducted on these samples as described in FIG. 1. The vitamin E index as a function of depth is compared for both the samples in FIG. 30. As the concentration of vitamin E in the bottom cube (doping medium) was increased, the bulk concentration increased in the top puck, while the surface concentration remained similar for each of the samples.

Example 27

Manipulation of Vitamin E Profile in Surface Extracted and Back Side Vitamin E Doped Samples by Changing Number of Layers Used as a Doping Medium A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 0.3 wt % and 2 wt % vitamin E.

Three pucks (diameter 10 cm, thickness 1-1.1 cm) of 5 wt %, 2 wt % and 0.3 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 31:
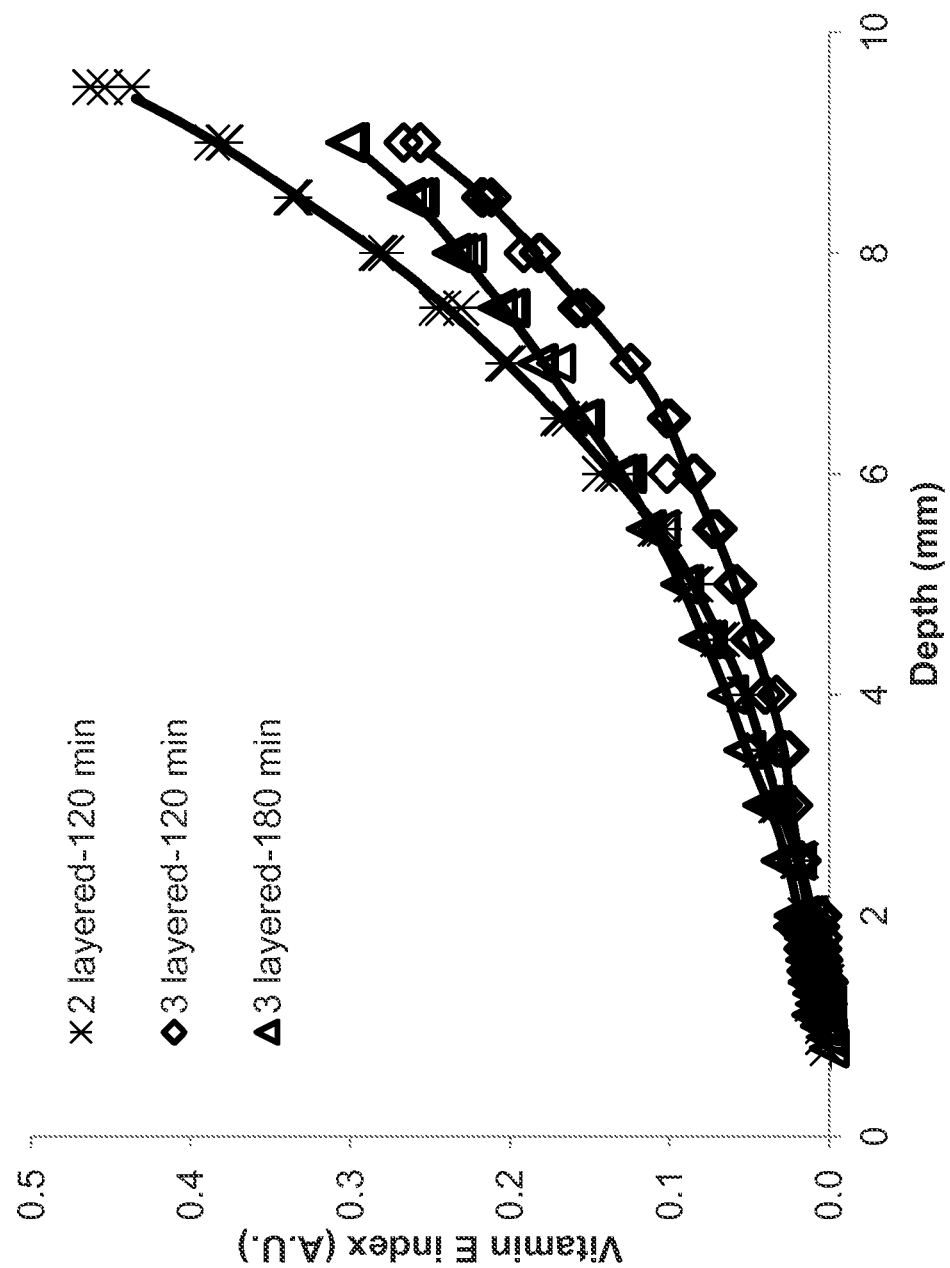
FIG. 31 shows vitamin E index as a function of depth was compared for surface extracted and back side vitamin E doped samples by changing number of layers used as a doping medium.

Two cubes (10×10×10 mm) of concentration 0.3% and 5% were placed on top of each other (to extract from the top puck and diffuse vitamin E from the bottom puck towards the surface of the top puck) and masked with aluminum foil on 5 sides except for the top surface (0.3 wt % vitamin E puck). Another sample was prepared by placing 0.3 wt % (10×10×10 mm) on top of 2% vitamin E concentration cuboid of 2 mm depth (10×10×2 mm) followed by a cube (10×10×10 mm) of 5 wt % vitamin E concentration and then masking the 5 sides except for the extraction surface (0.3 wt % cube). A third sample was prepared in a manned analogous to the preparation of the second sample, with three layers from top to bottom having the concentration of 0.3 wt %, 2 wt % and 5 wt % respectively. These three samples were placed in a pre-heated nitrogen convection oven at 290° C. with the unmasked surface exposed to nitrogen flow. First two samples were kept in the oven under these conditions for approximately 120 minutes. The third sample was kept in oven with nitrogen flow at 290° C. for 180 minutes. Samples were removed from the oven and were cooled in air to about room temperature. FTIR analysis was conducted on these samples as described in FIG. 1. The vitamin E index as a function of depth was compared for both the samples in FIG. 31. After an additional 2 mm layer of 2 wt % vitamin E is sandwiched between 2 layers (sample 2 and sample 3), the surface concentration of top cube (0.3 wt % vitamin E) after extraction is same as sample 1 (with two layers) while the bulk concentration is lower than the sample with just two layers (sample 1).

Example 28

Manipulation of Vitamin E Profile in Surface Extracted and Back Side Vitamin E Doped Samples by Changing the Masking Type or not Masking the Back Surface A 5 wt % concentration mixture of vitamin E with UHMWPE (GUR 1050) was prepared by first mixing isopropyl alcohol (IPA) with vitamin E then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 0.3 wt % vitamin E concentration.

Two pucks (diameter 10 cm, thickness 1-1.1 cm) of 5 wt % and 0.3 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled in approximately 1.5 hours under pressure.

Figure 32:
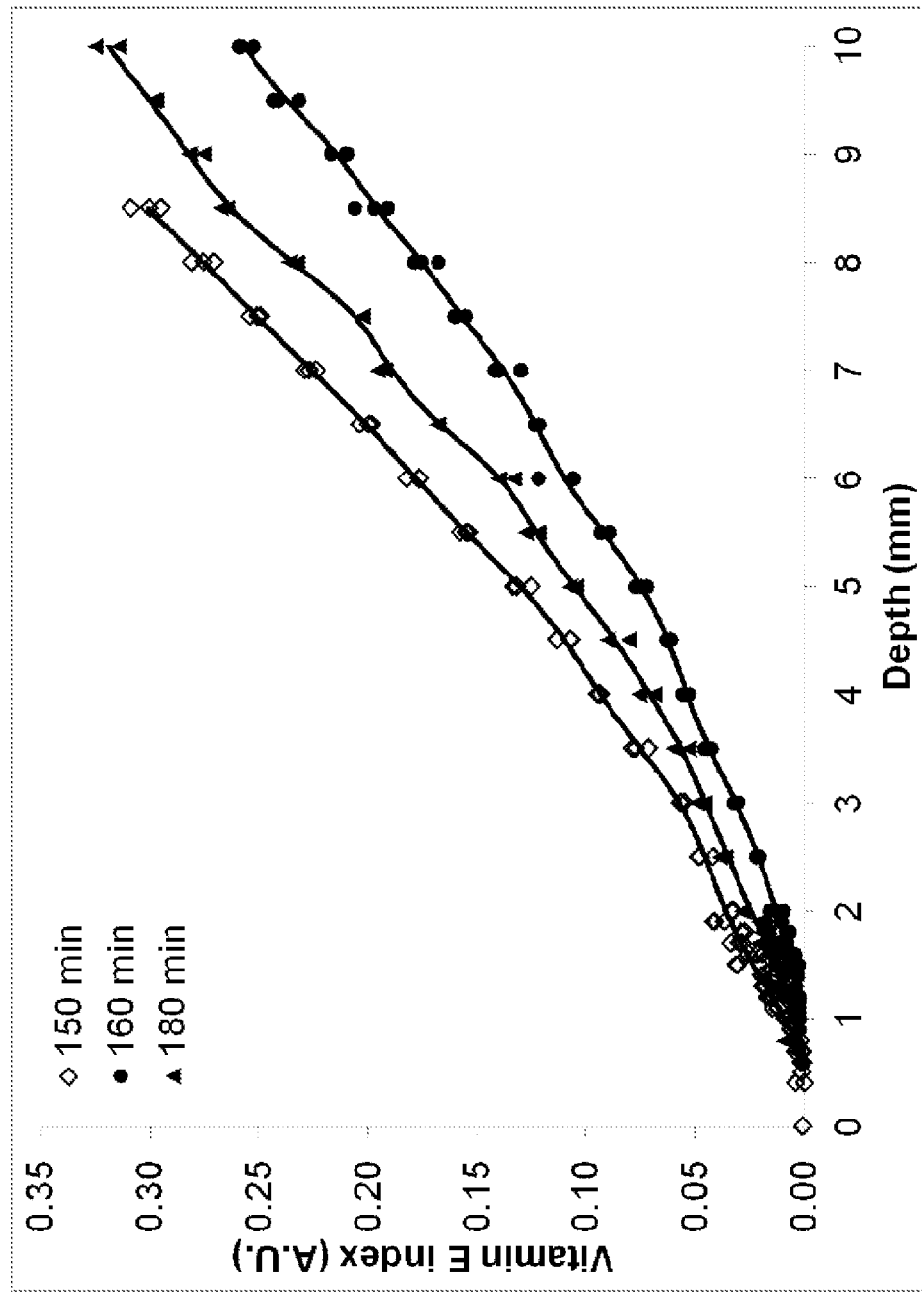
FIG. 32 shows a vitamin E concentration profile of samples having initial concentration 0.3 wt % vitamin E respectively, extracted in convection oven in nitrogen at 290° C. for 150, 160 or 180 minutes while in contact with vitamin E blended cubes with 5 wt % vitamin E concentration (contact at 10 mm.).

A cube (10×10×10 mm) of concentration 0.3 wt % vitamin E was placed on a cuboid of 4 mm thickness (10×10×4 mm) and 5 wt % initial vitamin E concentration (to extract from the top cube and diffuse vitamin E from the bottom cuboid towards the surface of the top cube) and stacked cubes were masked with aluminum foil on four sides excluding the top surface (0.3 wt % vitamin E) and bottom surface (5 wt % vitamin E). Three samples were prepared in a similar way and were placed in a pre-heated nitrogen convection oven at 290° C. with the top and bottom surface exposed to nitrogen flow. Samples remained in the oven for 150 minutes, 160 minutes and 180 minutes, respectively. Samples were then removed from the oven and were cooled in air to about room temperature. FTIR analysis was conducted on these samples as described in FIG. 1, with x=0 being the surface of the exposed top or low concentration cube (0.3 wt % vitamin E). The vitamin E index as a function of depth is compared for all the three samples in FIG. 32. As the duration of heating in the oven was increased from 150 minutes to 180 minutes, both, the measured surface and bulk concentrations decreased.

Example 29

Tensile Testing of Surface Extracted and Radiation Cross-linked Vitamin E Containing UHMWPE Pucks A 5 wt % concentration mixture of vitamin E with UHMWPE (GUR 1050) was prepared by first mixing isopropyl alcohol (IPA) with vitamin E, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 1 wt % vitamin E.

Two pucks (diameter 10 cm, thickness 1-1.1 cm) of the 1 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press (3895 Auto-M, Carver, Wabash, Ind.) where it was sintered, then compressed to 20 MPa at about 194° C. for 10 minutes, then cooled to room temperature under pressure. Then, the puck was cooled for approximately 1.5 hours under pressure.

Two pucks were placed on top of each other (to obtain a sample with double the effective diffusion distance from the surface) and masked with aluminum foil on 5 sides except for one circular surface. The samples were placed in a pre-heated nitrogen convection oven at 290° C. with the unmasked surface exposed to nitrogen flow. The pucks were kept in the oven under these conditions for approximately 290 min. Samples were removed from the oven and were cooled in air at room temperature.

Following the cooling step, the top puck was irradiated by electron beam irradiation using a Van-de-Graff generator at 3.0 MeV to a dose of 175 kGy at 25 kGy/pass. One thin section each (3.2 mm thick) was machined close to the top or bottom of the extracted and irradiated puck. Dog-bones were stamped from these thin sections and tested at 10 mm/min in tension according to ASTM D-638 (Type V; n=4). Yield strength (YS), ultimate tensile strength (UTS) and elongation to break (EAB) are reported. Elongation to break was determined by a laser extensometer. The results are reported in Table 1 below.

TABLE 1

The tensile mechanical properties of high temperature extracted and radiation cross-linked 1 wt % vitamin E-blended UHMWPE

|  | Yield Stress (MPa) | Break Stress (MPa) | Elongation at break (%) |
| --- | --- | --- | --- |
| Extracted, irradiated surface | 21 ± 2 | 31 ± 4 | 226 ± 12 |
| Extracted, irradiated bulk | 22 ± 1 | 41 ± 3 | 327 ± 26 |

There was no difference in the yield strength (YS) of the surface and bulk regions of extracted and irradiated UHMWPE (Table 1). The bulk region of the extracted and irradiated UHMWPE had higher UTS and EAB than that of the surface (p<0.01 and p<0.01, respectively).

TABLE 2

The tensile mechanical properties of high temperature extracted-doped and radiation cross-linked 0.3 wt % vitamin E-blended UHMWPE

|  | Yield Stress (MPa) | Break Stress (MPa) | Elongation at break (%) |
| --- | --- | --- | --- |
| Extracted, irradiated surface | 21 ± 0.1 | 37 ± 5 | 228 ± 11 |
| Extracted, irradiated bulk | 22 ± 0.3 | 45 ± 8 | 361 ± 29 |

Example 30

Tensile Testing of Surface Extracted, Bulk Diffused and Radiation Cross-linked Vitamin E Containing UHMWPE Pucks A 5 wt % concentration mixture of vitamin E with UHMWPE (GUR 1050) was prepared by first mixing isopropyl alcohol (IPA) with vitamin, then mixing the vitamin E-IPA solution with virgin UHMWPE powder, then evaporating off the solvent in a vacuum oven at an elevated temperature (approximately 60° C.). The mixture was diluted with GUR 1050 to obtain GUR 1050 with 3 wt % and 0.3 wt % vitamin E respectively.

Two pucks (diameter 10 cm, thickness 1-1.1 cm) of 3 wt % and 0.3 wt % vitamin E-containing UHMWPE blend were prepared via compression molding. The powder was pre-heated in a vacuum oven under partial vacuum/inert gas at 190-210° C. for approximately 2 hours. Then, the mold/powder was transferred to an automatic press where it was sintered, then compressed to 20 MPa at about 194° C. for 10 minutes, then cooled to room temperature under pressure. Then, the puck was cooled for approximately 1.5 hours under pressure.

Two pucks were placed on top of each other (to extract from the top puck and diffuse vitamin E from the bottom puck) and masked with aluminum foil from 5 sides except one circular surface with lower concentration (0.3 wt % vitamin E puck). They were placed in a pre-heated nitrogen convection oven at 290° C. with the unmasked surface exposed to nitrogen flow. The pucks were kept in the oven under these conditions for approximately 290 minutes. Samples were removed from the oven and were cooled in air at room temperature. After cooling down, the top puck was irradiated by electron beam irradiation using a Van-de-Graff generator at 3.0 MeV to a dose of 175 kGy at 25 kGy/pass.

Thin sections (2 mm thick) were cut from the surface (1-3 mm) and bulk (7-9 mm) regions of the top puck and dog bones were stamped for tensile measurements. Testing was performed according to ASTM D-638 method at a crosshead displacement of 10 mm/min (Type 5; n=4). Yield strength (YS), ultimate tensile strength (UTS) & elongation to break (EAB) are reported. Strain was measured by a laser extensometer. Before irradiation, there was no significant difference between the mechanical strength (UTS) of the top section (surface) and bottom section (bulk) obtained from the top puck. While after irradiation, the material strength of the top section (UTS) decreased from 45.7±3.1 MPa to 36.7±4.8 MPa (p=0.03) with bulk strength still the same as its non-irradiated counterpart (Table 2).

Although the present invention has been described in detail with reference to certain embodiments, one skilled in the art will appreciate that the present invention can be practiced by other than the described embodiments, which have been presented for purposes of illustration and not of limitation. Therefore, the scope of the invention should not be limited to the description of the embodiments contained herein.

All documents cited herein are, in relevant part, incorporated herein by reference; the citation of any document is not to be construed as an admission that it is prior art with respect to the present invention.

What is claimed is:

1. A method of making a polymeric material with a spatially controlled distribution of at least one additive, the method comprising:
   blending the at least one additive with a polymeric material;
   consolidating the polymeric material after blending the at least one additive with the polymeric material;
   thereafter heating at about 200° C. to about 500° C. at least a portion of at least one surface of the consolidated additive-blended polymeric material to extract the at least one additive before any cross-linking of the consolidated additive-blended polymeric material; and
   thereafter cooling the heated consolidated additive-blended polymeric material, thereby forming a polymeric material with a spatially controlled distribution of additive.

2. The method of claim 1, wherein the at least one additive is vitamin E.

3. The method of claim 1, wherein the at least one additive comprises about 0.001 wt % to about 50 wt % of the polymeric material.

4. The method of claim 1, wherein the polymeric material is selected from an extrudate, pellets, a resin powder, flakes, a liquid, or a gel.

5. The method of claim 1, wherein following the step of consolidating, the polymeric material is heated to a temperature above the melting temperature of the polymeric material, thereby relieving the residual stresses from consolidation.

6. The method of claim 5, wherein the polymeric material is heated for a duration of from about 1 minute to about 36 hours.

7. The method of claim 1, wherein the step of consolidating further comprises at least one of compression molding, ram extrusion, extrusion, hot or cold isostatic pressing, injection molding, and direct compression molding.

8. The method of claim 1, wherein the step of heating further comprises heating in the presence of at least one of an inert gas, a non-inert gas, air, a vacuum, a liquid, a liquid with gas bubbled through, a liquid saturated with gas, a supercritical fluid, a convection current, and combinations thereof.

9. The method of claim 1, wherein at least one of the consolidated and machined forms of the polymeric material has a thickness from about 1 millimeter to about 20 centimeters.

10. The method of claim 2, wherein the step of heating further comprises heating at about 220° C. to about 290° C. and wherein after cooling the polymeric material the at least one surface has a vitamin E index of less than 0.10 within 2 mm from the at least one surface as measured by Fourier Transform Infrared Spectroscopy (FTIR).

11. The method of claim 1, wherein the step of cooling further comprises cooling until the temperature of the polymeric material is below the crystallization temperature.

12. The method of claim 1, wherein an annealing step is used for homogenization of the additive and is performed a temperatures selected from below and above the melting point of the polymeric material.

13. The method of claim 1, further comprising a medical device.

14. The method of claim 13, wherein the medical device is selected from the group consisting of acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, interpositional devices for any joint, sutures, tendons, heart valves, stents, and vascular grafts.

15. The method of claim 14, wherein the medical device is packaged and terminally sterilized in appropriate packaging.

16. The method of claim 15, wherein sterilization comprises gas sterilization, gas plasma sterilization, and ionizing radiation.

17. The method of claim 1, wherein the heating at about 200° C. to about 500° C. at least a portion of at least one surface of the consolidated additive-blended polymeric material to extract the at least one additive is done at ambient pressure.

* * * * *

UNITED STATES PATENT AND TRADEMARK OFFICE
CERTIFICATE OF CORRECTION

PATENT NO. : 9,889,224 B2
APPLICATION NO. : 14/420005
DATED : February 13, 2018
INVENTOR(S) : Ebru Oral et al.

Page 1 of 1

It is certified that error appears in the above-identified patent and that said Letters Patent is hereby corrected as shown below:

In the Specification

Column 13, Line 53, "Eat" should be --E at--.

Signed and Sealed this
Twenty-second Day of January, 2019

Andrei Iancu
*Director of the United States Patent and Trademark Office*